US008329444B2

(12) United States Patent
Chen et al.

(10) Patent No.: US 8,329,444 B2
(45) Date of Patent: Dec. 11, 2012

(54) **STRAINS OF *ZYMOMONAS MOBILIS* FOR FERMENTATION OF BIOMASS**

(75) Inventors: Rachel Ruizhen Chen, Marietta, GA (US); Yun Wang, Winnipeg (CA); Hyun-Dong Shin, Dunwoody, GA (US); Manoj Agrawal, Atlanta, GA (US); Zichao Mao, Kunming (CN)

(73) Assignee: Georgia Tech Research Corporation, Atlanta, GA (US)

( * ) Notice: Subject to any disclaimer, the term of this patent is extended or adjusted under 35 U.S.C. 154(b) by 649 days.

(21) Appl. No.: 12/428,916

(22) Filed: Apr. 23, 2009

(65) Prior Publication Data

US 2009/0269797 A1    Oct. 29, 2009

Related U.S. Application Data

(60) Provisional application No. 61/125,302, filed on Apr. 23, 2008.

(51) Int. Cl.
*C12N 1/36* (2006.01)
(52) U.S. Cl. ...................... 435/245; 435/243; 435/252.1; 435/260; 435/234.1
(58) Field of Classification Search .................. None
See application file for complete search history.

(56) References Cited

U.S. PATENT DOCUMENTS 4,900,670 A    2/1990 Zall et al.
7,223,575 B2   5/2007 Zhang et al.

FOREIGN PATENT DOCUMENTS

WO    WO 2004/037973 A1    5/2004
WO    WO 2009/058927 A1    5/2009

OTHER PUBLICATIONS

Afendra et al., "Characterization of the mobilization region of the *Zymomonas mobilis* ATCC10988 plasmid pZMO3", 41 Plasmid (1999), pp. 73-77.
Almeida et al., "Increased tolerance and conversion of inhibitors in lignocellulosic hydrolysates . . .", 82 J. Chem. Tech. and Biotech. (2007), pp. 340-349.
Baumler et al., "Enhancement of Acid Tolerance in *Zymomonas mobilis*. . .", 134 Appl. Biochem. & Biotech. (2006), pp. 15-26.
Callens, et al., "Catalytic properties of D-xylose isomerase from *Streptmyces violaceoruber*", 8 Enzyme and Microbial Technology (1986), pp. 696-700.
Dien et al., "Bacteria engineered for fuel ethanol production: current status", 63 Appl. Microbiol. Biotech. (2003), pp. 258-266.
El-Mansi, Fermentation Microbiology and Biotechnology (2nd Ed), CRC Press, New York (2007).
Feldman et al., "Pentose metabolism in *Zymomonas mobilis* wild-type and recombinant strains", 38 Appl. Microbiol. Biotechnol. (1992), pp. 354-361.
Foster, "Mechanisms of Stationary Phase Mutation: A Decade of Adaptive Mutation", 33 Annu. Rev. Genet. (1999), pp. 57-88.
Foster, "Adaptive mutation: the uses of adversity", 47 Annu. Rev. Microbiol. (1993), pp. 467-504.
Fraser-Reid et al., Glycosience: Chemistry and Chemical Biology I-III, Springer, New York (2001).
Han et al., "Adsorptive membranes vs. resins for acetic acid removal.. ", 193 Desalination (2006), pp. 361-366.
Jeon et al., "Linetic analysis of ethanol production by an acetate-resistant strain . . .", 24 Biotechnol. Lett. (2002), pp. 819-824.
Kim et al., "Kinetic and Nuclear Magnetic Resonance Studies of Xylose Metabolism . . .", 66(1) App. Env. Microbiol. (2000), pp. 186-193.
Lawford et al., "Performance testing of *Zymomonas mobilis* Metabolically Engineered . . .", 98-100 App. Biochem. Biotech. (2002), pp. 429 - 448.
Lawford et al., "The Effect of Acetic Acid on Fuel Ethanol Production by *Zymomonas* ", 39/40 Appl. Biochem. & Biotech. (1993), pp. 687-699.
Lee et al., "High Productivity Ethanol Fermentations With *Zymomonas Mobilis* Using Continuous Cell Recycle", 2(11) Biotech. Lett. (1980), pp. 487-492.
Mohagheghi et al., "Cofermentation of Glucose, Xylose, and Arabinose by Genomic DNA . . .", 98-100 Appl. Biochem. & Biotech. (2002), pp. 885-898.
Rogers et al., "Ethanol Fermentation by Highly Productive Strains of *Zymomonas Mobilis*", Adv. Biotechnol., [Proc. Int. Ferment. Symp.] 6th (1980), pp. 189-194.
Rogers et al., "High productivity Ethanol Fermentations with *Zymomonas Mobilis*", 15(6) Process Biochem. (1980), pp. 7-11.
Rogers et al., "Kinetics of Alcohol Production by *Zymomonas Mobilis* at High Sugar Concentrations", Biotech. Lett. (1979), pp. 165-170.
Rosenberg, "Evolving Responsively: Adaptive Mutation", 2(7) Nature Rev. Genetics (2001), pp. 504-515.
Seo et al., "The genome sequence of the ethanologenic bacterium *Zymomonas mobilis* ZM4", 23(1) Nature Biotechnology (2005), pp. 63-68.
Zhou et al., "Production of Optically Pure D-Lactic Acid in Mineral Salts Medium by Metabolically . . .", 69(1) Appl. & Envir. Microbiol. (2003), pp. 399-407.
Wang, "Development of Acetic-acid Tolerant *Zymomonas Mobilis* Strains through Adaption" (in partial fulfillment of the requirements for the MS in chemical and biomolecular engineering degree to Georgia Institute of Technology), Apr. 24, 2008.
Zhang et al. "Metabolic engineering of a pentose metabolism pathway in ethanologenic *Zymomonas mobilis*", 267 Science (1995), pp. 240-243.

(Continued)

*Primary Examiner* — Jennifer Graser
(74) *Attorney, Agent, or Firm* — Gregory L. Porter; Christopher D. Northcutt

(57) ABSTRACT

The present invention relates to methods of obtaining *Z. mobilis* mutant strains that are more tolerant to one or more inhibitors or more capable of efficiently fermenting one or more carbohydrates. Such inhibitors include ethanol, aliphatic acids, such as acetic acid, formic acid; furan derivatives, such as 2-furaldehyde, 2-furoic acid; and phenolic compounds, such as vanillin and hydroxybenzoic acid. Such carbohydrates may include xylose, arabinose, mannose and mixtures thereof. These mutant strains may be employed to, for example, effectively and efficiently prepare ethanol from biomass.

17 Claims, 36 Drawing Sheets

OTHER PUBLICATIONS

Zhang, "Engineering *Zymomonas mobilis* for efficient ethanol production from lignocellulosic feedstocks", Abstract of Papers, 225th ACS National Meeting, New Orleans (2003).

Joachimsthal et al., "A mutant of *Zymomonas mobilis* ZM4 capable of ethanol production . . .", 20(2) Biotech. Lett. (1998), pp. 137-142.

Rogers et al., *Zymomonas mobilis* for fuel ethanol and higher value products, 108(1) Adv. in Biochem. Eng. Biotech. (2007), pp. 263-288.

Bai et al., "Ethanol fermentation technologies from sugar and starch feedstocks", 26(1) Biotech. Adv. (2007), pp. 89-105.

Lawford et al., "Fermentation performance characteristics of a prehydrolyzate-adapted xylose-fermenting . . .", 77-79 Appl. Biochem. & Biotech. (1999), pp. 191-204.

Lawford et al., "Continuous culture studies of xylose-fermenting *Zymomonas mobilis*", 70-72 Appl. Biochem. & Biotech. (1998), pp. 353-367.

Rogers et al,, "Application of Biotechnology to Industrial Sustainability", 83(6) Proc. Safety & Envir. Prot. (2005), pp. 499-503.

(A)

(B)

(C)

(A)

(B)

(C)

(A)

(B)

(C)

(A)

(B)

(C)

(A)

(B)

(A)

(B)

(C)

(A)

(B)

(A)

(B)

(A)

(B)

(A)

(B)

(A)

(B)

(A)

(B)

(A)

(B)

(A)

(B)

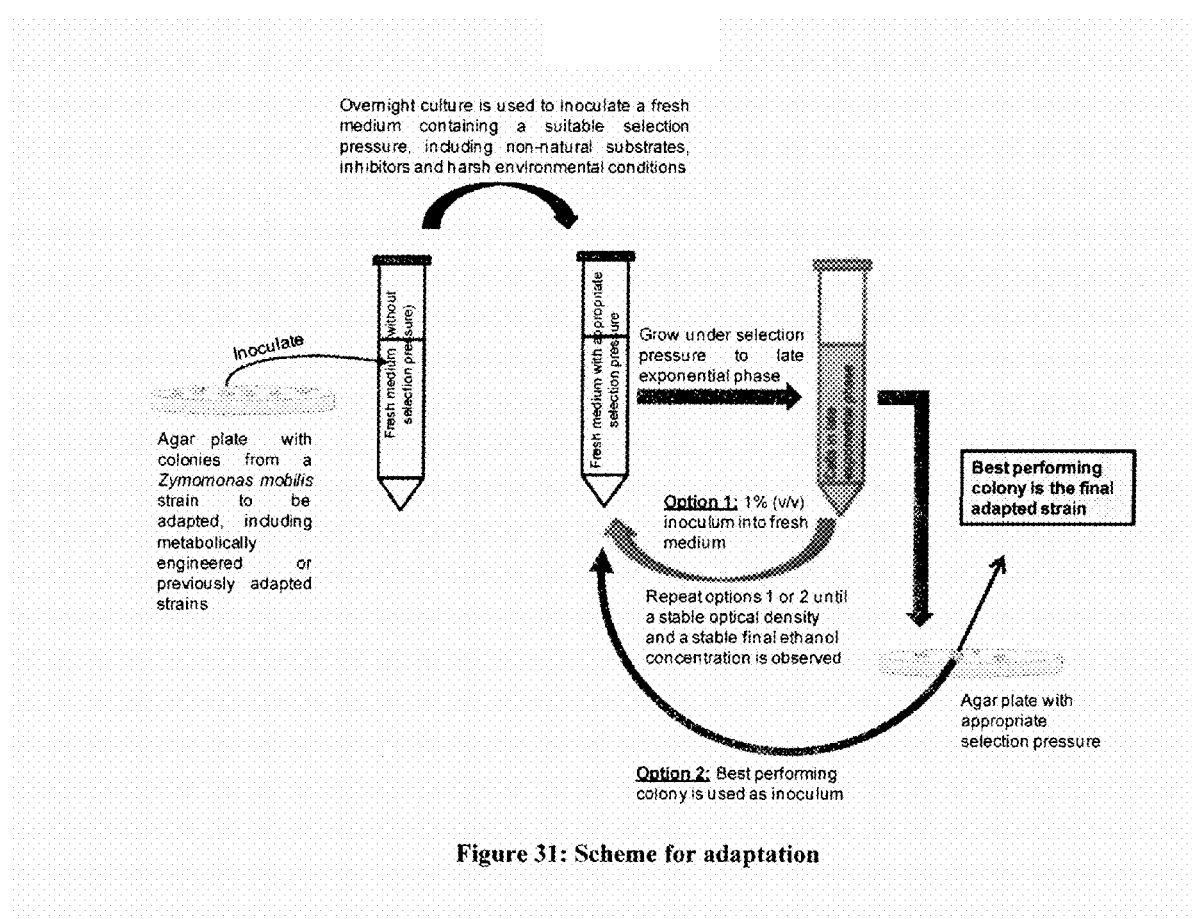
Figure 31: Scheme for adaptation

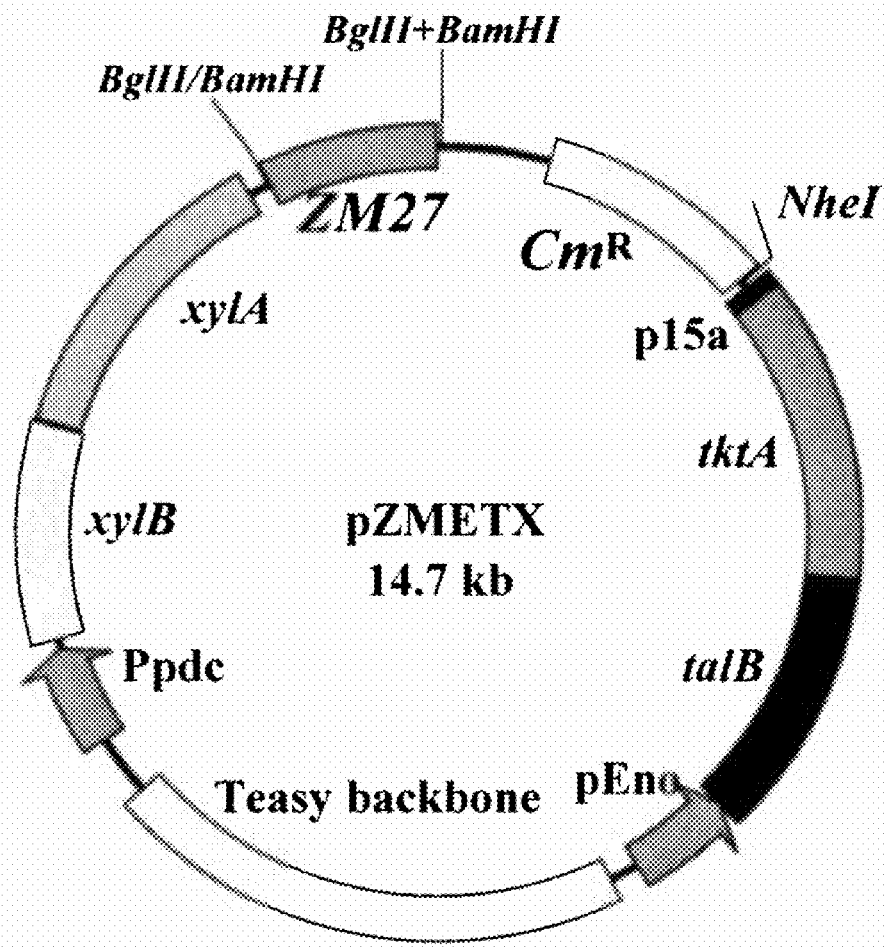
Figure 32: Plasmid map of pZMETX

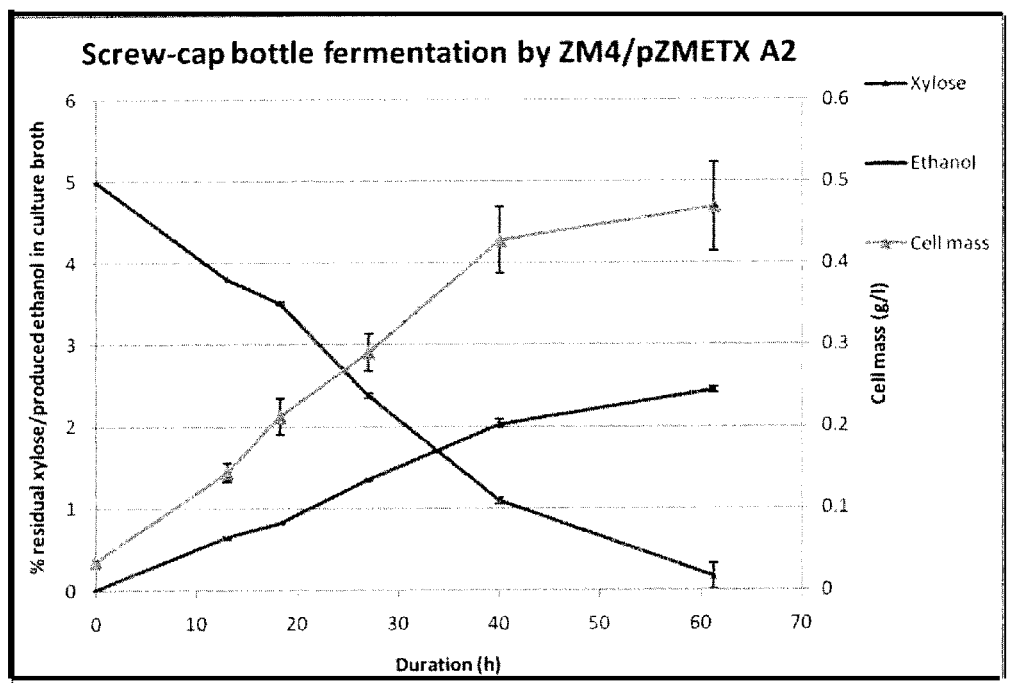
Figure 33: Screw-cap bottle fermentation of 5% (w/v) xylose by ZM4/pZMETX A2 without pH control

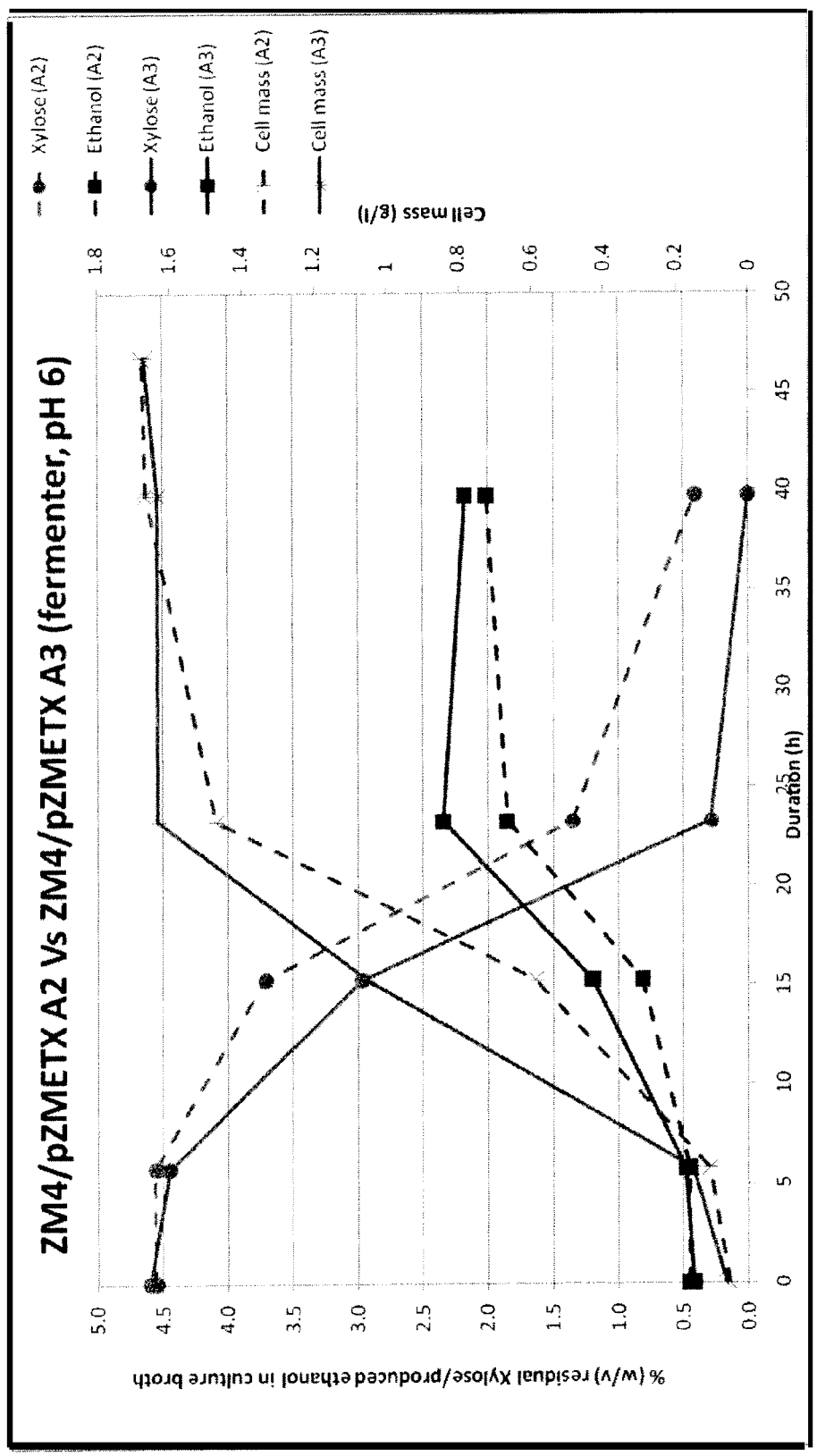
Figure 34: Comparison of fermentation performances of ZM4/pZMETX A2 and ZM4/pZMETX A3 in a fermenter with pH controlled at 6 in an anaerobic nitrogen gas atmosphere

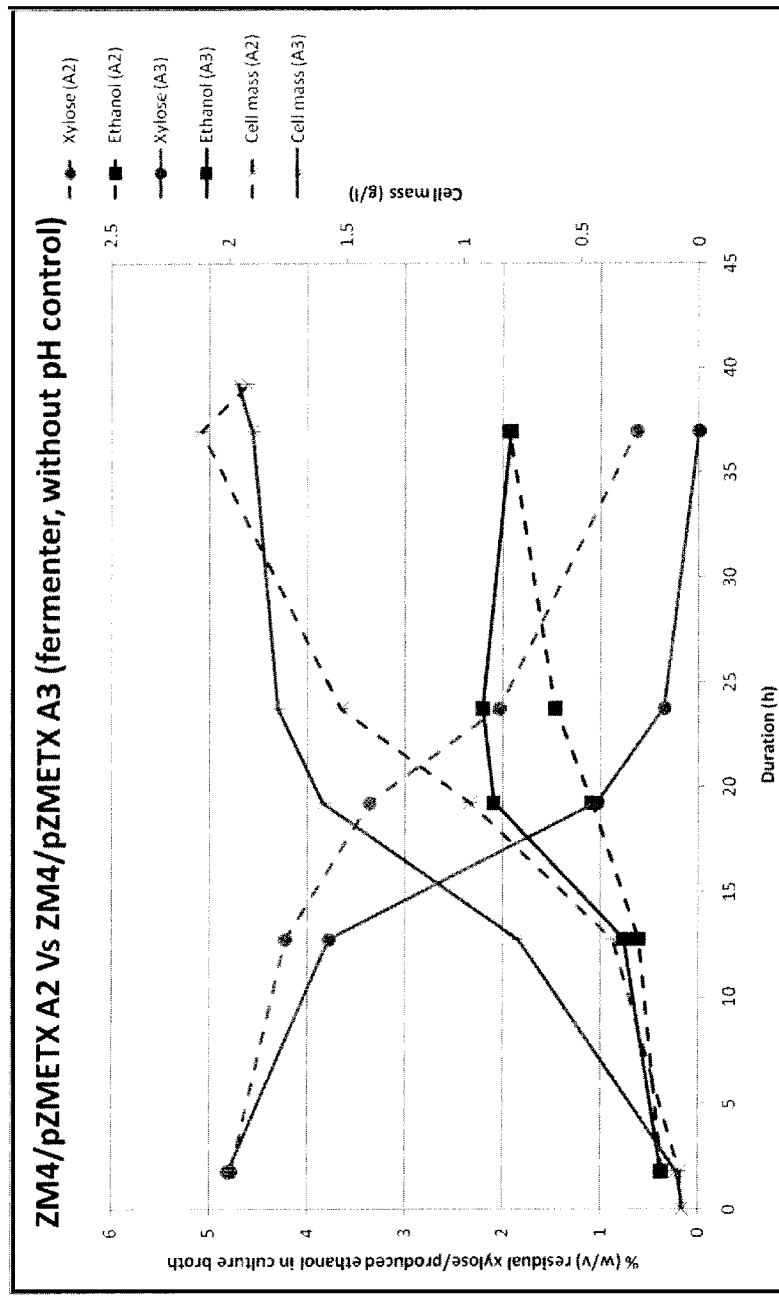
Figure 35: Comparison of fermentation performances of ZM4/pZMETX A2 and ZM4/pZMETX A3 in a fermenter without pH control in an anaerobic nitrogen gas atmosphere

STRAINS OF ZYMOMONAS MOBILIS FOR FERMENTATION OF BIOMASS

RELATED APPLICATIONS

This application claims priority to U.S. provisional application 61/125,302 filed Apr. 23, 2008 which for purposes of U.S. patent practice is fully incorporated herein by reference to the extent it is not inconsistent with the instant application.

FIELD OF THE INVENTION

Provided herein are *Zymomonas mobilis* (*Z. mobilis*) mutant strains that are more tolerant to one or more various inhibitors commonly encountered in biomass fermentation, methods of obtaining the mutant strains and methods of using the mutant strains to obtain ethanol from biomass. The *Z. mobilis* mutant strains obtained by the processes provided herein are (1) more tolerant to one or more inhibitors including, but not limited to ethanol, aliphatic acids, such as acetic acid, formic acid; furan derivatives, such as 2-furaldehyde, 2-furoic acid; and phenolic compounds, such as vanillin and hydroxybenzoic acid and/or (2) more capable of fermenting one or more carbohydrates such as those selected from xylose, arabinose, mannose and mixtures thereof.

BACKGROUND AND SUMMARY OF THE INVENTION

As the demand of energy increases worldwide, fossil fuel is rapidly depleted. Therefore, alternative sources of energy have to be evaluated to meet the global energy demand. Methane, hydrogen and ethanol are considered as potential substitutes for fossil fuels. Among these three candidates, ethanol is commonly considered to be a good choice for an alternative liquid fuel in the near term.

The process of ethanol production using biomass as a feedstock is well known (http://www.vermontbiofuels.org/biofuels/ethanol.shtml). In this process, both glucose and pentose are fermented to ethanol by a microorganism. Currently, yeast (*Saccharomyces cerevisiae*) is often used in the process, see, Almeida, J. R. M., et al., *J. of chem. tech. and biotech.*, 2007, 82(4): p. 340-349.

When choosing a microorganism for fermentation, several important traits may be considered, including yield, ethanol tolerance, productivity, and growth requirements, see, Dien, B. S., et al., *Applied microbial biotechnology*, 2003, 63: p. 258-266. Among these traits, ethanol yield has received much attention because feedstock may account for greater than one-third of the production costs. If ethanol yield is high, less feedstock would be needed to produce the same amount of ethanol. Consequently, the production cost could be reduced, so high ethanol yield is often important. Based on this requirement, *Zymomonas mobilis*, which was found to have the highest ethanol yield on sugar complex containing glucose, see, Lee, K. J., et al., *Biotechnology letters*, 1980. 2(11): p. 487-492; Rogers, P. L., et al., *Process Biochemistr*, 1980, 15(6): p. 7-11; and Rogers, P. L., et al., *Adv. Biotechnol.*, [Proc. Int. Ferment. Symp.] 6th, 1980, became one of the most promising microorganisms having the potential to replace the yeast for ethanol production. This microorganism has been demonstrated to have ethanol yields up to 97% of the theoretical value. When compared with traditional yeast fermentation, it could achieve 5 to 10% higher yield, see, El-Mansi, M., *Fermentation microbiology and biotechnology*, 2007: CRC Press; and Fraser-reid, B., et al., *Glycosience: Chemistry and Chemical Biology.* 2001: Springer. Another advantage of *Z. mobilis* is its high ethanol productivity. The volumetric ethanol productivity of *Z. mobilis* could be five-fold higher than *S. cerevisiae*. Additional advantages of *Z. mobilis* for ethanol production are reported by Rogers, P. L., et al., in *Biotechnology letter*, 1979, 1: p. 165-170, and include the high sugar tolerance, the low production cost and the ability to ferment sugar at low pH. *Z. mobilis* could grow at high concentrations of glucose (10-25%). This microorganism is also acid tolerant and could grow over a pH range of 3.5 to 7.5. So the fermentations are generally resistant to bacterial contamination.

Although *Z. mobilis* is better than yeast in some aspects, it has not been used commercially for a number of reasons. First, *Z. mobilis* typically only uses glucose, fructose and sucrose as their substrates. Since pentoses such as xylose is a major component of hemicellulose in most biomass feedstock, it is usually essential for a fermenting microorganism to use this sugar in ethanol production for a good product yield from biomass. Fortunately metabolic engineering has been successfully applied to develop a *Zymomonas* strain to ferment xylose, (see, Zhang, M., Engineering *Zymomonas mobilis* for efficient ethanol production from lignocellulosic feedstocks. ACS national meeting, 2003 and U.S. Pat. No. 7,223,575, which is incorporated herein by reference to the extent that it is not inconsistent) and as well as arabinose, see, Mohagheghi, A., et al., *Applied biochemistry and biotechnology*, 2002, 98-100: p. 885-898. By genetic engineering technology, engineered *Z. mobilis* could potentially use all sugars present in most biomass feedstock. Secondly, *Z. mobilis* is sensitive to various inhibitors, including ethanol, aliphatic acids, such as acetic acid, formic acid; furan derivatives, such as 2-furaldehyde, 2-furoic acid; and phenolic compounds, such as vanillin and hydroxybenzoic acid, founds in the biomass, see, Lawford, H. G., et al., *Applied biochemistry and biotechnology*, 1993, 39/40: p. 687-699. As reported by Jeon, Y. J., et al., *Biotechnology letters*, 2002, 25: p. 819-824, the toxicity of acetic acid intensified during xylose fermentation. The pretreated biomass by dilute-acid usually contains up to 1.5% acetic acid (w/v) due to the hydrolysis of the acetylated pentoses in hemicellulose. Before using *Z. mobilis* in industry, this inhibition problem has to be addressed.

Several researchers have tried to develop acetic acid tolerant strains *Z. mobilis* by genetic modification. Among them, Rogers et al. used N-methyl N'-nitro-N-nitrosoguanidine (NTG) treatment in 1998 to develop several strains of *Z. mobilis*. Baumler et al., in *Applied biochemistry and biotechnology*, 2006, 134: p. 15-26, proposed recombinant DNA technology to enhance the acid tolerance in *Z. mobilis* (CP4). Among other methods that have been tried to address the acetic acid toxicity of *Z. mobilis* include, optimizing the fermentation conditions by removal of acetic acid from pretreated biomass by ion-exchange resins and ion exchange membranes (see, Han, B., et al., *Desalination*, 2006, 193: p. 361-366) and finding optimum fermentation conditions for the recombinant *Z. mobilis*.

Moreover, even though many modification methods are known, (see, Foster, P. L., *Annual review of genetics,* 1999, 33: p. 57-88; Foster, P. L., *Annual reviews of microbiology,* 1993, 47: p. 467-504 and Rosenberg, S. M., *Evolving responsively: Adaptive mutation.* Nature Reviews Genetics, 2001. 2(7): p. 504-515), nobody has successfully modified *Z. mobilis* to develop inhibitor tolerance and/or pentose consumption in a cost-efficient manner. Accordingly, there remains a continuing need to develop more inhibitor tolerant (such as acetic acid tolerant) strains of *Z. mobilis* that can be used for ethanol production from biomass. There also remains a continuing need to develop a strain more capable of fermenting pentoses.

Provided herein are *Zymomonas mobilis* mutant strains that are more tolerant to various inhibitors sometimes found in biomass and/or that may ferment additional carbohydrates, methods of obtaining the mutant strains, and methods of using the mutant strains to prepare ethanol from biomass.

In one embodiment the invention pertains to processes for adaptively mutating a bacteria such as one from the genus *Zymomonas*. The process of adaptively mutating the bacteria comprises sequentially culturing the bacteria in the presence of one or more selective pressures which are consecutively increased. Then, a mutant strain which is more adapted to the selective pressure is isolated.

In another embodiment, the invention pertains to making a *Zymomonas mobilis* strain more tolerant to an inhibitor. The process comprises first growing a *Zymomonas mobilis* strain in a medium substantially free of an inhibitor. Next, the *Zymomonas mobilis* strain is sequentially cultured in the presence of consecutively higher concentrations of the inhibitor. Then, a mutant strain adapted to a higher inhibitor concentration isolated.

In another embodiment, the invention pertains to a process for making a *Zymomonas mobilis* strain capable of increased carbohydrate fermentation of one or more carbohydrates selected from xylose, arabinose, mannose and mixtures thereof. The process comprises first growing a *Zymomonas mobilis* origin strain in a medium comprising glucose. Next, the *Zymomonas mobilis* strain is sequentially cultured in the presence of consecutively higher concentrations of one or more carbohydrates selected from xylose, arabinose, mannose and mixtures thereof and lower amounts of glucose. Then, a mutant strain capable of increased carbohydrate fermentation of one or more carbohydrate selected from xylose, arabinose, mannose and mixtures thereof is isolated.

In another embodiment, the mutant *Z.mobilis* strains made by the techniques of the present invention, e.g., acetic acid inhibitor tolerant *Z.mobilis* strains, often have a number of unique characteristics or combinations of unique characteristics. The non-naturally occurring, biologically pure *Zymomonas mobilis* mutant strain may be characterized by substantially exhibiting one or more of the following characteristics: (1) a lag phase of less than about one day, preferably less than 9 hours; or (2) a specific growth rate of at least about 0.15 h$^{-1}$, preferably at least about 0.3 h$^{-1}$ or (3) an ethanol yield of at least about 95% of theoretical yield; wherein the characteristics are exhibited while fermenting at a pH of about 6 in an RM medium with 50 g/L glucose and 1.6% acetic acid concentration. In some embodiments the strain substantially exhibits at least 2 or even all 3 of the aforementioned characteristics.

In another embodiment, the mutant *Z.mobilis* strains made by the techniques of the present invention, e.g., enhanced carbohydrate fermentation *Z.mobilis* strains, often have a number of unique characteristics or combinations of unique characteristics. The non-naturally occurring, biologically pure *Zymomonas mobilis* mutant strain may be characterized by substantially exhibiting one or more of the following characteristics: (1) an ethanol yield of at least about 85%, preferably at least about 90% of theoretical yield; or (2) a volumetric ethanol productivity of at least about 0.5, preferably at least about 0.8 grams of ethanol per liter of reactor per hour (g/l/h); or (3) a specific ethanol productivity of at least about 0.9, preferably at least about 0.95 grams per gram of dry cell mass per hour (g/g/h); or (4) a xylose consumption rate of at least about 1.8, preferably at least about 2.0 grams per gram of dry cell mass per hour (g/g/h); or (5) an ability to consume 5% (w/v) xylose in less than about 40 hours, preferably less than about 36 hours; wherein the characteristics are exhibited while fermenting in an RM medium with 50 g/L xylose without glucose.

In another embodiment, the invention pertains to a non-naturally occurring, biologically pure *Zymomonas mobilis* mutant strain characterized by substantially exhibiting one or more of the following characteristics:
(1) a lag phase of less than about one day; or
(2) a specific growth rate of at least about 0.15 h$^{-1}$; or
(3) an ethanol yield of at least about 95% of the theoretical yield;
(4) an ethanol yield of at least about 85% of theoretical yield; or
(5) a volumetric ethanol productivity of at least about 0.5 grams of ethanol per liter of reactor per hour; or
(6) a specific ethanol productivity of at least about 0.9 grams of ethanol per gram of dry cell mass per hour; or
(7) a xylose consumption rate of at least about 1.8 grams of xylose per gram of dry cell mass per hour; or
(8) an ability to consume 5% (w/v) xylose in less than about 40 hours; wherein the one or more characteristics (1)-(3) are exhibited while fermenting at a pH of about 6 in an RM medium with 50 g/L glucose and 1.6% acetic acid concentration and wherein the one or more characteristics (4)-(8) are exhibited while fermenting in an RM medium with 50 g/L xylose without glucose.

BRIEF DESCRIPTION OF THE FIGURES

FIG. 31 provides a schematic representation of an adaptive mutation.

FIG. 32 provides a plasmid map of pZMETX.

FIG. 33 provides data of fermentation of 5% xylose in a screw cap bottle.

FIG. 34 provides a comparison of fermentation performances of ZM4/pZMETX A2 and ZM4/pZMETX A3 in a fermenter with pH controlled at 6 in an anaerobic nitrogen gas atmosphere data of fermentation of 5% xylose in a fermenter.

FIG. 35 provides a comparison of fermentation performances of ZM4/pZMETX A2 and ZM4/pZMETX A3 in a fermenter without pH control in an anaerobic nitrogen gas atmosphere.

DETAILED DESCRIPTION OF THE INVENTION

Figure 1:
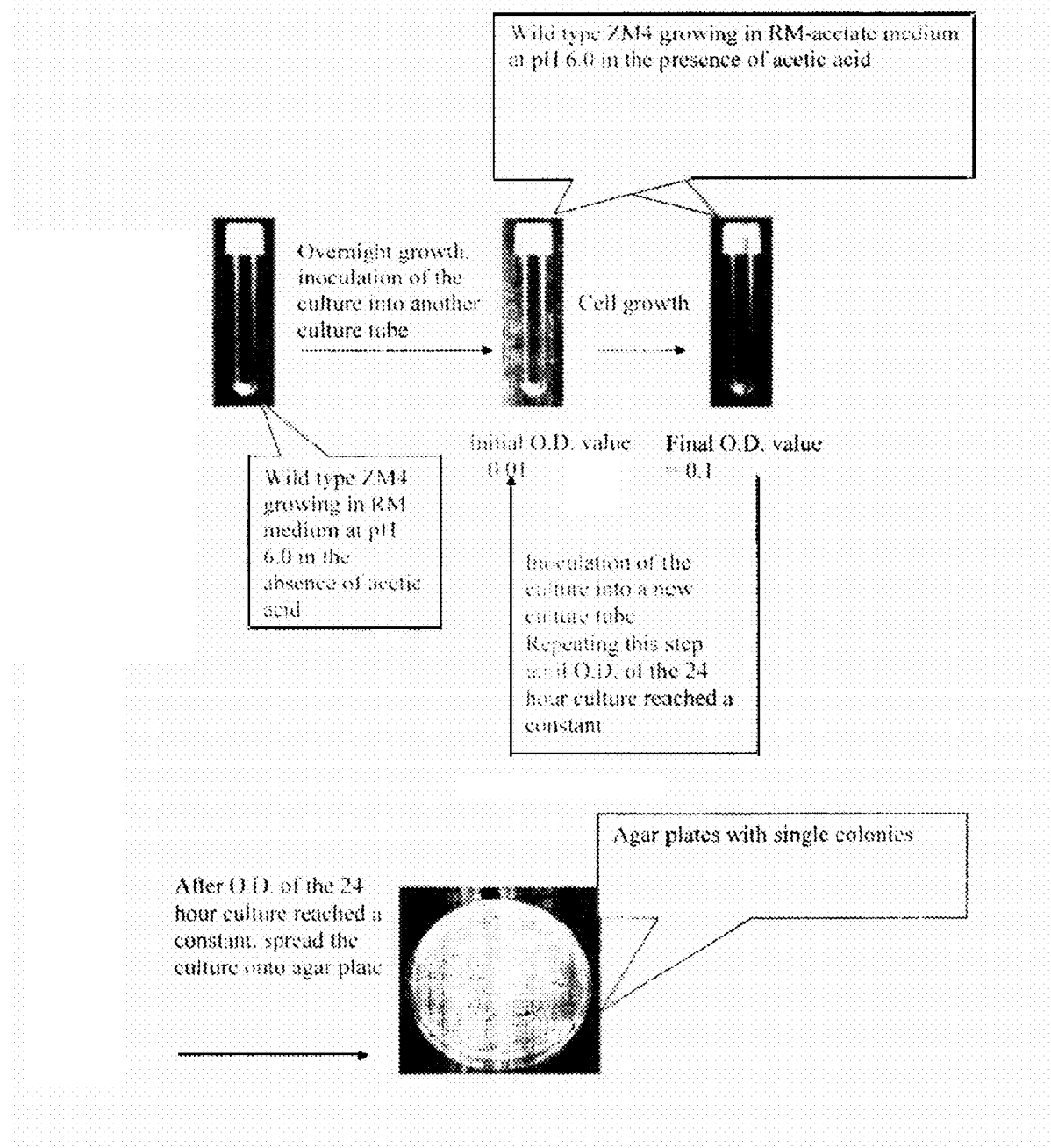
FIG. 1 illustrates an exemplary adaptive mutation process.

As used herein, a "mutant" refers to a microorganism that has undergone one or more mutations relative to a reference or origin microorganism. For example, the mutant *Z. mobilis* strains herein have undergone one or more mutations relative to an initial or original *Z. mobilis* strain such that the mutant strain can grow and produce ethanol in the presence of a higher amount, i.e., concentration, of one or more inhibitors. Such inhibitors include, but not limited to aliphatic acids, such as acetic acid, formic acid; furan derivatives, such as 2-furaldehyde, 2-furoic acid; phenolic compounds, such as vanillin and hydroxybenzoic acid, oxygen, and mixtures thereof. These inhibitors may be present in a pure form or in solution, e.g., aqueous or gaseous solutions.

The term "wild-type" refers to a reference microorganism that does not comprise a mutation known to be associated with a phenotype of interest. Wild-type *Z. mobilis* strains may be employed as the reference or original microorganisms. In addition, *Z. mobilis* strains that are not wild-type, but rather, comprise a partially developed mutation may employed as the reference microorganism. For example, a *Z. mobilis* strain which has been mutated (adaptively or otherwise) to be at least partially resistant to inhibitors may be employed as a reference microorganism. The procedures described herein can then be employed to more fully mutate the strain to be even more resistant to increased amounts of one or more inhibitors.

A used herein, "adaptive mutation" generally refers to a mutation of a process that produces mutations specific to the selective pressure. In contrast to random mutations, such as UV or chemical mutagens, the adaptive mutation processes herein tend to produce only useful mutations. In other words, there is one or more mechanisms of preventing one or more useless genetic changes.

As used herein, the term "consecutively higher concentrations" refers to concentrations succeeding one another so that the general trend of subsequent cultures is of increasing inhibitor concentration. Similarly, as used herein, the term "consecutively lower pH" refers to concentrations succeeding one another so that the general trend of subsequent cultures is of lowering pH. For example, in the processes described herein, the acetic acid concentration in the culture medium may be generally increased in regular or irregular increments of about 0.05, 0.1 or 0.2%. In the description and claims, the concentration of acetic acid is expressed as w/v percentage. Thus, for example, 0.1% acetic acid refers to 0.1 g acetic acid in 100 ml medium.

The term "fermentable sugar" refers to oligosaccharides and monosaccharides that can be used as a carbon source by *Z. mobilis* in a fermentation process.

As used herein "suitable medium" refers to a medium that supports growth of *Z. mobilis* under various conditions. In certain embodiments, the suitable medium includes, for example, glucose, yeast extract, and monobasic potassium phosphate.

As used herein, "substantially free" refers to a medium that does not contain measurable amount of the specified inhibitor or mixture of inhibitors. For example, a medium substantially free of acetic acid refers to a medium that does not contain acetic acid in amounts that can be measured by conventional techniques. In certain embodiments, the amount of the inhibitor, for example, acetic acid, in a culture medium substantially free of acetic acid is less than about 0.0001% or less than about 0.001%. In certain embodiments, the culture medium is free of any inhibitor. In certain embodiments, the culture medium is free of any acetic acid.

As used herein, the term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "biomass" includes untreated biomass or treated biomass, e.g., biomass that has been treated in some manner prior to saccharification. Generally, biomass includes any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

As used herein, "suitable fermentation conditions" refers to conditions that support the production of ethanol using a *Z. mobilis* strain such as those described herein. Such conditions may include suitable pH, nutrients and other medium components, temperature, atmosphere, and other environmental factors.

General Process of Adaptive Mutation for Bacteria

In general, the present invention pertains to processes for adaptively mutating a bacteria such as one from the genus *Zymomonas*. The process of adaptively mutating the bacteria comprises sequentially culturing the bacteria in the presence of one or more selective pressures which is consecutively increased. Then, a mutant strain which is more adapted to the selective pressure is isolated. The selective pressures may be anything from harsh conditions which may include growth inhibitors such as aliphatic acids, such as acetic acid, formic acid; furan derivatives, such as 2-furaldehyde, 2-furoic acid; and phenolic compounds, such as vanillin and hydroxybenzoic acid, extreme conditions like pH or temperature, or fermentation of one or more substances that *Zymomonas* does not typically ferment such as xylose. A general process is depicted in FIG. 31.

Adaptive Mutation Process for *Zymomonas mobilis* Mutant Strains More Tolerant to Inhibitors and/or Capable of Fermenting Xylose Provided herein are *Zymomonas mobilis* mutant strains that are more tolerant to various inhibitors found in a pretreated biomass, methods of obtaining the mutant strains and methods of using the mutant strains to prepare ethanol from biomass. The *Z. mobilis* mutant strains obtained by the processes provided herein are more tolerant to inhibitors including, but not limited to aliphatic acids, such as acetic acid, formic acid; furan derivatives, such as 2-furaldehyde, 2-furoic acid; and phenolic compounds, such as vanillin and hydroxybenzoic acid.

Also, provided herein are *Zymomonas mobilis* mutant strains that are more capable of fermenting substances that *Zymomonas mobilis* normally does not ferment, methods of obtaining the mutant strains and methods of using the mutant strains to prepare ethanol from biomass.

In one aspect, provided herein is a process for making a *Zymomonas mobilis* strain more tolerant to an inhibitor comprising: a) growing a *Zymomonas mobilis* strain in a medium substantially free of an inhibitor; b) sequentially culturing the *Zymomonas mobilis* strain in the presence of consecutively higher concentrations of the inhibitor; and c) isolating a mutant strain adapted to a higher inhibitor concentration.

In another aspect, provided herein is a process for making a *Zymomonas mobilis* strain more capable of increased carbohydrate fermentation of one or more carbohydrates that conventional *Zymomonas mobilis* strains such as wild-type strains do not readily ferment. Such carbohydrates may be selected from xylose, arabinose, mannose and mixtures thereof. The process comprises: a) growing a *Zymomonas mobilis* origin strain in a medium comprising glucose b) sequentially culturing the *Zymomonas mobilis* strain in the presence of consecutively higher concentrations of one or more carbohydrates selected from xylose, arabinose, mannose, and mixtures thereof and lower amounts of glucose; and c) isolating a mutant strain capable of increased carbohydrate fermentation of one or more carbohydrate selected from xylose, arabinose, mannose and mixtures thereof.

The amount and length of sequential culturing in the processes differs depending upon the desired outcome(s), inhibitors, and/or carbohydrates to be fermented. Accordingly, the processes are typically continued for as long as necessary to achieve the desired results. In some cases, it is advantageous to at least continue with sequential culturing until the desired selective pressure, e.g., resistance to inhibition or xylose fermentation, is no longer measurably improved in some respect. Similarly, in some cases it may be desirable to continue until the isolated mutant is stabilized for one or more of following: growth rate, cell mass concentration, ethanol production from biomass, or a combination thereof. Typically, steps b) and c) in the processes are repeated at least once. In certain embodiments, the steps b) and c) are repeated 2, 3 or more times.

The sequential culturing of consecutively higher concentrations of inhibitor (and/or consecutively lower pH and/or higher concentration of carbohydrates) do not require that each and every successive culture have a higher inhibitor concentration (and/or lower pH and/or higher concentration of carbohydrates) than the preceding one so long as the general trend of subsequent cultures is of increasing inhibitor concentration (or lowering pH or increasing carbohydrate concentration). For example, the cultures of increasing inhibitor concentration may be interspersed with cultures having an inhibitor concentration which is the same as or even lower than the preceding one so long as the general trend is increasing. However, in one embodiment, the sequential culturing of consecutively higher concentrations of inhibitor is not interspersed with cultures having an inhibitor concentration which is the same as or even lower than the preceding one. The same is true for consecutively lower pH and/or consecutively higher concentration of carbohydrates.

In certain embodiments, the mutant strains obtained by this process are more tolerant to acetic acid, formic acid, 2-furaldehyde, 2-furoic acid, vanillin or hydroxybenzoic acid or a combination thereof. Exemplary processes were described in the parent provisional application and a subsequent thesis defense presentation entitled "Development of Acetic-acid Tolerant *Zymomonas mobilis* Strains through Adaptation", by Yun Wang in partial fulfillment of the requirements for the Master of Science in chemical and biomolecular engineering degree to Georgia Institute of Technology on Apr. 24, 2008 which for purposes of U.S. patent practice are fully incorporated herein by reference to the extent they are not inconsistent with the instant application.

Advantageously, the methods of the present invention may be conducted without employing mutagenesis like NTG mutagenesis. Likewise, the methods do not require a continuous reactor and/or long periods of time. Instead, the methods may be employed in smaller volumes like test tubes to yield faster results. The isolated mutant strains of the present invention may be capable of shorter lag times, higher specific growth rates, and/or high ethanol conversion from multiple biomass sugars even in the presence of harsh conditions (e.g., inhibitors or extreme pH or temperature).

Any suitable medium known in the art can be used for growing the Z. mobilis strain. In certain embodiment, the medium used in the process is a seed medium or RM medium comprising glucose, yeast extract and monobasic potassium phosphate. In certain embodiment, the medium contains 20 g/L glucose, 10 g/L yeast extract, 2 g/L monobasic potassium phosphate. This medium is sometimes referred to as RM medium and may be modified to contain other amounts of glucose or other carbohydrates.

The acetic acid tolerant mutant strains are developed by sequentially culturing the Z. mobilis strain in the medium in presence of consecutively higher concentrations of acetic acid. In certain embodiments, the sequential culturing of the Z. mobilis strain is carried out in the medium comprising acetic acid at a concentration less than about 2%. In other embodiments, the concentration of acetic acid for sequential culturing can range from about 0.1% w/v to about 2% w/v. In certain embodiments, the acetic acid concentration is from about 0.2% to 1.6% w/v. In one embodiment, the acetic acid concentration is about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% or 2.0%.

The pH of the medium can be adjusted by sodium hydroxide (50% w/v). In certain embodiments, the pH is about 6 to 6.5.

The procedure of adaptive mutation for inhibitors is illustrated in the FIG. 1, using the first round adaptation as an example. In the first step, Z. mobilis (ZM4) strain is grown in RM medium in the absence of acetic acid at pH 6.0 and 30° C. without shaking. After overnight growth, the Z. mobilis is inoculated into a new culture tube containing RM-acetate medium supplemented with acetic acid concentration. In one embodiment, the concentration of acetic acid is about 0.05%, 0.1%, 0.15% or 0.2%.

In one embodiment, the initial O.D. value is 0.01. The culture is then incubated under the same condition as above until the O.D. value reaches 0.1. An aliquot of culture is inoculated into a new culture tube containing the same but fresh RM-acetate medium to an O.D. of 0.01, and the cells are allowed to grow. Once O.D. reaches 0.1, a new culture is started. The cycle can be repeated several times until the O.D. of the twenty-four hour culture reaches a constant value. The culture from the last cycle is then plated on an agar plate containing the same concentration of acetic acid as the liquid medium.

Single colonies on the agar plates can be screened based upon various parameters. In one embodiment, these parameters are: the specific growth rate, biomass concentration (24 hours) and ethanol concentration (24 hours).

The specific growth rate can be determined by methods known to one of skill in the art. In one embodiment, the specific growth rate is determined from the plots of optical density (OD) vs. time, as described in the Examples section.

A mutant adapted to the highest acetic acid concentration of the round (in this case, 0.2%) is then used as the parent strain in the next round adaptation with an increment increase of acetic acid concentration. The process of sequential culturing at consecutively higher concentrations of acetic acid can be repeated at least once. In certain embodiments, the process can be repeated at least 2, 3, 4, 5 or more times. The acetic acid concentration in the culture medium can be increased by increments of at least about 0.05%. In certain embodiments, the acetic acid concentration is increased by about 0.05, 0.1, 0.15, 0.2, 0.25 or 0.3%.

A plurality of rounds of adaptation mutation can be run, generating several useful tolerant strains. In certain embodiment, the acetic acid tolerant mutant strain developed by adaptation to increasing concentrations of acetic acid may be further optimized by sequentially culturing the mutant strain in a medium comprising acetic acid by consecutively reducing the pH of the medium; and isolating the mutant strain adapted to the lowest pH. In certain embodiments, the acetic acid tolerant mutant strain obtained as described above can be further developed by consecutively reducing the pH of the medium to about 5.5, 5, 4.5 or 4.

In certain embodiments, the acetic acid tolerant mutant is further improved by chemical mutagenesis, recombinant DNA technology or a combination thereof.

Any chemical mutagen known to one of skill can be used. In certain embodiments, N-methyl N'-nitro N-nitrosoguanidine (NTG) is used to further improve the acetic acid tolerance of the mutant. Suitable procedure for NTG mutagenesis are known to one of skill in the art. An exemplary procedure is described by Rogers et al. In this procedure, first, a culture of Z. mobilis strain is treated with NTG. Following NTG mutagenesis, the cultures are plated on agar plates containing different concentrations of acetic acid (e.g., 1.0%, 1.2%, 1.4% and 1.6%) and at different pHs (e.g., 5.0, 5.5 and 6.0). Finally, the culture is plated to isolate the acetic acid tolerant mutant.

Figure 2:
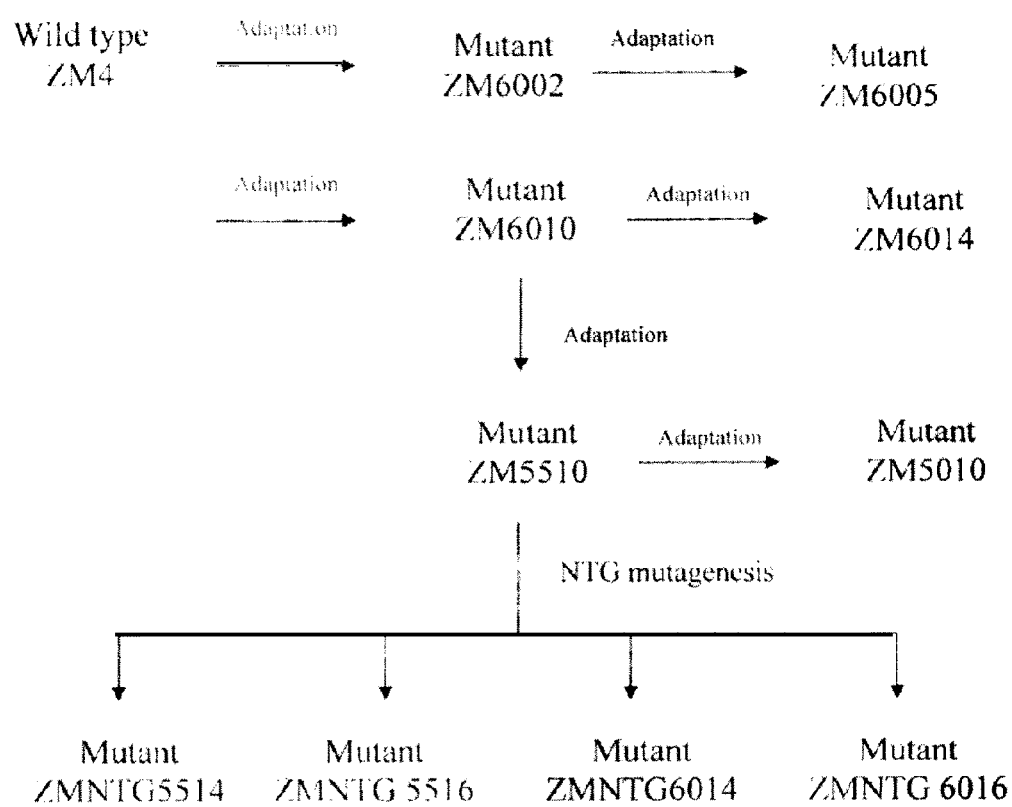
FIG. 2 illustrates an exemplary sequence of mutation.

An exemplary sequence of mutations and the interrelations of the mutants obtained are shown in FIG. 2. In the figure, the mutants obtained are named using a combination of letters and numbers. The letters "ZM" are taken from the name of the microorganism "Z. mobilis". The first two numbers following "ZM" denote the pH used in the adaptation and the last two numbers indicate the acetic acid concentration in percentage. For example, ZM6002 is a strain obtained using adaptation conditions, pH 6.0, and 0.2% acetic acid concentration.

In certain embodiment, the acetic acid tolerant mutant is further improved by recombinant DNA technology. Methods for recombinant DNA technology are known in art. An exemplary methods is described by Baumler et al. in *Applied biochemistry and biotechnology*, 2006. 134: p. 15-26.

Using similar procedures, mutant strains tolerant to other inhibitors can be prepared. The concentrations of various inhibitors in sequential culturing, number of rounds of adaptation and conditions for optimizing the adaptation can be empirically determined by one of skill in the art with reference to the instant application. The most adapted mutant strains can be isolated by screening the single colonies on the agar plates based on various parameters, including, the specific growth rate, biomass concentration and ethanol concentration.

Thus, in certain embodiments, provided herein is process for obtaining a more formic acid tolerant Z. mobilis mutant strain comprising: growing a Z. mobilis strain in a medium substantially free of formic acid; sequentially culturing the Z. mobilis strain in the medium in presence of consecutively higher concentrations of formic acid; and isolating the mutant strain adapted to the highest formic acid concentration.

Also provided is a process for obtaining a more vanillin tolerant Z. mobilis mutant strain using a similar procedure. In certain embodiment, the process comprises growing Z. mobi-

*lis* strain in a medium substantially free of vanillin; sequentially culturing the *Z. mobilis* strain in the medium in presence of consecutively higher concentrations of vanillin; and isolating the mutant strain adapted to the highest vanillin concentration.

Further provided is a process for obtaining a more hydroxybenzoic acid tolerant *Z. mobilis* mutant strain comprising growing a *Z. mobilis* strain in a medium substantially free of hydroxybenzoic acid; sequentially culturing the *Z. mobilis* strain in the medium in presence of consecutively higher concentrations of hydroxybenzoic acid; and isolating the mutant strain adapted to the highest hydroxybenzoic acid concentration.

In certain embodiment, provided herein is a process for obtaining a more 2-furaldehyde tolerant *Z. mobilis* mutant strain comprising: growing a *Z. mobilis* strain in a medium substantially free of 2-furaldehyde; sequentially culturing the *Z. mobilis* strain in the medium in presence of consecutively higher concentrations of 2-furaldehyde; and isolating the mutant strain adapted to the highest 2-furaldehyde concentration.

In certain embodiment, provided herein is a process for obtaining a more 2-furoic acid tolerant *Z. mobilis* mutant strain comprising: growing a *Z. mobilis* strain in a medium substantially free of 2-furoic acid; sequentially culturing the *Z. mobilis* strain in the medium in presence of consecutively higher concentrations of 2-furoic acid; and isolating the mutant strain adapted to the highest 2-furoic acid concentration.

Further provided is a process for obtaining a more ethanol tolerant *Z. mobilis* mutant strain comprising growing a *Z. mobilis* strain in a medium substantially free of ethanol; sequentially culturing the *Z. mobilis* strain in the medium in presence of consecutively higher concentrations of ethanol; and isolating the mutant strain adapted to the highest ethanol concentration.

In another embodiment, provided herein is a process for obtaining a more hydroxymethylfuraldehyde tolerant *Z. mobilis* mutant strain comprising growing a *Z. mobilis* strain in a medium substantially free of hydroxymethylfuraldehyde; sequentially culturing the *Zymomonas mobilis* strain in the medium in presence of consecutively higher concentrations of hydroxymethylfuraldehyde; and isolating the mutant strain adapted to the highest hydroxymethylfuraldehyde concentration.

In certain embodiment, provided herein is a more acetic acid tolerant *Z. mobilis* mutant strain obtained by growing a *Z. mobilis* strain in a medium substantially free of acetic acid; sequentially culturing the *Z. mobilis* strain in the medium in presence of consecutively higher concentrations of acetic acid; and isolating the mutant strain adapted to the highest acetic acid concentration.

The invention also pertains to a process for making a *Zymomonas mobilis* strain capable of increased carbohydrate fermentation of one or more carbohydrates selected from xylose, arabinose, mannose and mixtures thereof comprising: a) growing a *Zymomonas mobilis* origin strain in a medium comprising glucose b) sequentially culturing the *Zymomonas mobilis* strain in the presence of consecutively higher concentrations of one or more carbohydrates selected from xylose, arabinose, mannose, and mixtures thereof and lower amounts of glucose; and c) isolating a mutant strain capable of increased carbohydrate fermentation of one or more carbohydrate selected from xylose, arabinose, mannose and mixtures thereof.

The steps are similar to those described above for increasing inhibitor tolerance except that increasing amounts of one or more carbohydrates selected from xylose, arabinose, mannose, and mixtures thereof are employed in conjunction with lower amounts of glucose or no glucose at all in some embodiments. The lower amount of glucose may or may not correspond precisely to the amount of the increase in the carbohydrates selected from xylose, arabinose, mannose, and mixtures thereof. It is preferred that the decrease in glucose generally correspond or are substantially similar to the amount of increase in one or more carbohydrates selected from xylose, arabinose, mannose, and mixtures thereof. For example, the decrease in the concentration of glucose is within about 20, preferably about 10, more preferably 5 percent of the amount of the increase in the carbohydrates selected from xylose, arabinose, mannose, and mixtures thereof. As one example, the sum of the amount of glucose and one or more carbohydrates selected from xylose, arabinose, mannose, and mixtures thereof is 5% (w/v), For example, the sequential culturing may comprise beginning with 5% glucose and 0% xylose, arabinose, mannose followed by 4.75% glucose and 0.25% xylose, arabinose, mannose, or mixture, followed by 4.5% % glucose and 0.5% xylose, arabinose, mannose, or mixture, and so on.

The process of sequential culturing at consecutively higher concentrations of one or more carbohydrates selected from xylose, arabinose, mannose, and mixtures thereof can be repeated at least once. In certain embodiments, the process can be repeated at least 2, 3, 4, 5 or more times. The concentration of xylose, arabinose, mannose, and mixture thereof in the culture medium can be increased by increments of at least about 0.05%. In certain embodiments, the concentration is increased by about 0.1, 0.2, 0.25, or 0.3% with a substantially similar decrease in glucose concentration.

The origin strain may or may not be originally capable of fermenting the one or more carbohydrates selected from xylose, arabinose, mannose, and mixtures thereof. If the origin strain is not capable it may be necessary to genetically modify it so that it is capable capable of fermenting one or more carbohydrates selected from xylose, arabinose, mannose, and mixtures thereof.

The specific nature of the genetic modification may vary depending on the strain and desired outcomes but is not critical so long as the origin strain becomes capable of fermenting the one or more carbohydrates selected from xylose, arabinose, mannose, and mixtures thereof. One suitable method comprises first constructing a suitable plasmid and then transforming the plasmid into the origin strain. For example, to genetically modify a *Zymomonas mobilis* strain incapable of fermenting xylose into a *Zymomonas mobilis* origin strain capable of fermenting xylose a plasmid pZMETX could be constructed and then transformed into the *Zymomonas mobilis* strain incapable of fermenting xylose.

Production of Ethanol Using the Adapted Strains of *Z. mobilis*

In another aspect, provided herein is a process for production of ethanol comprising fermenting a carbohydrate in a biomass in presence of an adapted *Z. mobilis* mutant strain obtained by the process described herein. In certain embodiments, the mutant strains are more tolerant to inhibitors such as ethanol, aliphatic acids, such as acetic acid, formic acid; furan derivatives, such as 2-furaldehyde, 2-furoic acid; and phenolic compounds, such as vanillin and hydroxybenzoic acid. In certain embodiments, the mutant strains are more capable of increased carbohydrate fermentation of one or more carbohydrates that conventional *Zymomonas mobilis* strains such as wild-type strains do not readily ferment. Such carbohydrates may be selected from xylose, arabinose, mannose and mixtures thereof. In certain embodiments, the mutant strains may be both more tolerant to, for example, the aforementioned inhibitors and more capable of increased carbohydrate fermentation.

Any biomass can be used for ethanol production by the process provided herein. Cellulose is the most common form of carbon in biomass, accounting for 40%-60% by weight of the biomass, depending on the biomass source. It is a complex sugar polymer, or polysaccharide, made from the six-carbon sugar, glucose. Hemicellulose is also a major source of carbon in biomass, at levels of between 20% and 40% by weight. It is a complex polysaccharide made from a variety of five- and six-carbon sugars.

The complex polysaccharides in the biomass are converted by hydrolysis to fermentable sugars by treatment with steam, acid, alkali, cellulases or combinations thereof. The sugars are then converted to ethanol by fermentation with the inhibitor resistant or inhibitor tolerant Z. mobilis strains provided herein. In certain embodiments, the sugars comprise glucose, fructose, sucrose, xylose, arabinose, mannose or a mixture thereof.

Suitable fermentation conditions are known in the art. Substrate concentrations of up to about 25% (based on glucose), and under some conditions even higher, may be used. Unlike other ethanol producing microorganisms, no oxygen is needed at any stage for Z. mobilis survival. Also unlike yeast, oxygen does not drastically reduce ethanol productivity or greatly increase cell growth. Agitation is not necessary but may enhance availability of substrate and diffusion of ethanol. Accordingly, the range of fermentation conditions may be quite broad. Likewise, any of the many known types of apparatus may be used for the production of ethanol by the process.

Fermentation can be carried out in a bioreactor, such as a chemostat, tower fermenter or immobilized-cell bioreactor. In certain embodiments, fermentation is carried out in a continuous-flow stirred tank reactor. Mixing can be supplied by an impeller, agitator or other suitable means and should be sufficiently vigorous that the vessel contents are of substantially uniform composition, but not so vigorous that the microorganism is disrupted or metabolism is inhibited.

The fermentation process may be carried out as a batch process or parts or all of the entire process may be performed continuously. To retain the microorganisms in the fermenter, one may separate solid particles from the fluids. This may be performed by centrifugation, flocculation, sedimentation, filtration, etc. Alternatively, the microorganisms may be immobilized for retention in the fermenter or to provide easier separation.

The Z. mobilis mutant strains obtained by the process provided herein may be used as a biologically pure culture or it may be used with other ethanol producing microorganisms in mixed culture. In certain embodiments, preexisting deleterious microorganisms in the substrate are eliminated or disabled before adding the mutant strains to the substrate. In certain embodiment, enzyme(s) are added to the fermenter to aid in the degradation of substrates or to enhance ethanol production. For example, cellulase may be added to degrade cellulose to glucose simultaneously with the fermentation of glucose to ethanol by microorganisms in the same fermenter. Likewise, a hemicellulase may be added to degrade hemicellulose.

In certain embodiment, the process for ethanol production is optimized for maximum ethanol production by various techniques known to one of skill in the art, including, but not limited removal of the inhibitors, for example acetic acid, formic acid, 2-furaldehyde, 2-furoic acid, vanillin and hydroxybenzoic acid, from the pretreated biomass, finding optimum fermentation conditions for the selected mutant strain and others. Exemplary techniques for removal of acetic acid from the pretreated biomass include, but are not limited to use of ion-exchange resins and ion exchange membranes.

In certain embodiments, ethanol production is optimized by finding optimum fermentation conditions for the mutant strain. In one embodiment, this can be achieved by reducing the inhibition of acetic acid on an industrial scale by changing the fermentation conditions, especially for the xylose fermentation, which is more sensitive to acetic acid than glucose fermentation. The fermentation conditions can be optimized by taking into consideration both biomass and sugar utilization.

After fermentation, the ethanol, which may achieve concentrations of up to about 13%, is separated from the fermentation broth by any of the many conventional techniques known to separate ethanol from aqueous solutions. These methods include evaporation, distillation, solvent extraction and membrane separation. Particles of substrate or microorganisms may be removed before ethanol separation to enhance separation efficiency.

Once the fermentation is complete, excess microorganisms and unfermented substrate may be either recycled or removed in whole or in part. If removed, the microorganisms may be killed, dried or otherwise treated. This mixture may be used as animal feed, fertilizer, burnt as fuel or discarded.

Mutant Strains of Z. mobilis Adapted for Enhanced Acetic Acid Inhibition

In one embodiment, the mutant Z.mobilis strains made by the techniques of the present invention, e.g., acetic acid inhibitor tolerant Z.mobilis strains, often have a number of unique characteristics or combinations of unique characteristics. The non-naturally occurring, biologically pure Zymomonas mobilis mutant strain may be characterized by substantially exhibiting one or more of the following characteristics: (1) a lag phase of less than about one day, preferably less than 9 hours; or (2) a specific growth rate of at least about $0.15\ h^{-1}$, preferably at least about $0.3\ h^{-1}$ or (3) an ethanol yield of at least about 95% of theoretical yield; wherein the characteristics are exhibited while fermenting at a pH of about 6 in an RM medium with 50 g/L glucose and 1.6% acetic acid concentration. That is, the initial RM medium before significant colony growth and/or associated fermentation begins comprises 50 g/L glucose and a 1.6% acetic acid concentration and the pH is maintained at about 6. Advantageously, in many instances the one or more characteristics will be exhibited in various other media. These may include initial RM media comprising 20 g/L glucose (or even over a range of from about 20 to about 50 g/L glucose) with a range of from about 0 or from about 1.0 up to about 1.6% acetic acid concentration. In some embodiments the strain substantially exhibits at least 2 or even all 3 of the aforementioned characteristics.

The aforementioned characteristics may be measured by any convenient means including those shown and described in the specific examples below and by reference to the included figures. The lag phase, e.g., the amount of time it takes before appreciable cell growth once placed in the medium, may conveniently be determined by optical density as can specific growth rate.

Advantageously, in some instances an adaptive mutation with respect to the presence of one inhibitor such as acetic acid may also yield improvement to the mutant in one of more of the characteristics even in the presence of one or more additional inhibitors. That is, the techniques of the present invention may yield a mutant which not only exhibits increased acetic acid tolerance, but also, has increased formic acid tolerance.

Mutant Strains of Z. mobilis Adapted for Enhanced Carbohydrate Fermentation

In one embodiment, the mutant Z.mobilis strains made by the techniques of the present invention, e.g., enhanced carbohydrate fermentation Z.mobilis strains, often have a number of unique characteristics or combinations of unique characteristics. The non-naturally occurring, biologically pure Zymomonas mobilis mutant strain may be characterized by substantially exhibiting one or more of the following characteristics: (1) an ethanol yield of at least about 85%, preferably at least about 90% of theoretical yield; or (2) a volumetric ethanol productivity of at least about 0.5, preferably at least about 0.8 grams of ethanol per liter of reactor per hour (g/l/h); or (3) a specific ethanol productivity of at least about 0.9, preferably at least about 0.95 grams per gram of dry cell mass per hour (g/g/h); or (4) a xylose consumption rate of at least about 1.8, preferably at least about 2.0 grams per gram of dry cell mass per hour (g/g/h); or (5) an ability to consume 5% (w/v) xylose in less than about 40 hours, preferably less than about 36 hours; wherein the characteristics are exhibited while fermenting in an RM medium with 50 g/L xylose without glucose. That is, the initial RM medium before significant colony growth and/or associated fermentation begins comprises 50 g/L xylose without significant amounts of glucose. In some embodiments the strain substantially exhibits at least 2, 3, 4, or even all 5 of the aforementioned characteristics.

The aforementioned characteristics may be measured by any convenient means including those shown and described in the specific examples below and by reference to the included figures. The xylose consumption is usually measured from the initial inoculation of the strain into the medium.

Advantageously, in some embodiments one or more of the aforementioned characteristics may be exhibited while fermenting in the absence of any pH control. Advantageously, in some embodiments one or more of the aforementioned characteristics may be exhibited while fermenting at a pH controlled to be about 6.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are better illustrated by the use of the following non-limiting examples, which are offered by way of illustration and not by way of limitation.

EXAMPLES

The following examples are presented to further illustrate and explain the claimed subject matter and should not be taken as limiting in any regard.

Microorganism and Culture Maintenance

Z. mobilis ZM4 (ATCC31821) was obtained from ATCC (American Type Culture Collection). Mutants were developed from the strain by adaptive mutation.

Mutants were developed from the strain by adaptive mutation. Among these mutants, ZM6010, ZM6012, ZM6014, ZM5510 and ZM5010 were chosen for more careful characterization. Mutants ZM6010, ZM6012, ZM6014 were obtained by adaptation at high acetic acid concentration. Mutants ZM5510 and ZM5010 were obtained by adaptation at low pH. Mutants ZMNTG5514, ZMNTG5516, ZMNTG6014 and ZMNTG6014 were developed by NTG mutagenesis from ZM5510.

For long-term storage, all strains were kept at −80° C. in 30% (w/v) glycerol solution by mixing 500 μl sterile medium with culture (overnight cultured) with 500 μl 60% (w/v) glycerol solution in a 1 ml vial. Glycerol solution was prepared by mixing glycerol and deionized water. The 60% glycerol solution was autoclaved at 120° C. for 20 minutes.

Different mediums were needed for different experiments. Seed medium was used for adaptive mutation. Solid medium was used for single colony screening. Fermentation medium was used for mutant characterization.

Seed Medium

The seed medium contained 20 g/L glucose, 10 g/L yeast extract, 2 g/L monobasic potassium phosphate. This medium was known as RM medium. Acetic acid (0.2% to 1.6% w/v) was added when necessary. Sodium hydroxide (50% w/v) was used to adjust the pH of liquid medium. This medium was then sterilized by filtration using a 0.22 μm filter.

Fermentation Medium

Fermentation medium was RM medium based with increased glucose concentration to 50 g/L. Acetic acid concentration varied from 0.2%-1.6%. pH of medium adjusted by sodium hydroxide (50% w/v). The medium was sterilized by filtration using a 0.22 μm filter.

Medium for Other Inhibitors Experiments

The same fermentation medium was used except inhibitors were added at different concentrations: vanillin (0.5 g/l, 1 g/l), formic acid (2.68 g/l, 5.37 g/l), hydroxybenzoic acid (3.4 g/l, 6.8 g/l) and furfuryl alcohol (3.89 g/l, 7.7 g/l). The pH of medium was adjusted to 6.0 by sodium hydroxide (50% w/v). The mediums were sterilized by filtration using a 0.22 μm filter.

Solid Medium for Agar Plates

The solid medium was a mixture of 100 ml autoclaved RM medium containing 1.5% agar and 100 ml sterilized RM medium with various amount of acetic acid and sodium hydroxide (50% w/v) for pH adjustment. This mixture was then spread on the agar plate. Each agar plate had around 25 ml liquid medium.

Colony Screening

After plating, single colonies were formed on the agar plates after two days. These single colonies had different sizes. However the difference in size became smaller with increased acetic acid concentration or decreased pH. The number of single colonies on agar plate also decreased with increased acetic acid concentration or decreased pH.

Single colonies with larger size were inoculated to the fermentation medium in 10 ml culture tubes. All culture tubes were put in the incubator and the cells were incubated at 30° C. without shaking. After the optical density (O.D.) value of culture reached 0.1, samples (1 ml) were picked every two hours for O.D. measurement. After one day fermentation, 1 ml sample was taken for ethanol measurement.

Mutant Characterization

The growth of the strains was studied by batch fermentations. The strains were grown in the fermentation medium with three different pHs (5.0, 5.5, and 6.0) and several acetic acid concentrations (0.0%, 1.0%, 1.4%, and 1.6%) in 20 ml glass vials. The glass vials were filled fully with medium to form an anaerobic cultivation. The glass vials were placed in a biological incubator. The temperature was kept at 30° C. There was no shaking in this process. The initial O.D. value was always 0.01. 1 ml sample was picked every four hours for both O.D. measurement and ethanol, glucose measurement.

Analytical Methods
Optical Density (O.D.)
O.D. value of the sample was measured by Beckman spectrophotometer DU530 at 600 nm. Specific growth rate was determined from the plots of optical density (OD) vs. time.

Ethanol Measurement
The concentrations of ethanol, glucose and acetic acid were measured using an HPLC method (Agilent 1100 HPLC).

Example 1

Adaptive Mutation by Increasing Acetic Acid Concentration

The procedure of adaptive mutation is illustrated in the FIG. 1, using the first round adaptation as an example. In the first step, Z. mobilis (ZM4) strain was grown in RM medium in the absence of acetic acid at pH 6.0 and 30° C. without shaking. After overnight growth, the Z. mobilis was inoculated into a new culture tube containing RM-acetate medium supplemented with acetic acid concentration (0.05%, 0.1%, 0.15%, and 0.2%). The initial O.D. value was 0.01. The culture was then incubated under the same condition as above until the O.D. value reached 0.1. An aliquot of culture was inoculated into a new culture tube containing the same but fresh RM-acetate medium to an O.D. of 0.01, and the cells were allowed to grow. Once O.D. reached 0.1, a new culture was started. The cycle repeated several times until the O.D. of the twenty-four hour culture reached a constant. The culture from the last cycle was then plated on an agar plate containing RM medium (pH=6.0) and 0.2% acetic acid. Twelve of the largest colonies were selected for further study. The selected twelve colonies were screened based upon, growth rate, cell mass concentration (O.D. obtained after 24 hour cultivation), and ethanol concentration (5% glucose and 24 hours cultivation).

Figure 3:
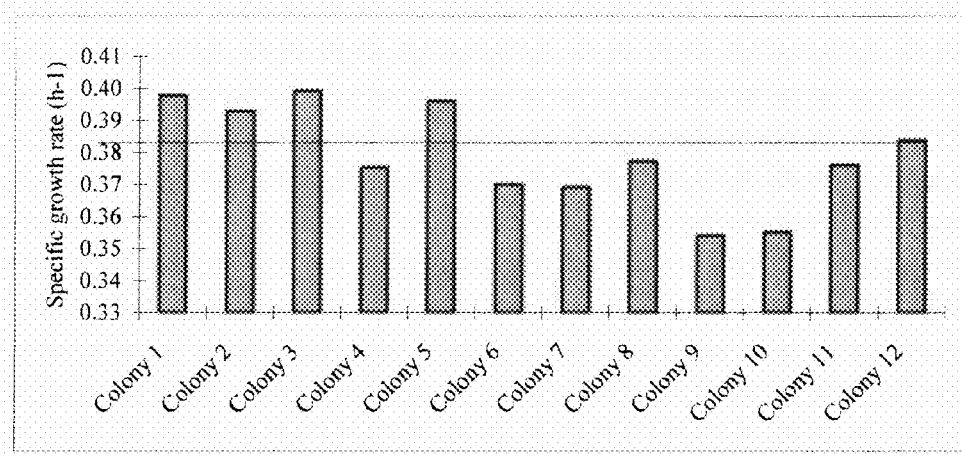
FIG. 3 provides (A) Specific growth rate (B) O.D. value and (C) Ethanol concentration of twelve colonies from adaptive mutation with 0.2% acetic acid (Horizontal lines represent the average of the twelve colonies analyzed.).
Figure 3:
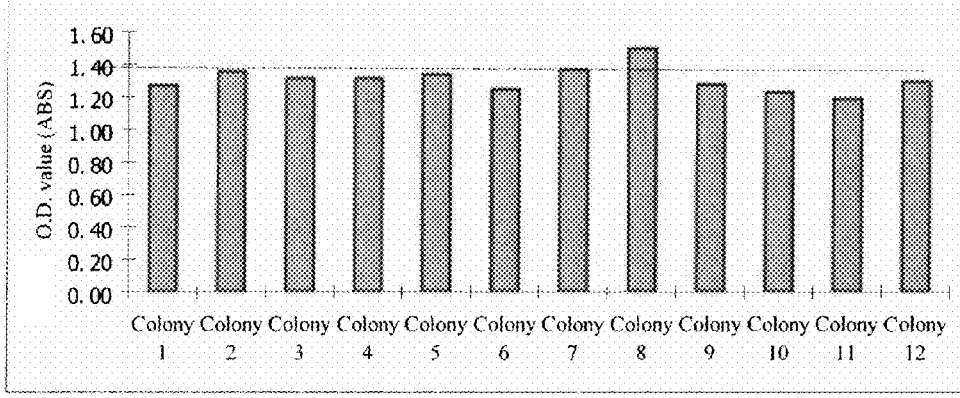
Figure 3:
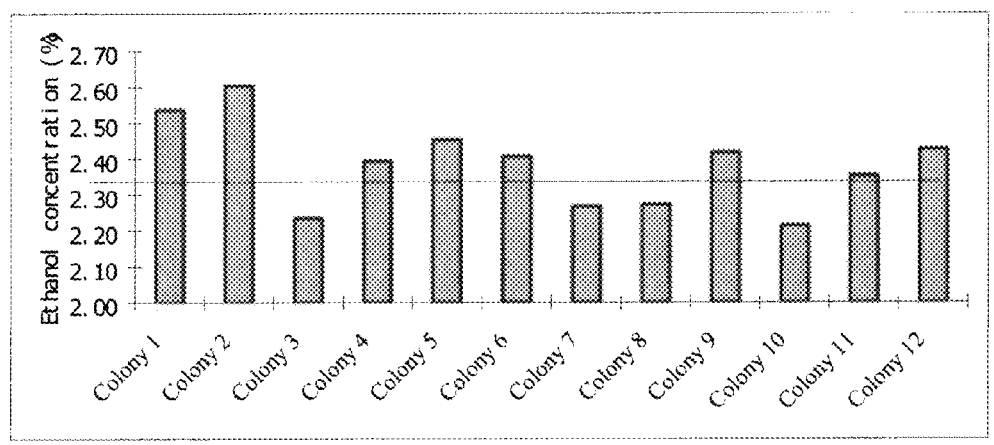

FIG. 3 shows the specific growth rate, the O.D. and ethanol concentration for each colony. The horizontal lines indicate the average value of the 12 colonies. For specific growth rate, the average value was $0.38h^{-1}$. The data showed that colonies 1, 2, 3, 5 had slightly higher specific growth rate than the average.

Biomass concentration (as indicated by O.D. after 24 hours cultivation) of colonies 1, 2, 3, 5 were all in the relatively narrow range of 1.21 to 1.44, so further study was undertaken in order to select the better colonies.

Ethanol concentrations of twelve different colonies after one-day fermentation showed that colony 1 and colony 2 had higher ethanol concentration than other colonies. The glycerol stocks were made for both colonies and stored in the −80° C. freezer. Because both the O.D. value and ethanol concentration were higher for colony 2, compared to colony 1. Colony 2 was selected for further adaptive mutation. This mutant was named ZM6002.

In the next round, with ZM6002 as parental strain, consecutively higher acetic acid concentrations of 0.3%, 0.4%, and 0.5% were used. The increment was increased from 0.05% to 0.1%. The same adaptation procedures were followed as the previous round. At the end of the adaptation, cultures were plated on agar plates containing the respective concentration of acetic acid.

Numerous colonies appeared on the agar plate containing 0.5% acetic acid, indicating successful adaptation to this acetic acid concentration. The twelve largest colonies were selected from the agar plate for screening based upon, growth rate, cell mass concentration (O.D. obtained after 24 hour cultivation), and ethanol concentration (5% glucose and 24 hours cultivation).

Figure 4:
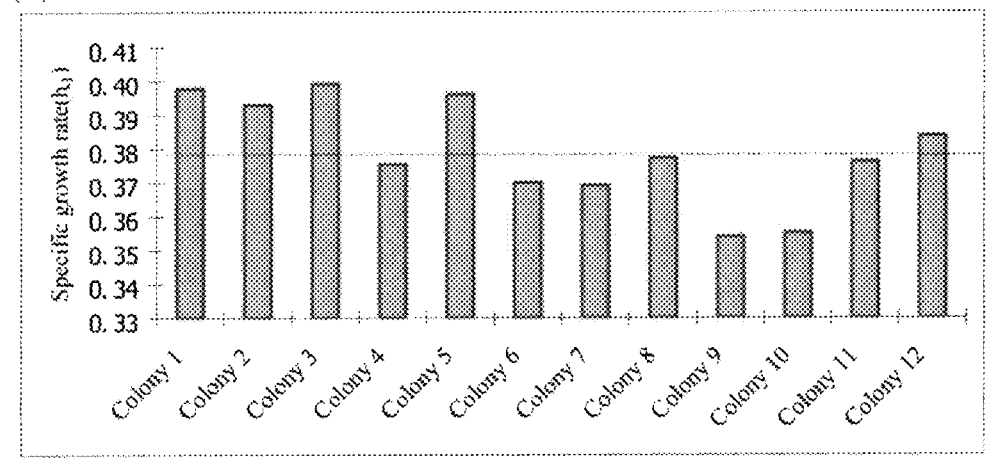
FIG. 4 provides (A) Specific growth rate (B) O.D. value and (C) Ethanol concentration of twelve colonies from adaptive mutation with 0.5% acetic acid (Horizontal lines represent the average of the twelve colonies analyzed.).
Figure 4:
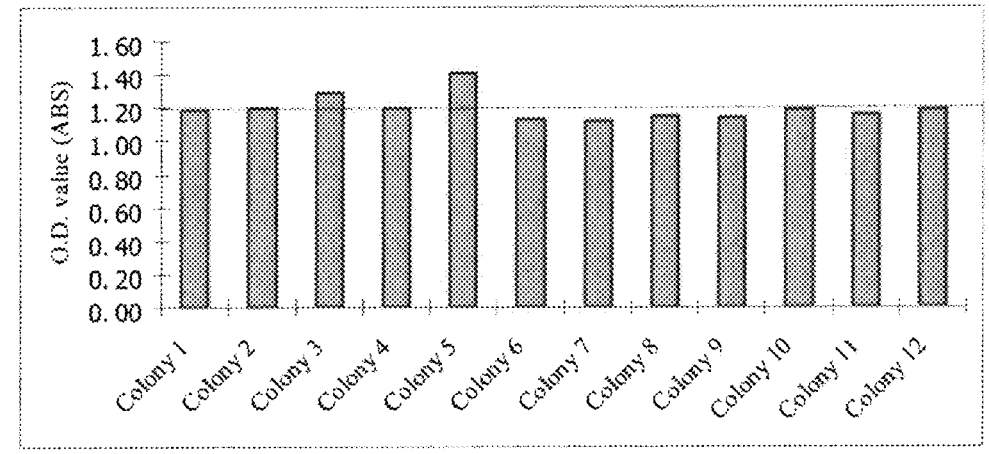
Figure 4:
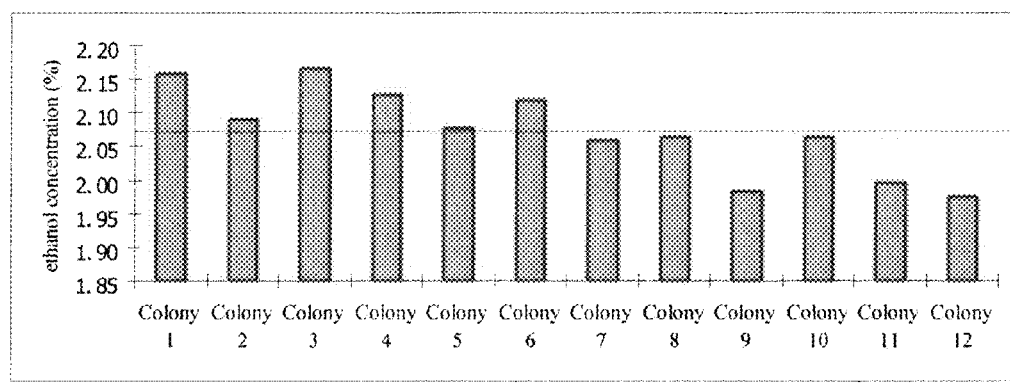

FIG. 4 shows the specific growth rate, O.D. and ethanol concentration of each colony. For specific growth rate, the average value was $0.38h^{-1}$. The data showed that colonies 1, 3, 5 had slightly higher specific growth rates than average.

However the ethanol concentration of colony 5 was lower than colony 1 and 3 and the biomass concentration of colony 3 was a slightly higher than colony 1. So colony 3 was selected for further adaptive mutation, this mutant was named ZM6005. The glycerol stocks were made for this mutant and stored in a −80° C. freezer.

In the third round, mutant ZM6005 was adapted in the RM-acetate medium with 0.6%, 0.7%, 0.8%, 0.9% and 1.0% acetic acid. The increment of 0.1% was kept because this worked well in the last round. The same adaptation procedures were followed. After plating the culture on agar plate with respective acetic acid concentration, single colonies were formed on the agar plate containing 1.0% acetic acid, indicating successful adaptation to 1.0% acetic acid. Thirteen biggest colonies were selected from the agar plate (1.0% acetic acid) for screening based upon, growth rate, cell mass concentration (O.D. obtained after 24 hour cultivation), and ethanol concentration (5% glucose and 24 hours cultivation).

Figure 5:
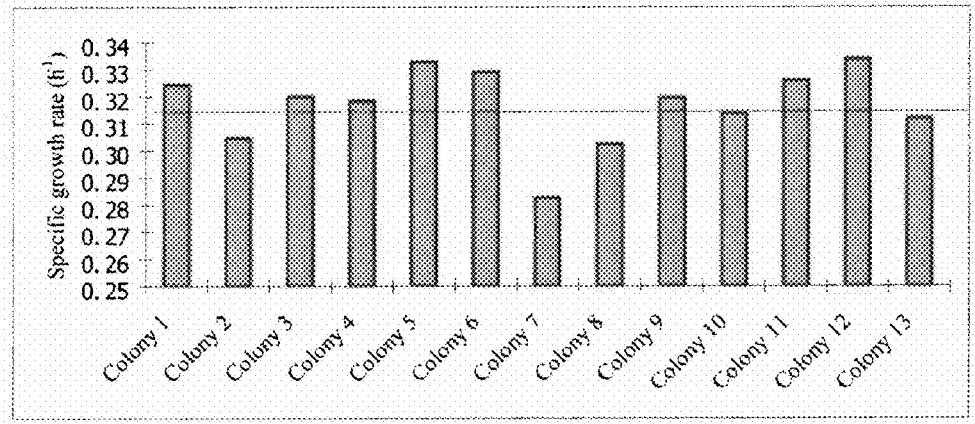
FIG. 5 provides (A) Specific growth rate (B) O.D. value and (C) Ethanol concentration of thirteen colonies from adaptive mutation with 1.0% acetic acid (Horizontal lines represent the average of thirteen colonies analyzed.).
Figure 5:
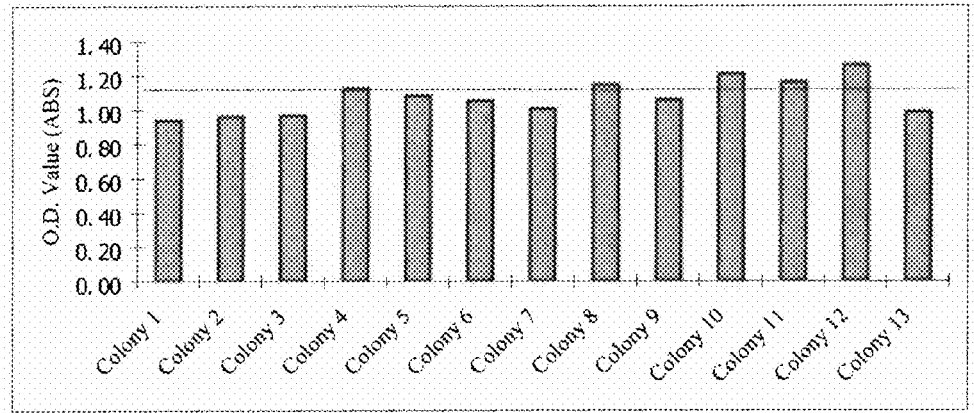
Figure 5:
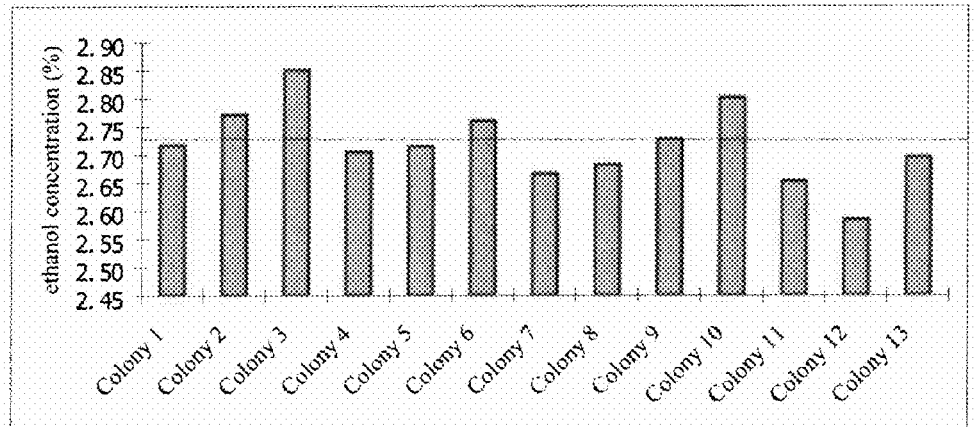

FIG. 5 shows the specific growth rate, O.D. and ethanol concentration of each colony. Based on these three parameters, colony 5 was picked for further adaptive mutation. This mutant was named ZM6010. The glycerol stocks were made for this colony and stored in the −80° C. freezer.

In the fourth round, mutant ZM6010 was adapted to acetic acid concentration 1.2%, 1.4% and 1.6%, respectively. The increment of 0.2% acetic acid concentration was used. Other conditions for adaptation remained unchanged. After plating, single colonies were formed only on agar plates containing 1.2% and 1.4% acetic acid, indicating successful adaptation to 1.2% and 1.4% acetic acid concentration, but not for 1.6% acetic acid. Single colonies from plates containing 1.2% and 1.4% were screened, because they appeared to tolerate higher acetic acid concentration than reported ZM4 in the literature, which was only 1.17%. As the acetic acid increased, adapted strains became more difficult to grow on the agar plate. There were only six big colonies on the plates containing 1.2% and 1.4% acetic acid. These colonies were subjected to the same screening procedure as the previous rounds.

Figure 6:
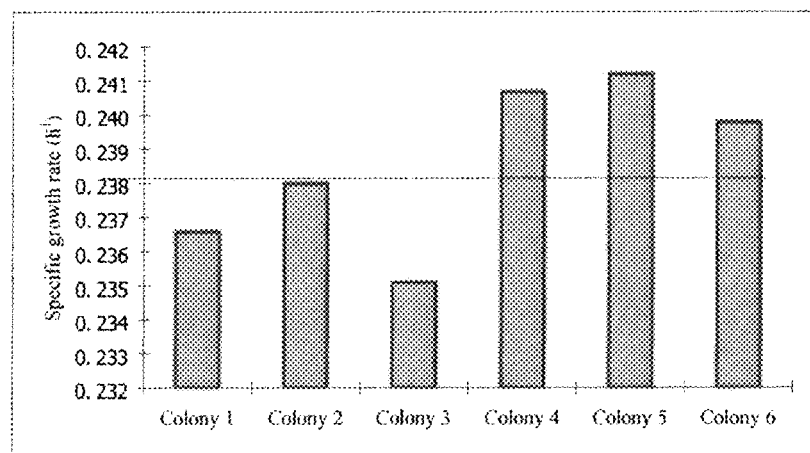
FIG. 6 provides (A) Specific growth rate (B) O.D. value and (C) Ethanol concentration of six colonies from adaptive mutation with 1.2% acetic acid (Horizontal lines represent the average of six colonies analyzed.).
Figure 6:
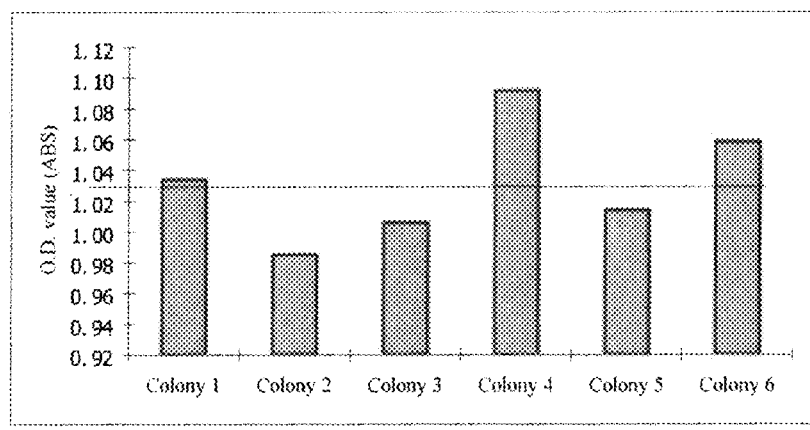
Figure 6:
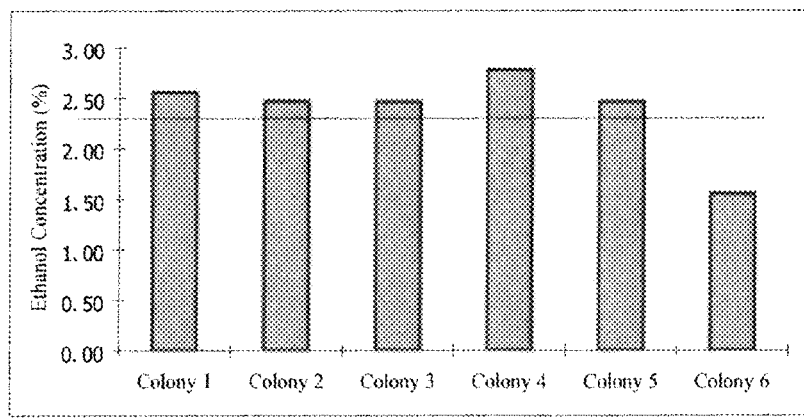

FIG. 6 shows the screening results of the six colonies selected from plate containing 1.2% acetic acid. Based on the three parameters (specific growth rate, O.D. and ethanol concentration), colony 4 was selected for further study. This mutant was named ZM6012. The glycerol stocks were made for this strain and stored in the −80° C. freezer.

Figure 7:
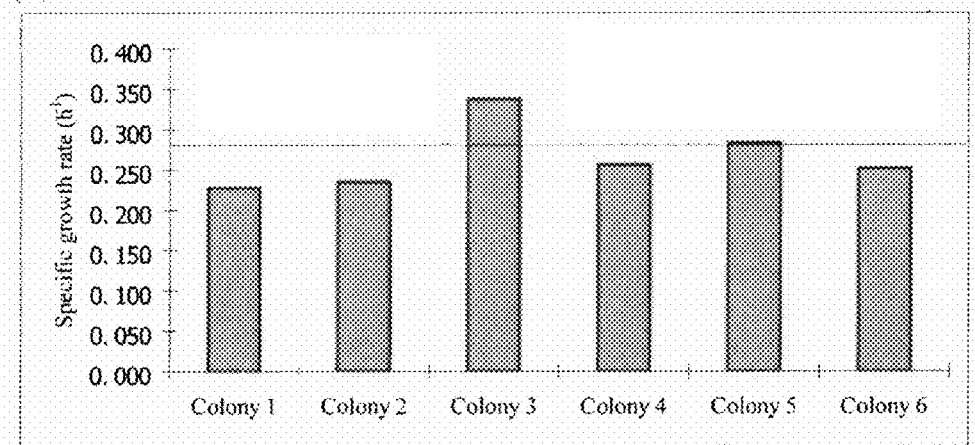
FIG. 7 provides (A) Specific growth rate (B) O.D. value and (C) Ethanol concentration of six colonies from adaptive mutation with 1.4% acetic acid (Horizontal lines represent the average of six colonies analyzed.).
Figure 7:
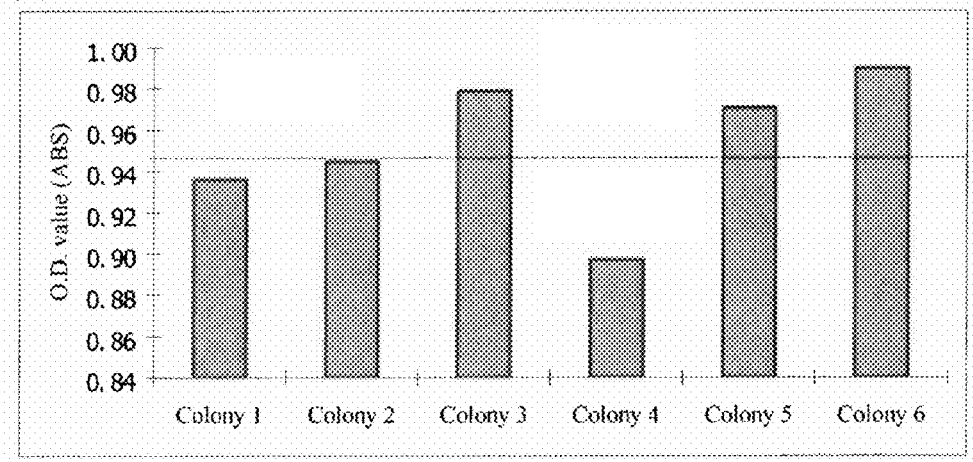
Figure 7:
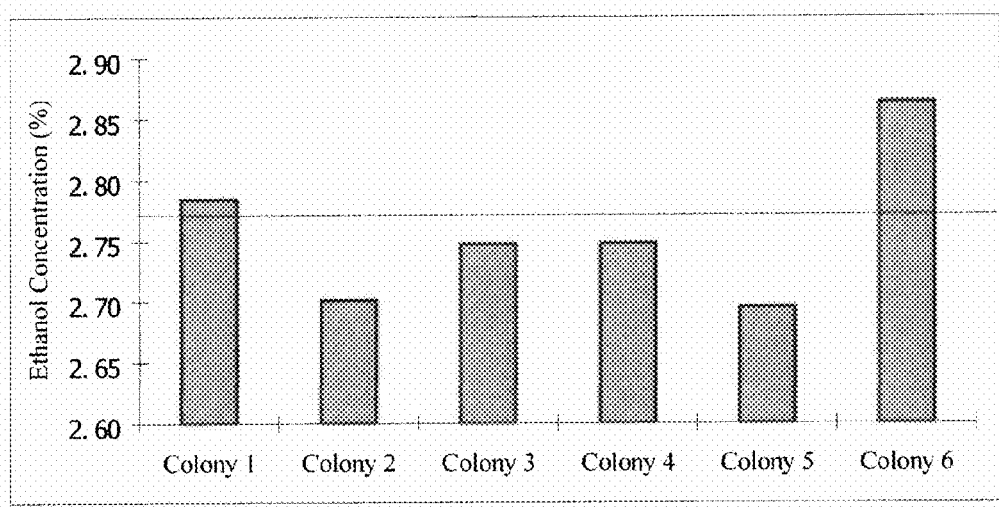

FIG. 7 shows the screening results of the six colonies selected from plate containing 1.4% acetic acid. Based on the screening results, colony 3 was picked for further study. This mutant was named ZM6014. The glycerol stocks were made for this strain and stored in the −80° C. freezer.

In summary, an adaptation procedure was developed. Four rounds of adaptation mutation were successfully carried out. Acetic acid tolerant mutants were successfully developed using the adaptation method. The most adapted mutant tolerated 14 g/l acetic acid.

It was observed that as acetic acid concentration increases, the specific growth rate and final O.D. decrease, reflecting the inhibitory effects of the acetic acid on cell growth, and final cell yield.

The ethanol yield, however, are rather constant, close to theoretical yield. Variations were observed, sometime over 100% theoretical yield, most likely due to the variations of initial glucose concentrations.

Example 2

Adaptive Mutation by Reducing pH

The previous rounds of adaptation in example 1 were carried out at pH 6.0. In an attempt to generate better mutants, adaptation was also performed at lower pH. Mutant ZM6010 was chosen as the starting point because it was adapted with 1.0% acetic acid, which was an intermediate acetic acid concentration.

This adaptation was carried out in essentially same way as previous rounds described in Example 1, except the pH was lowered to 5.5. After adaptation, single colonies were obtained, and were subjected to the same screening procedure as previous rounds.

Figure 8:
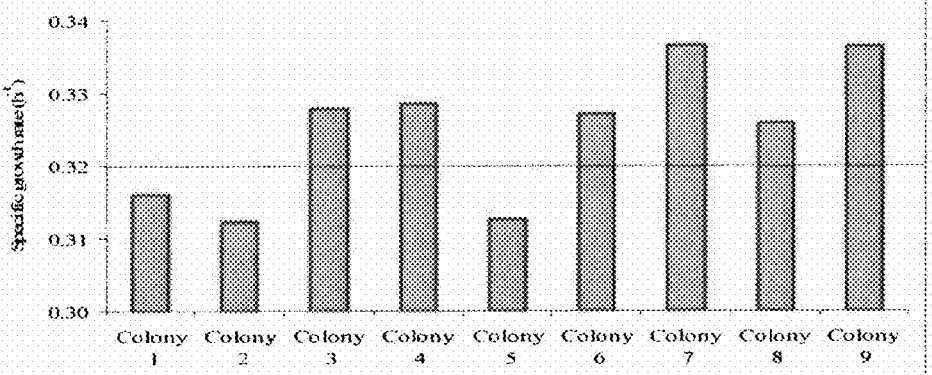
FIG. 8 provides (A) Specific growth rate (B) O.D. value and (C) Ethanol concentration for nine colonies from adaptive mutation at pH 5.5 in the presence of 1.0% acetic acid (Horizontal lines represent the average of nine colonies analyzed.).
Figure 8:
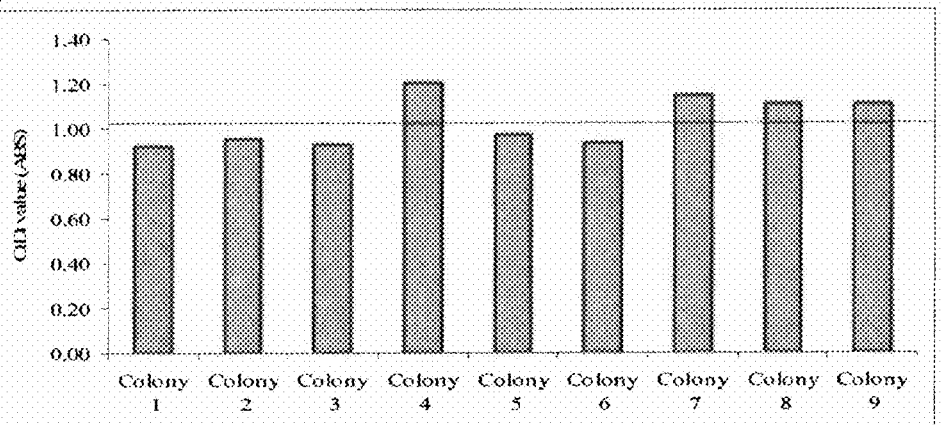
Figure 8:
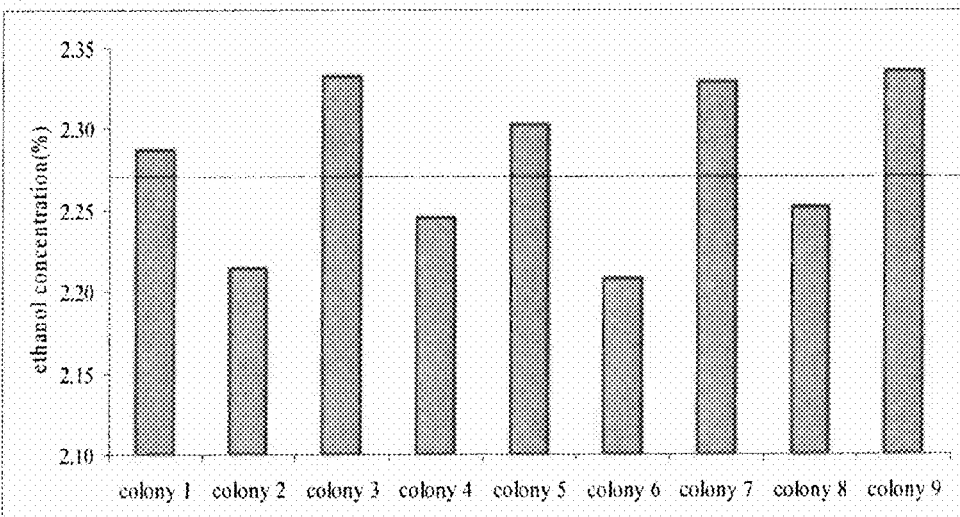

FIG. 8 shows the screening results of the nine colonies selected from plate containing 1.0% acetic acid at pH 5.5. Based upon data presented in FIG. 8, colony 7 was selected for further adaptive mutation. This mutant was named ZM5510. The glycerol stocks were made for this strain and stored in the −80° C. freezer.

Figure 9:
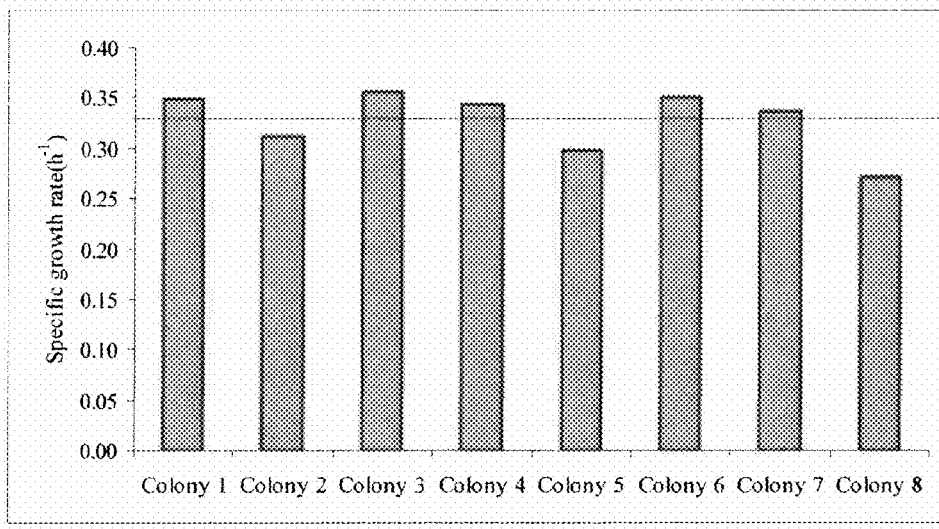
FIG. 9 provides (A) Specific growth rate (B) O.D. value and (C) Ethanol concentration of eight single colonies from adaptive mutation at pH 5.0 in the presence of 1.0% acetic acid (Horizontal lines represent the average of eight colonies analyzed.).
Figure 9:
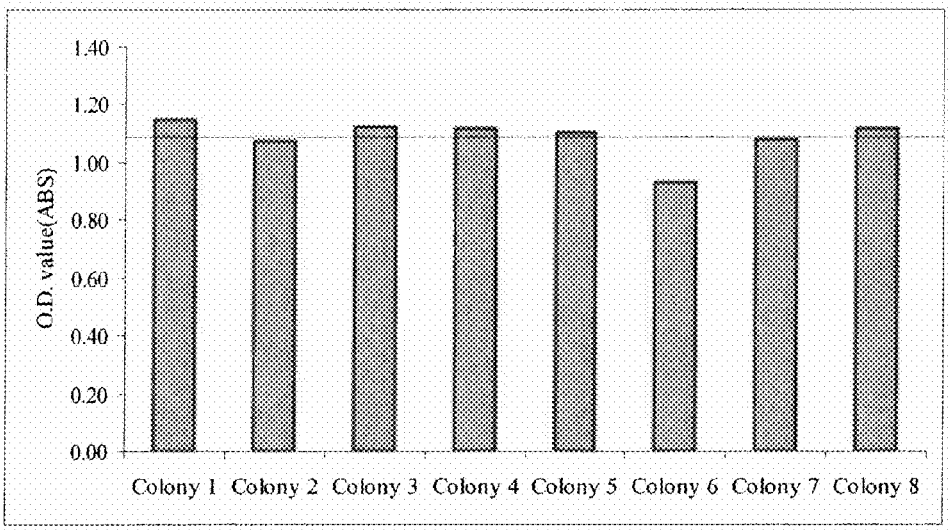
Figure 9:
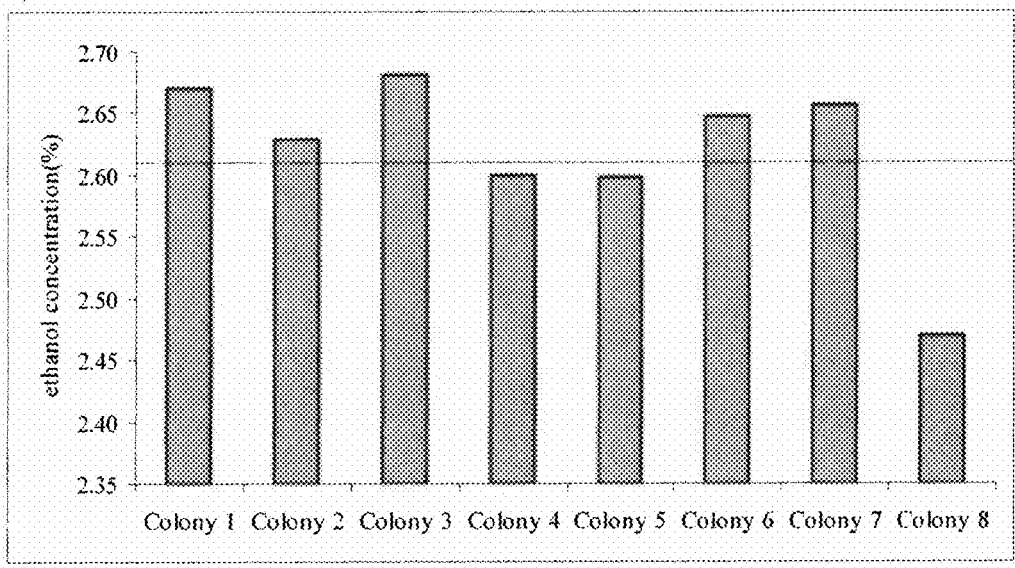

Mutant ZM5510 was further adapted in the medium with 1.0% acetic acid at pH 5.0 FIG. 9 shows the specific growth rate, O.D. value and ethanol concentration after 24 hours fermentation for eight single colonies picked from agar plate at pH 5.0 in the presence of 1.0% acetic acid. Colony 3 was chosen for further investigation, and was named ZM5010. The glycerol stocks were made for this strain and stored in the −80° C. freezer.

Attempts were also made to adapt ZM5510 to higher concentrations of acetic acid (1.2%, 1.4%), and at two pHs (pH 5.0 and pH 5.5). However no single colony grew on the agar plate under these conditions. It appears that, at pH 5.0 and pH 5.5, concentration of 1.0% acetic acid was the limit.

Table 2.1 summarizes mutants obtained so far. "+" means the mutant in this condition was successfully developed. "−" means no mutant was developed in this condition. "x" means no experiment was carried out under this condition.

TABLE 2.1

Summary of the mutants developed by adaptive mutation

| | Acetic acid concentration | | | | | |
|---|---|---|---|---|---|---|
| | 0.2% | 0.5% | 1.0% | 1.2% | 1.4% | 1.6% |
| pH = 6.0 | + | + | + | + | + | − |
| pH = 5.5 | x | x | + | − | − | − |
| pH = 5.0 | X | x | + | − | − | − |

Example 3

NTG Mutagenesis

NTG mutagenesis was used previously by other researchers in an attempt develop acetic acid tolerance. In an attempt to improve the acetic acid tolerance of our mutants, the selected mutant was further treated by NTG mutagenesis. The seed strain was mutant ZM5510. Following NTG mutagenesis as described in chapter 4, the cultures were plated on agar plates containing different concentrations of acetic acid (1.0%, 1.2%, 1.4% and 1.6%) and at different pHs (5.0, 5.5 and 6.0). Single colonies were formed on the agar plates at each acetic acid concentration at pH 5.5 and 6.0. However, single colony was only formed on the solid medium with 1.0% acetic acid concentration at pH 5.0. The colonies were small and it was difficult to tell which one was bigger with naked eyes. There were only a few colonies on each plate, hence, only three or four single colonies were picked for screening.

Figure 10:
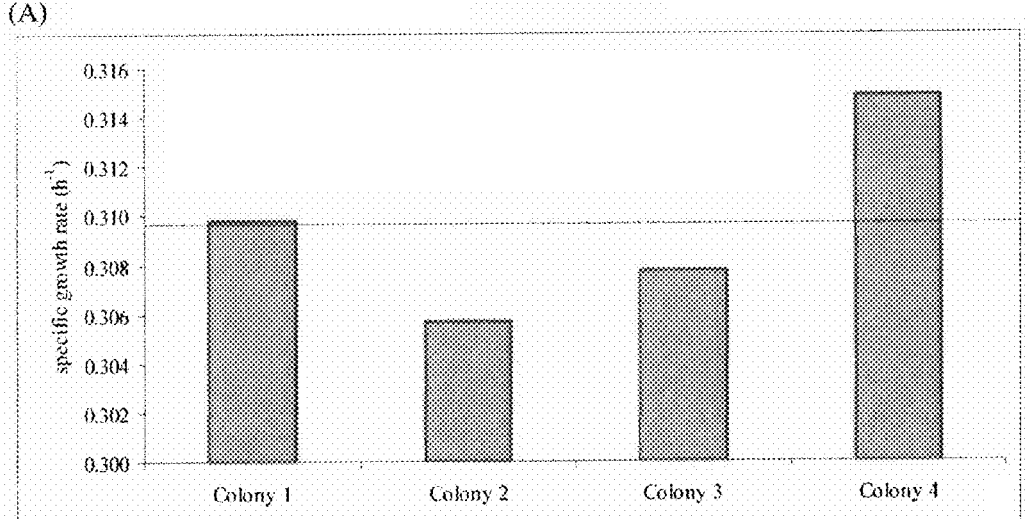
FIG. 10 provides (A) Specific growth rate (B) O.D. value and (C) Ethanol concentration of four single colonies from NTG mutagenesis at pH 6.0 and in the presence of 1.4% acetic acid (Horizontal lines represent the average of four colonies analyzed.).
Figure 10:
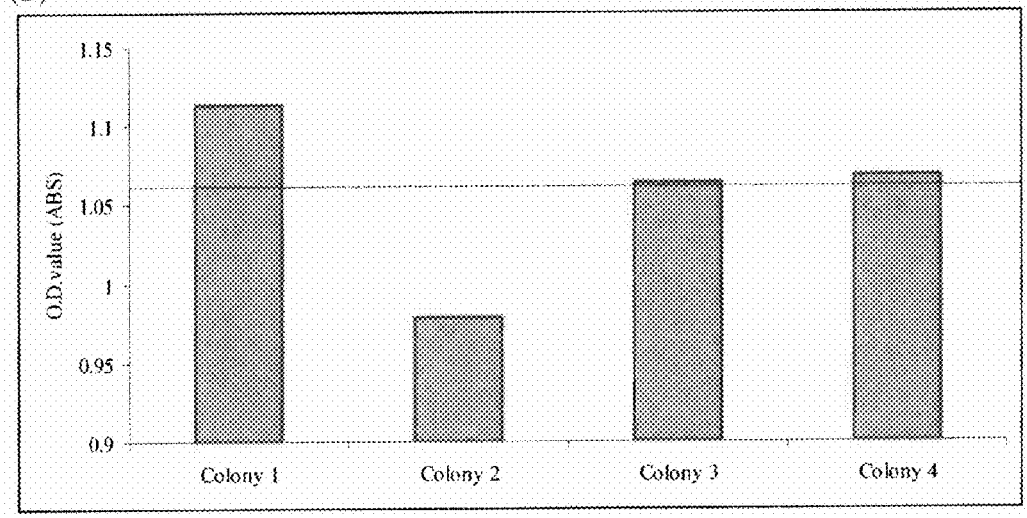
Figure 10:
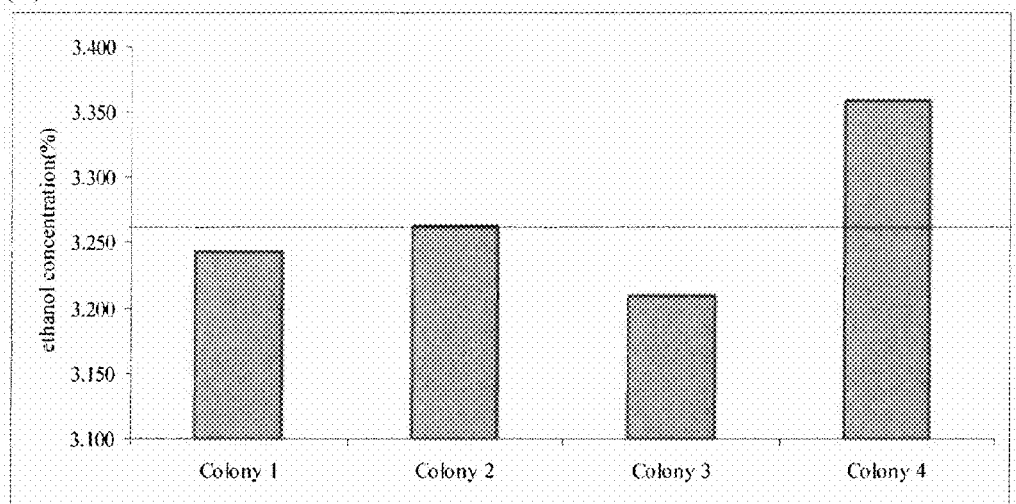

FIG. 10 shows the specific growth rate, O.D. value and ethanol concentration of the four single colonies. The differences between these four candidates were significant. This is because that the NTG mutagenesis is a random mutation. The change inside the strain is complex, so one strain can be significantly different from the other. The same parameters were used to screen the colonies. Colony 4 had a higher specific growth rate and ethanol concentration than average value. And its O.D. value was around the average value, so it was chosen for further investigation. The glycerol stocks were made for this strain and stored in the −80° C. freezer. This mutant was named as ZMNTG6014.

Figure 11:
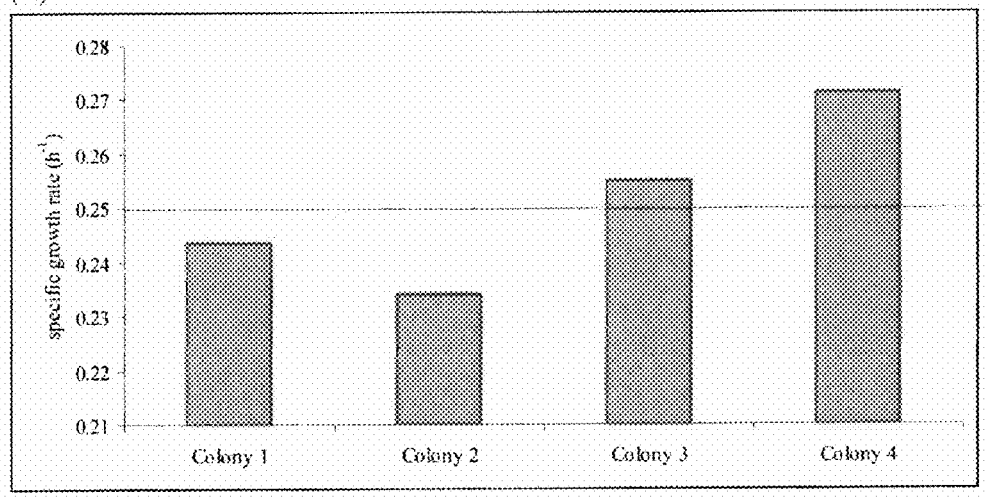
FIG. 11 provides (A) Specific growth rate (B) O.D. value and (C) Ethanol concentration of four single colonies from NTG mutagenesis at pH 6.0 and in the presence of 1.6% acetic acid (Horizontal lines represent the average of four colonies analyzed.).
Figure 11:
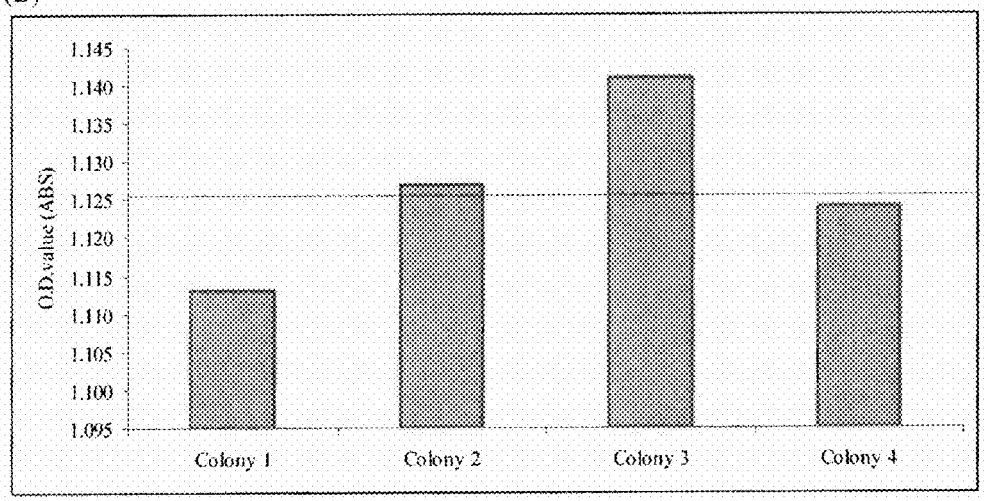
Figure 11:
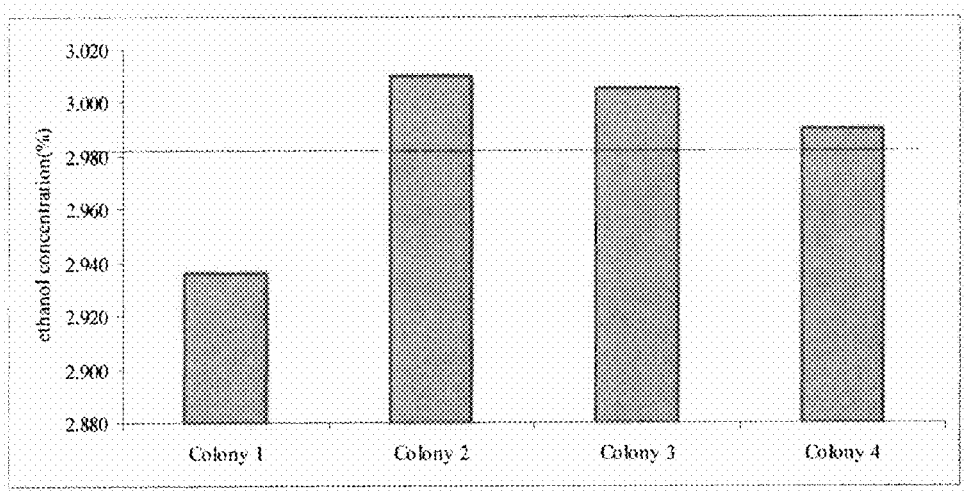

FIG. 11 shows the characteristics of the four single colonies from NTG mutagenesis at pH 6.0 in the presence of 1.6% acetic acid. The performance of these four single colonies was different. Colony 4 had higher specific growth rate than average value. But the other two parameters (O.D. and ethanol concentration) of this colony were around the average value. Colony 3 had the highest O.D. value, which was above the average value. And the ethanol concentration of this colony was also above the average. But its specific growth rate was around the average area. Colony 2 had highest ethanol concentration, which was higher than average, but its specific growth rate and O.D. value were all around the average value. Because the specific growth rate was always thought as the most important parameter, colony 4 was chosen for further investigation. The glycerol stocks were made for this strain and stored in the -80° C freezer. This mutant was named as ZMNTG6016.

Figure 12:
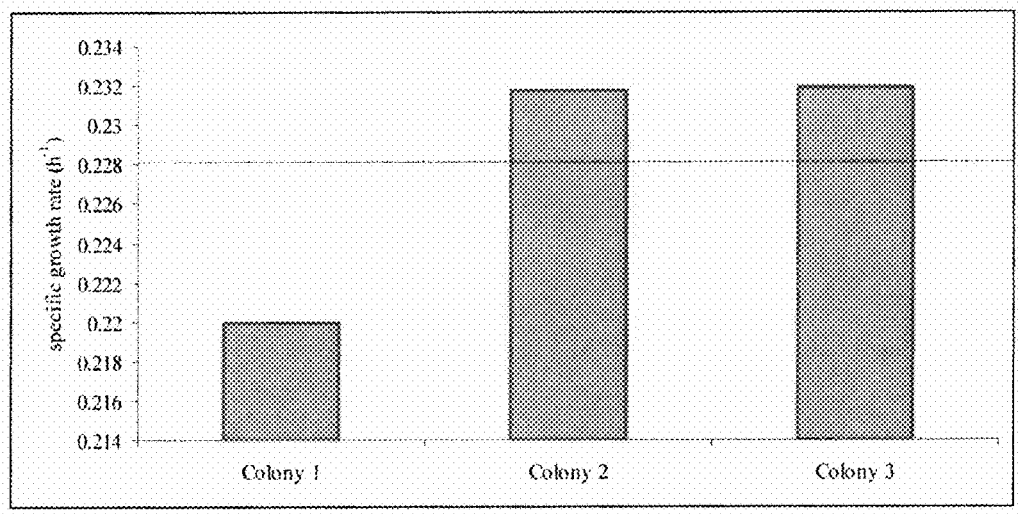
FIG. 12 provides (A) Specific growth rate (B) O.D. value and (C) Ethanol concentration of four single colonies from NTG mutagenesis at pH 5.5 and in the presence of 1.4% acetic acid (Horizontal lines represent the average of three colonies analyzed.).
Figure 12:
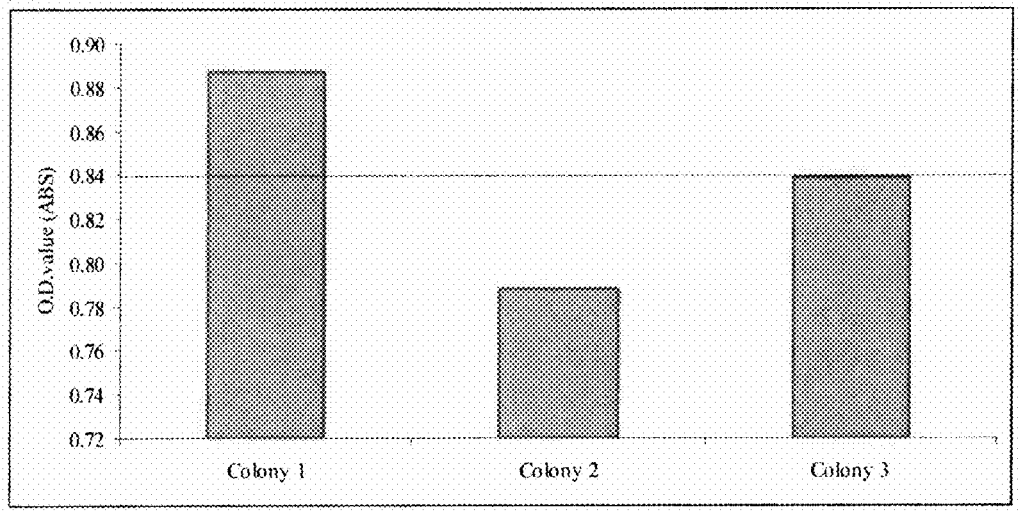
Figure 12:
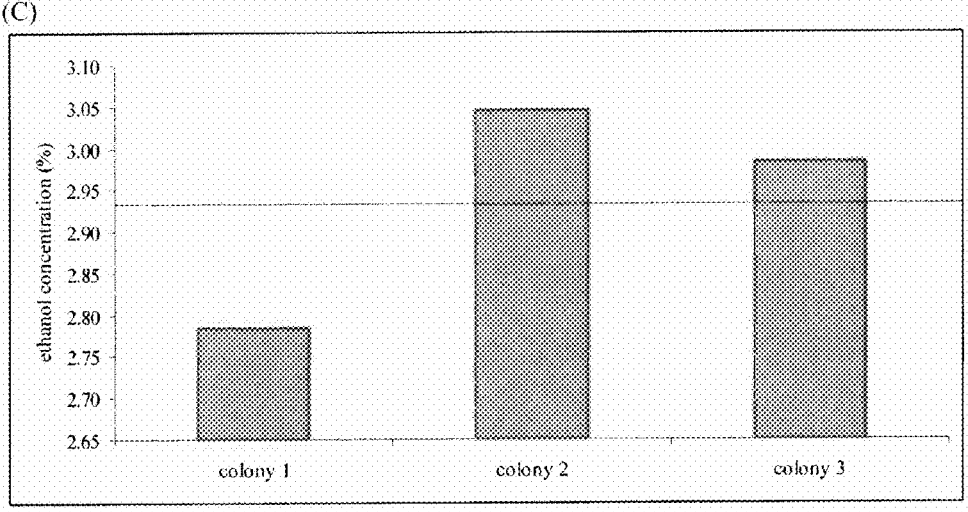

FIG. 12 shows the specific growth rate and O.D. value of three colonies from NTG mutagenesis at pH 5.5 in the presence of 1.4% acetic acid. The specific growth rate of colony 1 was lower than average value, so this strain was not considered further. Colony 2 and colony 3 had almost the same specific growth rate. And the O.D. values of these two colonies were all around the average values. Because the colony 3 had a little higher O.D. value than colon 2, colony 3 was chosen for further investigation and named as ZMNTG5514. However the glycerol stock were prepared for both strains and stored in the −80° C. freezer.

Figure 13:
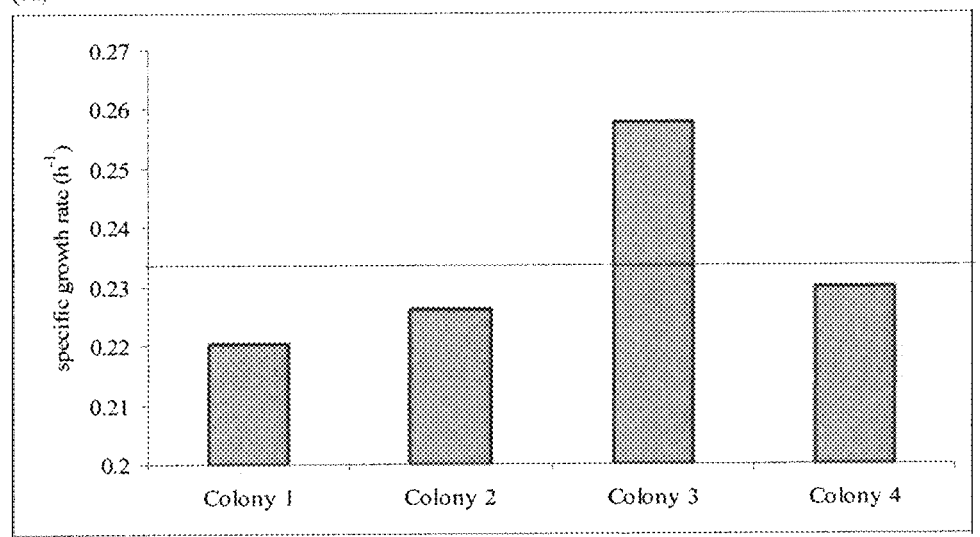
FIG. 13 provides (A) Specific growth rate (B) O.D. value and (C) Ethanol concentration of four single colonies from NTG mutagenesis at pH 5.5 and in the presence of 1.6% acetic acid (Horizontal lines represent the average of four colonies analyzed.).
Figure 13:
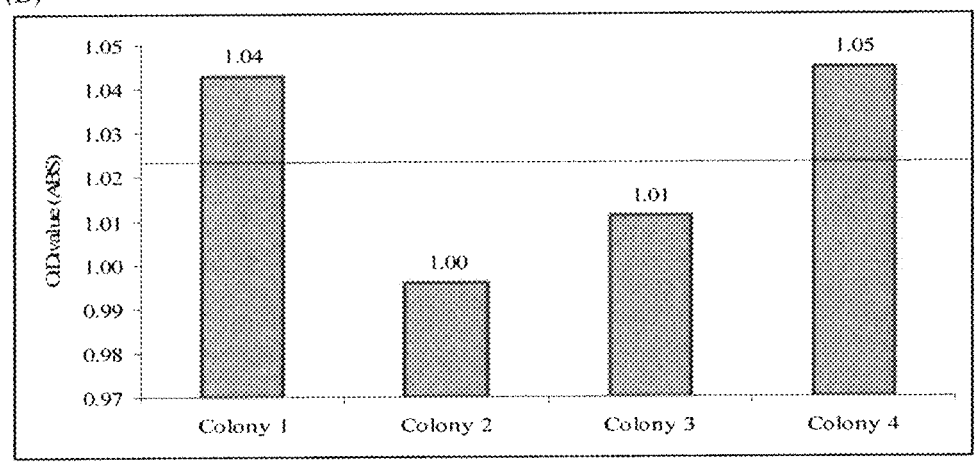
Figure 13:
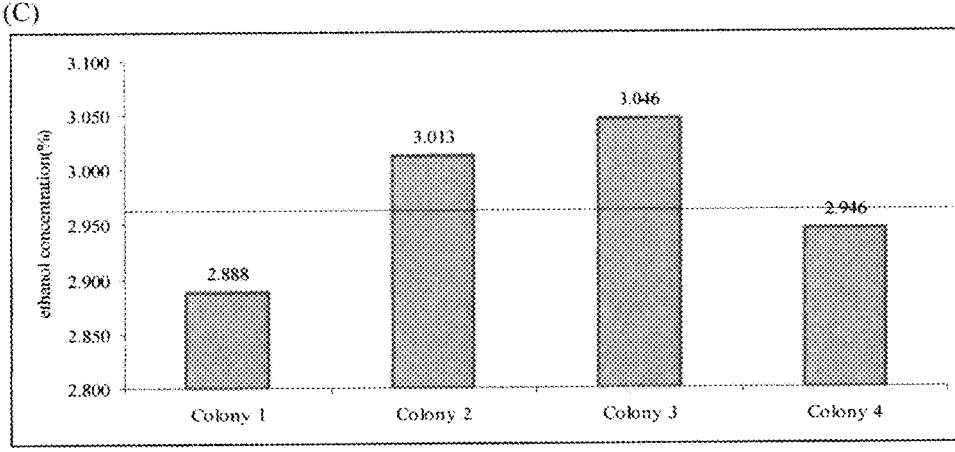

FIG. 13 shows the parameters of the four single colonies from NTG mutagenesis at pH 5.5 in the presence of 1.6% acetic acid. Because of the low pH and high acetic acid concentration, these four single colonies exhibited significant differences. Colony 3 was chosen was chosen for further investigation. The glycerol stocks were made for this strain and stored in the −80° C. freezer. This mutant was named as ZMNTG5516.

Example 4

Figure 14:
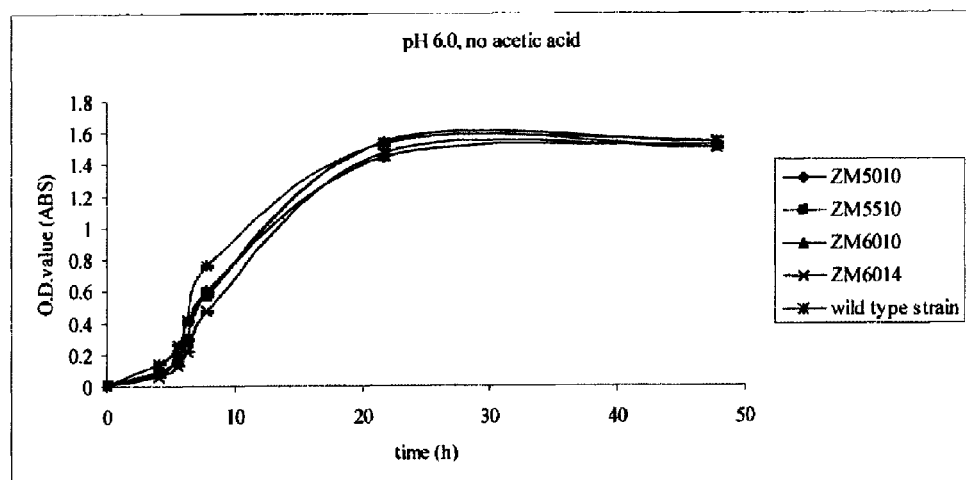
FIG. 14 depicts growth curves at pH 6.0 in the absence of acetic acid.
Figure 15:
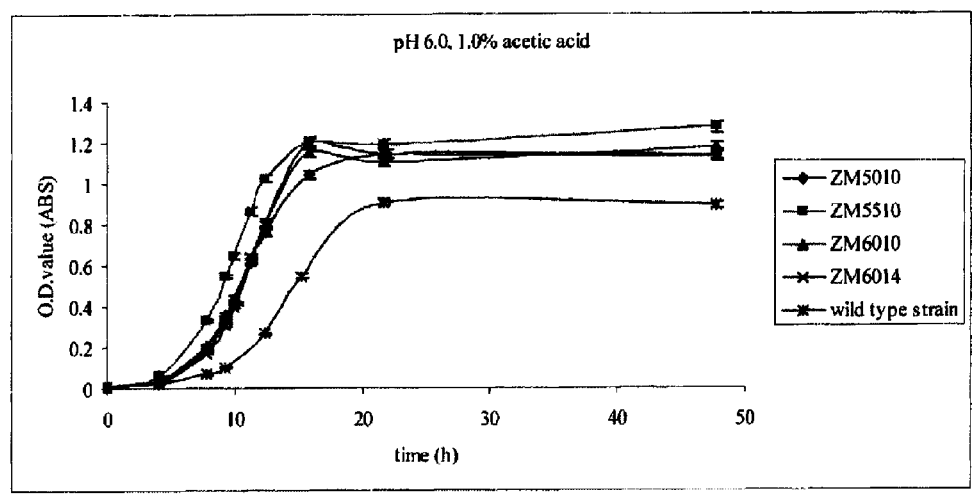
FIG. 15 depicts growth curves at pH 6.0 in the presence of 1.0% acetic acid.

The Characteristics of Original Strain and Mutants Obtained by Adaptive Mutation The specific growth rate, the final cell concentration (represented by O.D.), and the lag phase of mutants ZM6010, ZM6014, ZM5510 and ZM5010 were compared to those of strain. ZM6010 and ZM6014 were the mutants adapted at high acetic acid concentration and ZM5510 and ZM5010 were the mutants adapted at the low pH. The growth curves of these five strains at different acetic acid concentrations and pHs are shown in FIGS. 14 to 15. The lag phase and specific growth rate of these strains under different conditions are summarized in Table 4.1 and 4.2.

FIG. 14 shows the O.D. values of these strains as a function of time at pH 6.0 without acetic acid. Under this condition, the performances of all five strains were quite similar. The lag phase was about 4.1 hours; the specific growth rate was about 0.52 h$^{-1}$; and the final O.D. value was about 1.5. All the strains completed the fermentation within one day.

In the presence of acetic acid, there are significant differences between the mutants and the strain. In the presence of 1.0% acetic acid (FIG. 15), all the strains had longer lag phase and lower specific growth rate compared to the condition in the absence of acetic acid. The original strain had a longer phase, and lower specific growth rate compared to the mutants. The differences between the mutants were small. Under this condition, the lag phase was about 5.0 hours for all mutants, but 7.8 hours for original strain. The specific growth rate of all mutants was about 0.43 h$^{-1}$, but the specific growth rate of original strain was only 0.31 h$^{-1}$. The O.D. of all mutants was still above 1.1, but this value of original strain was lower than 1.0. Both the mutants and the original strain could still complete the fermentation in one day.

Figure 16:
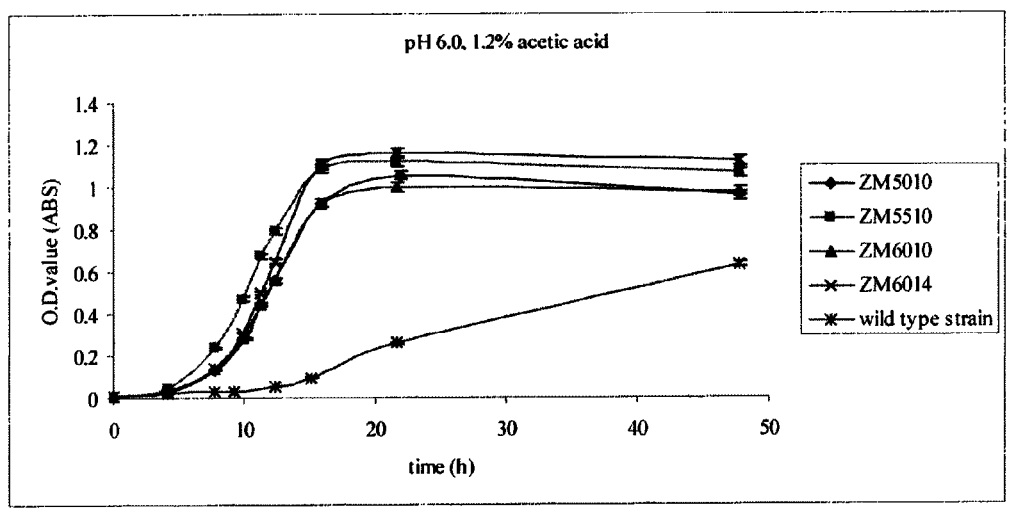
FIG. 16 depicts growth curves at pH 6.0 in the presence of 1.2% acetic acid.

With increasing acetic acid concentration to 1.2% (FIG. 16), the specific growth rate decreased and lag phase increased further for all strains. The difference between the mutants and the original strain became larger. Under this condition, the original strain could not complete the fermentation in two days. The lag phase of original strain increased to 15.2 hours. The specific growth rate of the original strain decreased to 0.151 h$^{-1}$. On the other hand, all the mutants completed the fermentation in one day. The lag phase was about 5.5 hours for all mutants. ZM6014 and ZM5510 had a slightly higher specific growth rate, which was about 0.43 h$^{-1}$, than that of ZM5010 and ZM6010, which was about 0.36 h$^{-1}$. The O.D.s of ZM6014 and ZM5510 were also slightly higher than ZM5010 and ZM6010.

Figure 17:
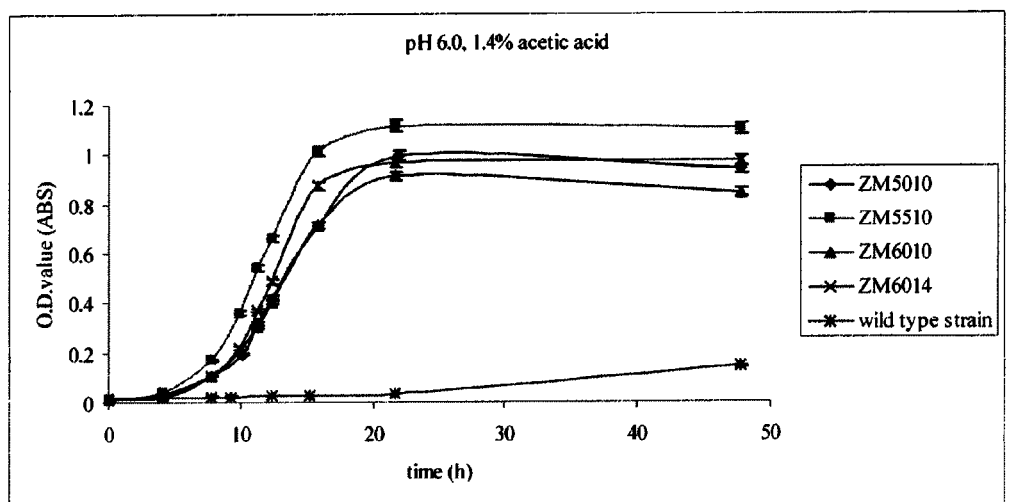
FIG. 17 depicts growth curves at pH 6.0 in the presence of 1.4% acetic acid.
Figure 18:
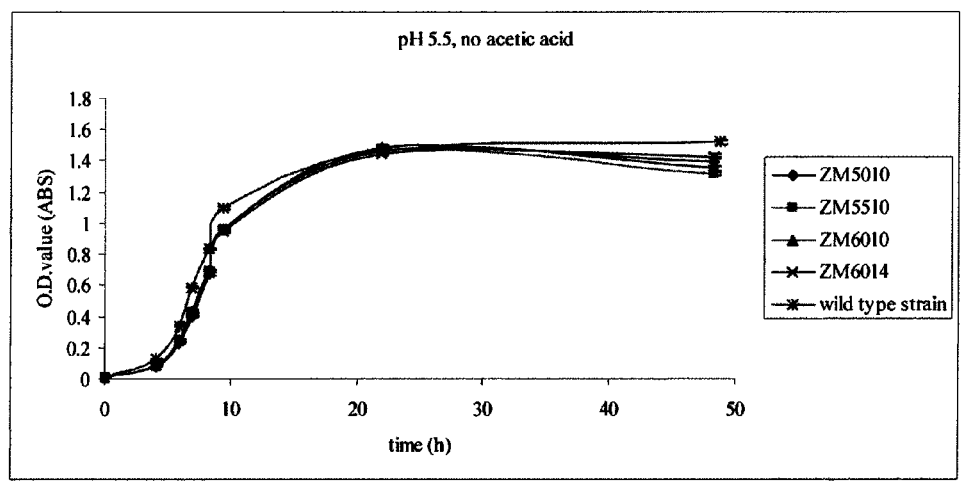
FIG. 18 depicts growth curves at pH 5.5 in the absence of acetic acid.
Figure 19:
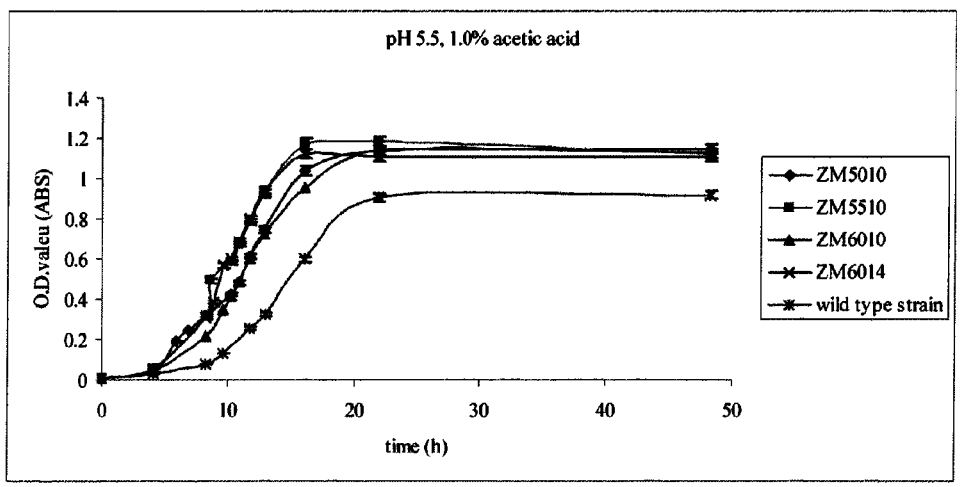
FIG. 19 depicts growth curves at pH 5.5 in the presence of 1.0% acetic acid.
Figure 20:
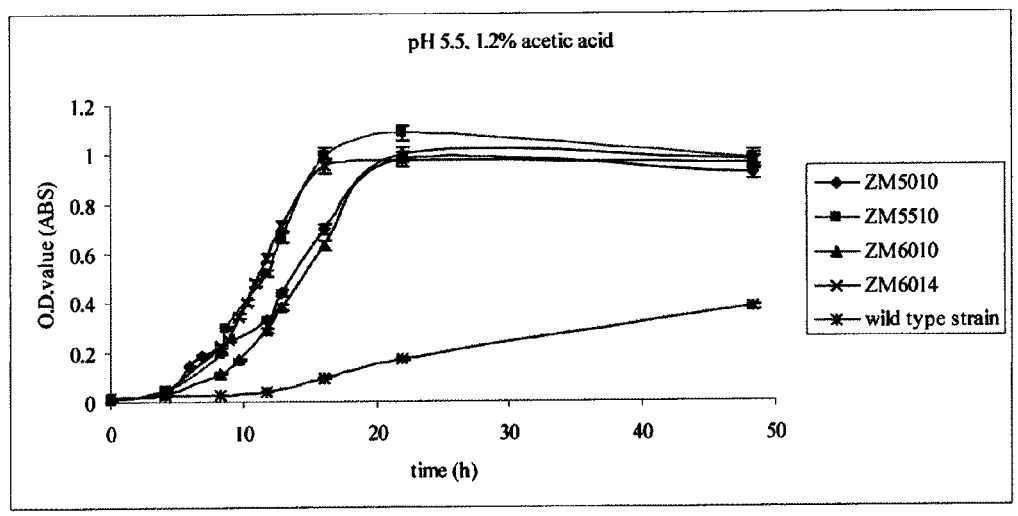
FIG. 20 depicts growth curves at pH 5.5 in the presence of 1.2% acetic acid.
Figure 21:
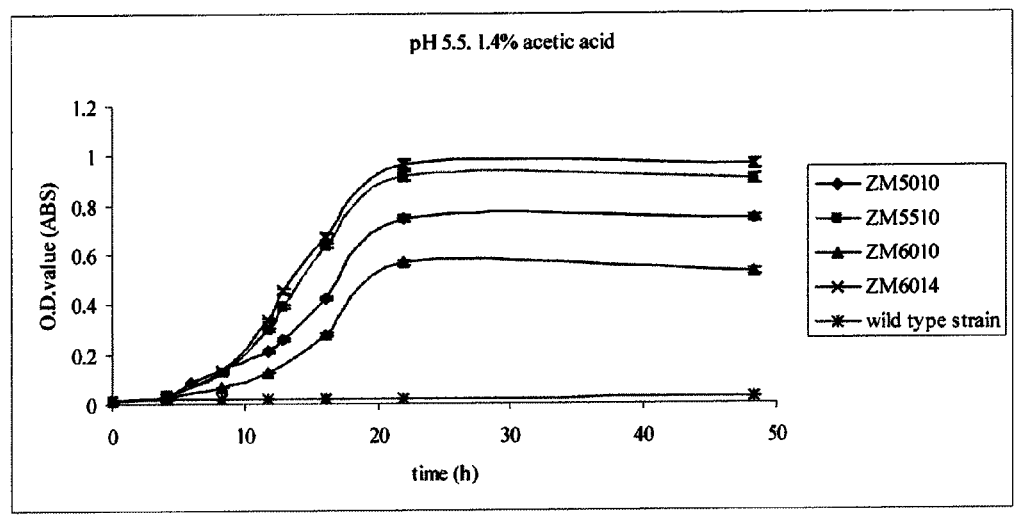
FIG. 21 depicts growth curves at pH 5.5 in the presence of 1.4% acetic acid.
Figure 22:
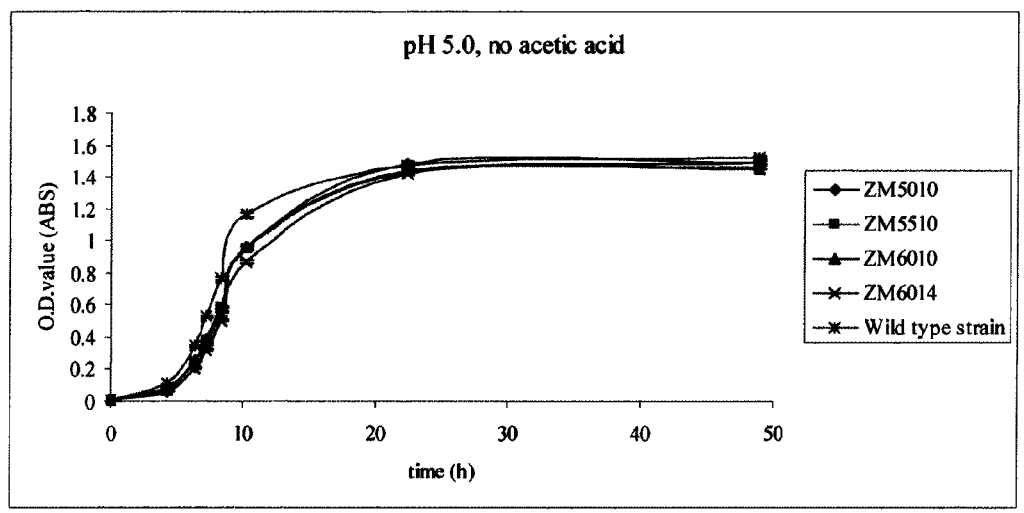
FIG. 22 depicts growth curves at pH 5.0 in the absence of acetic acid.
Figure 23:
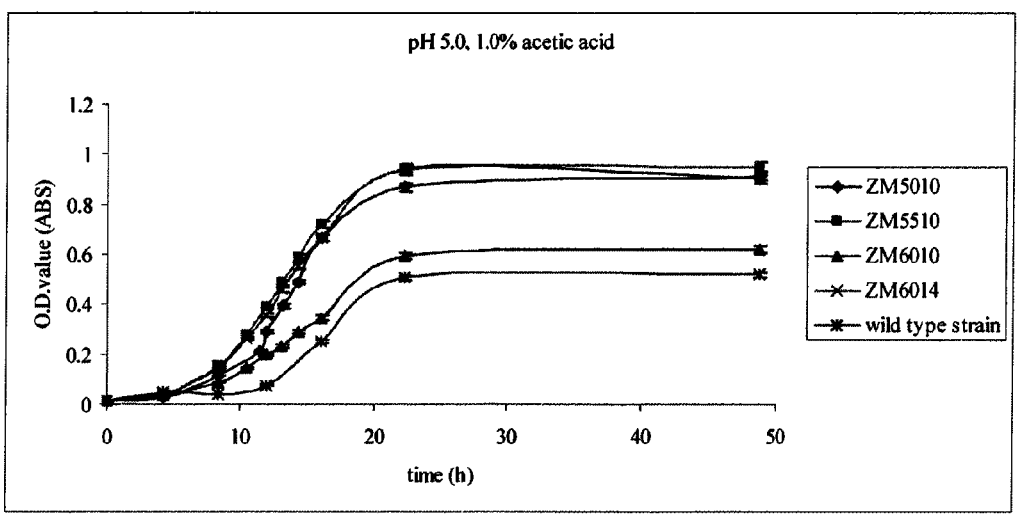
FIG. 23 depicts growth curves at pH 5.0 in the presence of 1.0% acetic acid.
Figure 24:
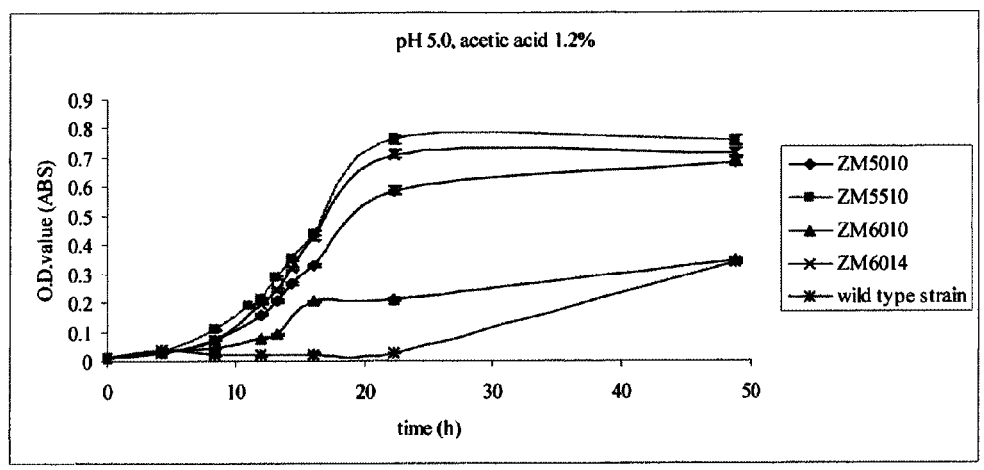
FIG. 24 depicts growth curves at pH 5.0 in the presence of 1.2% acetic acid.
Figure 25:
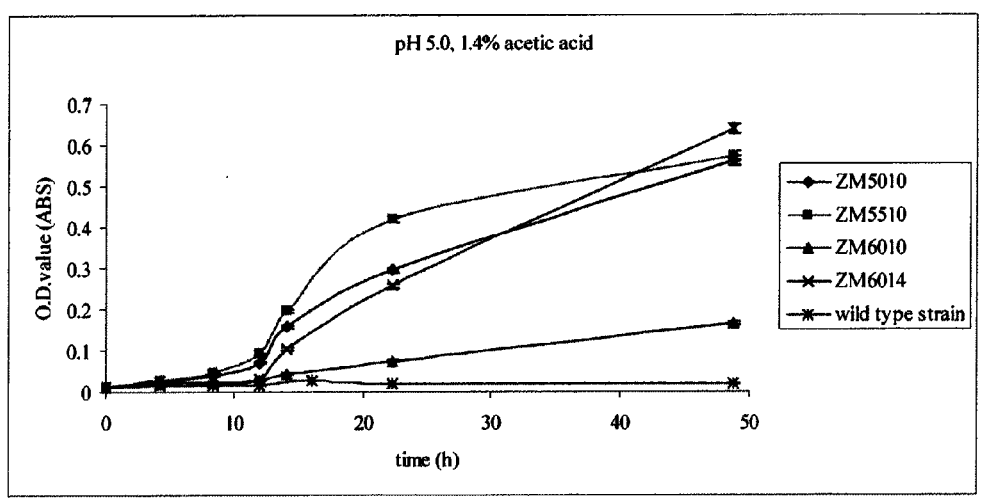
FIG. 25 depicts growth curves at pH 5.0 in the presence of 1.4% acetic acid.

In the presence of 1.4% acetic acid (FIG. 17), the effect of acetic acid on cell growth increased. The original strain barely grew in two days. The O.D. of original strain at 48 hours was only 0.142 and the lag phase of original train was as long as 40 hours. While the lag phase of all mutants was quite similar (about 7.8 hours), the differences between mutants became much larger. ZM6014 had the highest specific growth rate, followed by ZM5510, ZM5010. ZM5510 had the highest O.D, followed by ZM6014 and ZM5010. ZM6010 had both the lowest specific growth rate and lowest O.D. value.

The experimental results presented above clearly show that the mutants obtained by adaptive mutation have higher specific growth rate, shorter lag phase and higher O.D.s in the presence of high concentration of acetic acid, indicating higher acetic acid tolerance for mutants of the original strain.

FIGS. 18 to 21 show the growth curves of original strain and mutants at pH 5.5 with different acetic acid concentrations.

In the absence of acetic acid, the performances of original stain and mutants were similar. Their performances were also similar to that at pH 6.0. Under this condition, the specific growth rate of all strains was about 0.52 h$^{-1}$; the O.D. was about 1.5; and the lag phase was about 4.1 hours.

With increasing the acetic acid concentration, the final O.D. and the specific growth rate decrease and the lag phase increased. Compared to the results at pH 6.0, the specific growth rate and final O.D.s decreased and the lag phase increased in the same amount of acetic acid. For original strain, the lag phase was 8.25 hours in the presence of 1.0% acetic acid. The specific growth rate was 0.306 h$^{-1}$ under this condition and the final O.D. was about 0.9. The four mutants had a similar lag phase (5.0 hours), and similar final O.D.s. But ZM6010 had the lowest specific growth rate 0.354 h$^{-1}$, while the specific growth rates of other three mutants were all around 0.42 h$^{-1}$.

In the presence of 1.2% acetic acid, the lag phase of the wild strain increased to 16 hours. The specific growth rate decreased to 0.103 h$^{-1}$ and it could not complete the fermentation in two days. Among the four mutants, ZM6010 had longest lag phase and lowest specific growth rate. ZM5010 had lower specific growth rate than ZM6014 and ZM5510, although the lag phase was similar for these three mutants.

In the presence of 1.4% acetic acid, original strain did not grow at all in two days. The differences between the mutants became much larger. ZM6014 had the highest O.D. and specific growth rate, both of which were slightly higher than ZM5510. The O.D. and specific growth rate of ZM5010 were lower than both ZM6014 and ZM5510. ZM6010 had the lowest O.D. and specific growth rate, consistent with the results shown above.

The experimental results at pH 5.5 further proved that the mutants had higher acetic acid tolerance than original strain. The results obtained from the experiments carried out at pH 5.5 in the presence of 1.4% acetic acid confirmed that ZM6010 had lowest acetic acid tolerance among four mutants. ZM5010 had lower acetic acid tolerance than ZM6014 and ZM5510. Although it could tolerate the acetic acid, it could not maintain the same specific growth rate as ZM5510.

Strains were also evaluated at pH 5.0 (FIGS. 22-25). At pH 5.0, the performances of mutants and wild strain were similar to those at pH 5.5 and pH 6.0, in the absence of acetic acid. The specific growth rate was about 0.52 h$^{-1}$; the lag phase was about 4,2 hours; the O.D. was about 1.5.

In the presence of 1.0% acetic acid, the original strain had the longest lag phase, lowest specific growth rate and lowest O.D. value. Under this condition, although the lag phases for the four mutants were similar, the specific growth rate of ZM6010 was much lower than that of other mutants, 0.21 h$^{-1}$, versus 0.32 h$^{-1}$.

In the presence of 1.2% acetic acid, neither ZM6010 nor wild strain could complete the fermentation in two days. Among ZM5010, ZM5510 and ZM6014, ZM5010 had the lowest specific growth rate, and O.D. value. ZM6014 had the highest specific growth rate, but ZM5510 had the highest O.D. value.

In the presence of 1.4% acetic acid, none of the strains completed the fermentation in two days. The original strain did not show any growth in two days, and ZM6010 barely grew. Under this severe growth-inhibiting condition, the mutants had a shorter lag phase, a higher specific growth rate and final O.D. than the original strain. ZM5510, ZM6014 and ZM5010 started to grow around 14 hours, and they exhibited a specific growth rate above 0.1 h$^{-1}$.

In summary, at this pH, the lag phase increased with increasing the acetic acid concentration. The specific growth rate and O.D. decreased with increasing the acetic acid concentration. In the presence of same amount of acetic acid, the O.D. and specific growth rate were lower and the lag phase was longer than those at higher pHs for any strain.

Table 4.1 and 4.2 summarize the lag phase and specific growth of all the strains at different experimental conditions.

TABLE 4.1

Lag phases (h) of five strains at different pHs and acetic acid concentrations

| | Acetic acid concentration | | | |
| --- | --- | --- | --- | --- |
| | 0.00% | 1.00% | 1.20% | 1.40% |
| pH 5.0 | | | | |
| ZM5010 | 4.2 ± 0.14 | 6.3 ± 0.13 | 8.4 ± 0.17 | 14.1 ± 0.10 |
| ZM5510 | 4.2 ± 0.14 | 6.3 ± 0.13 | 8.4 ± 0.17 | 14.1 ± 0.10 |

TABLE 4.1-continued

Lag phases (h) of five strains at different pHs and acetic acid concentrations

| | Acetic acid concentration | | | |
|---|---|---|---|---|
| | 0.00% | 1.00% | 1.20% | 1.40% |
| ZM6010 | 4.2 ± 0.14 | 6.3 ± 0.13 | 12.5 ± 0.35 | 22.2 ± 0.23 |
| ZM6014 | 4.2 ± 0.14 | 6.3 ± 0.13 | 8.4 ± 0.17 | 14.1 ± 0.10 |
| original strain pH 5.5 | 4.2 ± 0.14 | 12.0 ± 0.36 | 36.0 ± 0.18 | >48 |
| ZM5010 | 4.1 ± 0.085 | 5.0 ± 0.10 | 5.5 ± 0.11 | 10.6 ± 0.13 |
| ZM5510 | 4.1 ± 0.085 | 5.0 ± 0.10 | 5.5 ± 0.11 | 10.6 ± 0.13 |
| ZM6010 | 4.1 ± 0.085 | 5.0 ± 0.10 | 8.3 ± 0.16 | 11.8 ± 0.20 |
| ZM6014 | 4.1 ± 0.085 | 5.0 ± 0.10 | 5.5 ± 0.11 | 10.6 ± 0.13 |
| original strain pH 6.0 | 4.1 ± 0.085 | 8.3 ± 0.18 | 16.0 ± 0.12 | >48 |
| ZM5010 | 4.1 ± 0.070 | 5.0 ± 0.10 | 5.5 ± 0.11 | 7.8 ± 0.15 |
| ZM5510 | 4.1 ± 0.070 | 5.0 ± 0.10 | 5.5 ± 0.11 | 7.8 ± 0.15 |
| ZM6010 | 4.1 ± 0.070 | 5.0 ± 0.10 | 5.5 ± 0.11 | 7.8 ± 0.15 |
| ZM6014 | 4.1 ± 0.070 | 5.0 ± 0.10 | 5.5 ± 0.11 | 7.8 ± 0.15 |
| original strain | 4.1 ± 0.070 | 7.8 ± 0.16 | 15.2 ± 0.15 | 40.0 ± 0.18 |

TABLE 4.2

Specific growth rates ($h^{-1}$) of five strains at different pHs and acetic acid concentrations

| | Acetic acid concentration | | | |
|---|---|---|---|---|
| pH 5.0 | 0.00% | 1.00% | 1.20% | 1.40% |
| ZM5010 | 0.535 ± 0.020 | 0.319 ± 0.008 | 0.219 ± 0.008 | 0.119 ± 0.013 |
| ZM5510 | 0.503 ± 0.005 | 0.314 ± 0.015 | 0.252 ± 0.012 | 0.164 ± 0.012 |
| ZM6010 | 0.528 ± 0.014 | 0.211 ± 0.014 | 0.147 ± 0.008 | 0.030 ± 0.001 |
| ZM6014 | 0.507 ± 0.010 | 0.325 ± 0.010 | 0.285 ± 0.011 | 0.135 ± 0.017 |
| original strain | 0.523 ± 0.021 | 0.196 ± 0.003 | 0.098 ± 0.007 | N/A |

| | Acetic acid concentration | | | |
|---|---|---|---|---|
| pH 5.5 | 0.00% | 1.00% | 1.20% | 0.014 |
| ZM5010 | 0.518 ± 0.015 | 0.417 ± 0.008 | 0.304 ± 0.008 | 0.183 ± 0.007 |
| ZM5510 | 0.524 ± 0.022 | 0.415 ± 0.018 | 0.362 ± 0.017 | 0.247 ± 0.012 |
| ZM6010 | 0.525 ± 0.025 | 0.354 ± 0.020 | 0.266 ± 0.014 | 0.169 ± 0.001 |
| ZM6014 | 0.523 ± 0.022 | 0.422 ± 0.015 | 0.386 ± 0.016 | 0.252 ± 0.014 |
| original strain | 0.517 ± 0.014 | 0.306 ± 0.030 | 0.103 ± 0.002 | N/A |

| | Acetic acid concentration | | | |
|---|---|---|---|---|
| pH 6.0 | 0.00% | 1.00% | 1.20% | 1.40% |
| ZM5010 | 0.519 ± 0.017 | 0.411 ± 0.015 | 0.363 ± 0.015 | 0.314 ± 0.006 |
| ZM5510 | 0.521 ± 0.020 | 0.447 ± 0.013 | 0.431 ± 0.010 | 0.331 ± 0.018 |
| ZM6010 | 0.516 ± 0.012 | 0.400 ± 0.030 | 0.367 ± 0.007 | 0.289 ± 0.018 |
| ZM6014 | 0.534 ± 0.019 | 0.467 ± 0.030 | 0.425 ± 0.008 | 0.351 ± 0.007 |
| original strain | 0.507 ± 0.012 | 0.306 ± 0.008 | 0.151 ± 0.017 | N/A |

As seen from the data, all the mutants obtained by adaptive mutation have the higher acetic acid tolerance than original strain. Among the mutants, ZM5510 and ZM6014 have the highest acetic acid tolerance, followed by ZM5010 and ZM6010.

Example 5

Comparison of Mutants Developed by Adaptive and NTG Mutagenesis

The growth behaviors of mutants developed by adaptive mutation alone and by adaptive mutation followed by NTG mutagenesis were compared. Seed media with 1.4% and 1.6% acetic acid and 5.0, 5.5 and 6.0 pH were used in this experiment. The mutants ZM5510 and ZM6014, the two more adapted mutants from adaptive mutation, were chosen to compare the mutants developed further by NTG mutagenesis.

Figure 26:
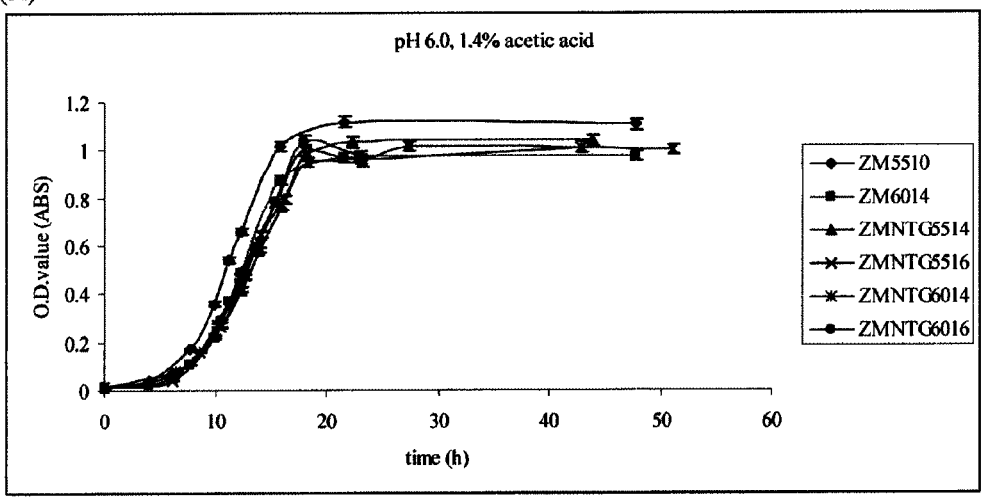
FIG. 26 depicts growth curves at pH 6.0 in the presence of (A) 1.4% and (B) 1.6% acetic acid.
Figure 26:
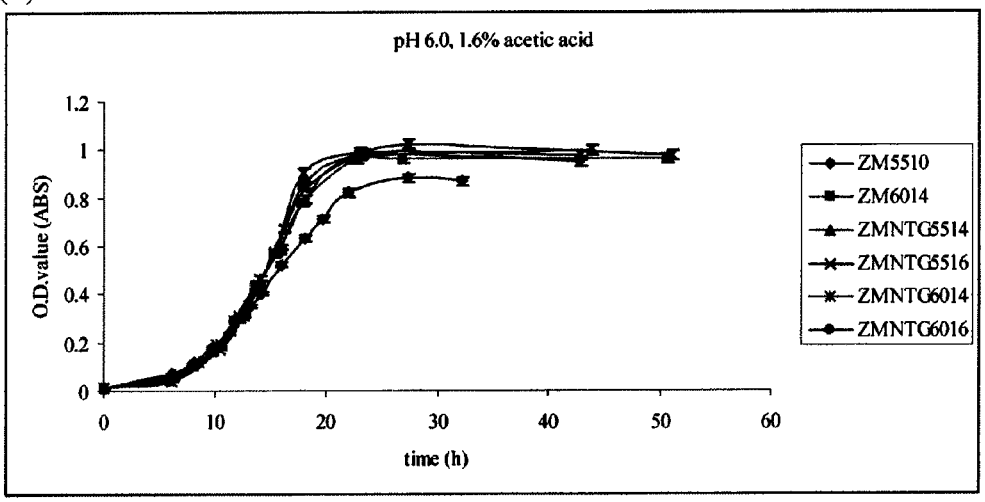
Figure 27:
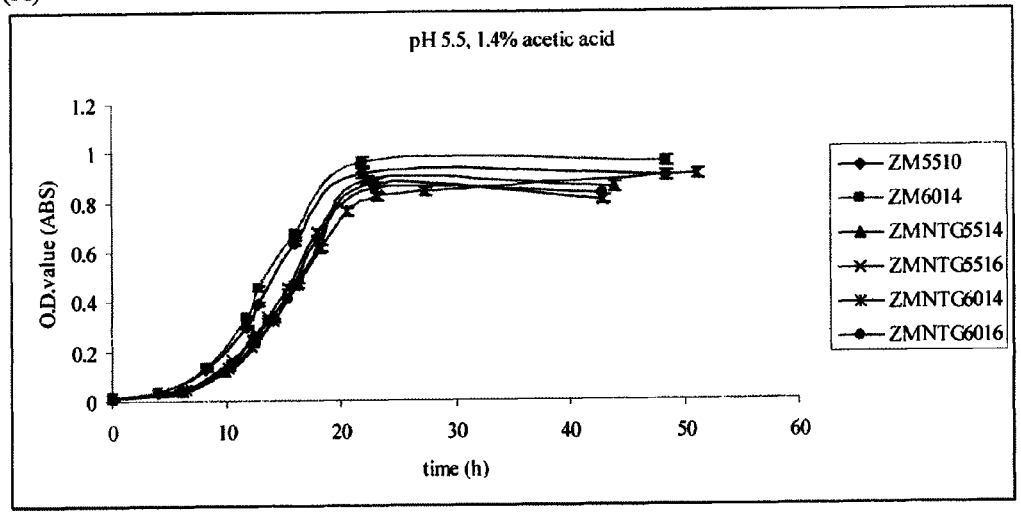
FIG. 27 depicts growth curves at pH 5.5 in the presence of (A) 1.4% and (B) 1.6% acetic acid.
Figure 27:
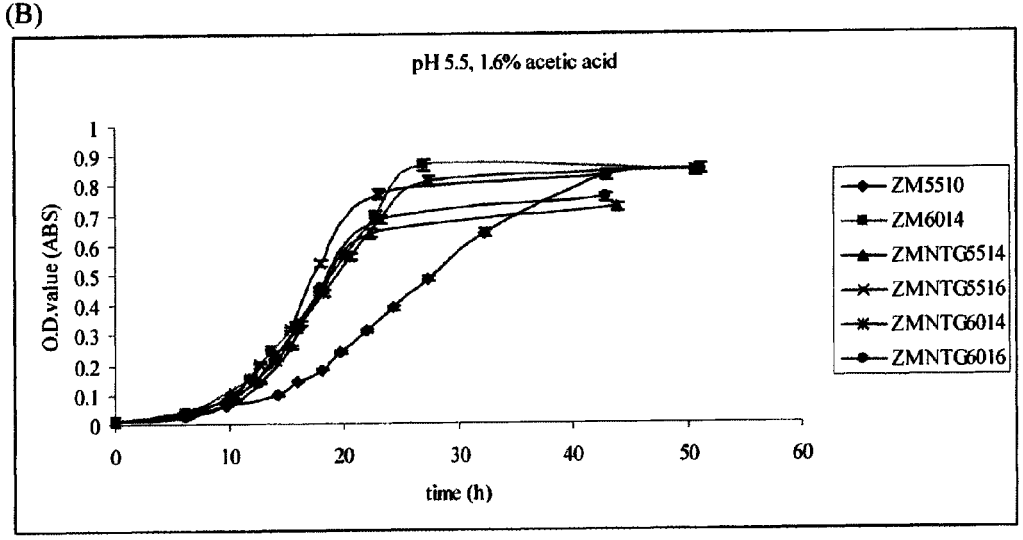
Figure 28:
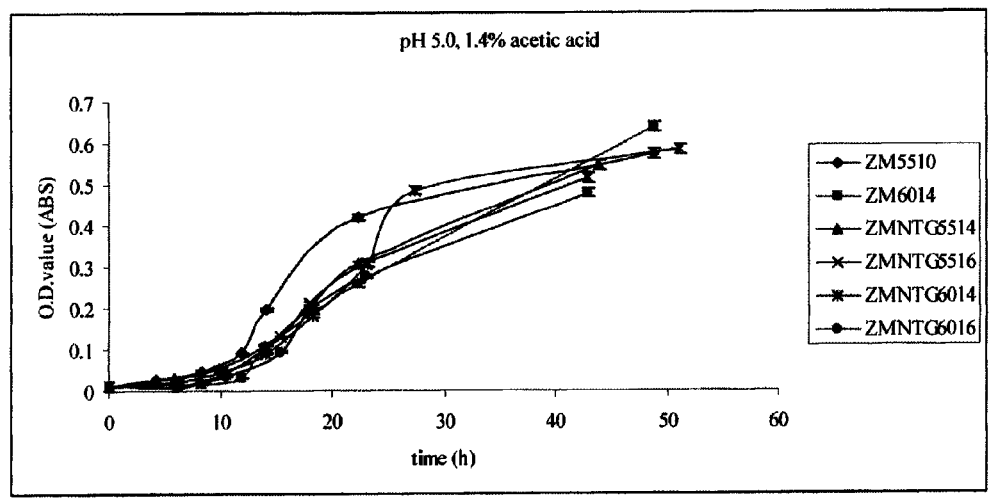
FIG. 28 depicts growth curves at pH 5.0 in the presence of (A) 1.4% and (B) 1.6% acetic acid.
Figure 28:
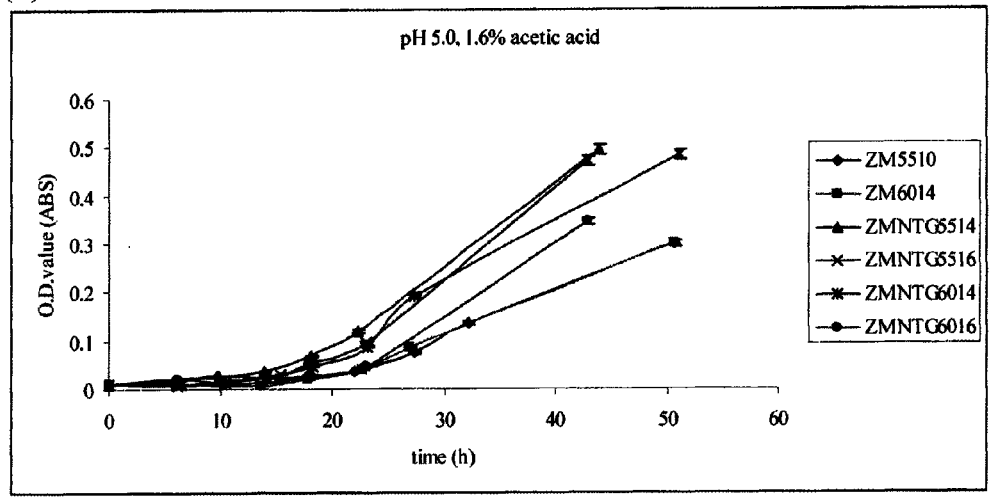

FIGS. 26 to 28 show the growth curves of different mutants in the presence of 1.4% (A) and 1.6% (B) acetic acid at different pHs.

At pH 6.0, in the presence of 1.4% acetic acid, the performances of all the mutants were similar based on the O.D., specific growth rate (0.33 $h^{-1}$) and lag phase (7.8 hours). However, in the presence of 1.6% acetic acid, ZM5510 had the lower O.D. and specific growth rate (0.249 $h^{-1}$) than other mutants (0.3 $h^{-1}$).

At pH 5.5 (FIG. 28), in the presence of 1.4% acetic acid, the performances of all the mutants were similar based on the final O.D., specific growth rate (0.25 $h^{-1}$), and lag phase (10.2 hours). In the presence of 1.6% acetic acid, ZM5510 had the lowest specific growth rate (0.17 $h^{-1}$) and O.D. value. This mutant also had the longest lag phase (14.3 hours). Other mutants had a similar lag phase (12.5 hours), but ZMNTG5514 and ZMNTG6016 also showed a slightly lower O.D. than ZM6014, ZMNTG5516 and ZMNTG6014. ZMNTG5514, ZMNTG5516 and ZMNTG6016 had the highest specific growth rate (0.23 $h^{-1}$).

Compared to the experimental results obtained at pH 6.0, the lag phase became longer and the specific growth rate was lowered, as expected, for each strain with the same amount of acetic acid.

Figure 29:
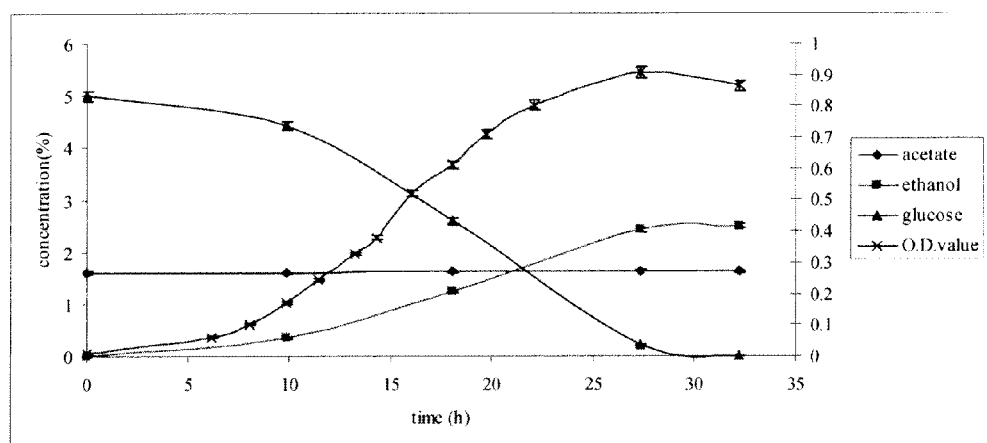
FIG. 29 provides plot of ethanol, glucose, acetic acid concentration, and O.D. as a function of time for ZM5510 at pH 6.0 in the presence of 1.6% acetic acid.

At pH 5.0, no strain completed the fermentation in two days (FIG. 29). In the presence of 1.4% acetic acid, ZM5510 and ZM6014 had a slightly shorter lag phase (14.1 hours) than other mutants (14.5 hours). ZMNTG5516 and ZMNTG6014 had a slightly higher specific growth rate (0.19 $h^{-1}$) than other mutants (between 0.132 and 0.164 $h^{-1}$). In the presence of 1.6% acetic acid, ZM5510, ZM6014 and ZMNTG6016 had longer lag phase (27.1 hours) than other mutants (22.8 hours). ZMNTG6014 had slightly higher specific growth rate (0.18 h$^{-1}$) than other mutants. ZMNTG5514, ZMNTG5516 and ZMNTG6016, which showed the highest specific growth rate at pH 5.5 in the presence of 1.6% acetic acid, had the lower specific growth rate than ZM6610. ZMNTG 5516 and ZMNTG 6016 had the lower specific growth rate than ZM5510. This is because of the fact that NTG mutagenesis is a random mutation, so the behaviors of the mutants obtained by NTG mutagenesis are somewhat unpredictable.

Table 5.1 and 5.2 summarize the lag phases and specific growth rates of all mutants at different experimental conditions.

TABLE 5.1

Lag phases (h) of six strains at different pHs and acetic acid concentrations

| | Acetic acid concentration | |
| --- | --- | --- |
| | 1.40% | 1.60% |
| pH 5.0 | | |
| ZM5510 | 14.1 ± 0.10 | 27.1 ± 0.11 |
| ZM6014 | 14.1 ± 0.10 | 27.1 ± 0.11 |
| ZMNTG5514 | 14.5 ± 0.08 | 22.8 ± 0.12 |
| ZMNTG5516 | 14.5 ± 0.08 | 22.8 ± 0.12 |
| ZMNTG6014 | 14.5 ± 0.08 | 22.8 ± 0.12 |
| ZMNTG6016 | 14.5 ± 0.08 | 27.1 ± 0.11 |
| pH 5.5 | | |
| ZM5510 | 10.2 ± 0.14 | 14.3 ± 0.11 |
| ZM6014 | 10.2 ± 0.14 | 12.5 ± 0.13 |
| ZMNTG5514 | 10.2 ± 0.14 | 12.5 ± 0.13 |
| ZMNTG5516 | 10.2 ± 0.14 | 12.5 ± 0.13 |
| ZMNTG6014 | 10.2 ± 0.14 | 12.5 ± 0.13 |
| ZMNTG6016 | 10.2 ± 0.14 | 12.5 ± 0.13 |
| pH 6.0 | | |
| ZM5510 | 7.8 ± 0.15 | 8.3 ± 0.14 |
| ZM6014 | 7.8 ± 0.15 | 8.3 ± 0.14 |
| ZMNTG5514 | 7.8 ± 0.15 | 8.3 ± 0.14 |
| ZMNTG5516 | 7.8 ± 0.15 | 8.3 ± 0.14 |
| ZMNTG6014 | 7.8 ± 0.15 | 8.3 ± 0.14 |
| ZMNTG6016 | 7.8 ± 0.15 | 8.3 ± 0.14 |

TABLE 5.2

Specific growth rates (h$^{-1}$) of six strains at different pHs and acetic acid concentrations

| | Acetic acid concentration | |
| --- | --- | --- |
| | 1.40% | 1.60% |
| pH 5.0 | | |
| ZM5510 | 0.164 ± 0.012 | 0.122 ± 0.011 |
| ZM6014 | 0.149 ± 0.004 | 0.135 ± 0.017 |
| ZMNTG5514 | 0.146 ± 0.002 | 0.135 ± 0.007 |
| ZMNTG5516 | 0.193 ± 0.008 | 0.115 ± 0.012 |
| ZMNTG6014 | 0.186 ± 0.008 | 0.184 ± 0.003 |
| ZMNTG6016 | 0.132 ± 0.011 | 0.112 ± 0.010 |
| pH 5.5 | | |
| ZM5510 | 0.247 ± 0.012 | 0.170 ± 0.007 |
| ZM6014 | 0.252 ± 0.014 | 0.211 ± 0.004 |
| ZMNTG5514 | 0.249 ± 0.005 | 0.231 ± 0.013 |
| ZMNTG5516 | 0.243 ± 0.008 | 0.235 ± 0.012 |
| ZMNTG6014 | 0.239 ± 0.005 | 0.208 ± 0.020 |
| ZMNTG6016 | 0.264 ± 0.003 | 0.235 ± 0.003 |

TABLE 5.2-continued

Specific growth rates (h$^{-1}$) of six strains at different pHs and acetic acid concentrations

| | Acetic acid concentration | |
| --- | --- | --- |
| | 1.40% | 1.60% |
| pH 6.0 | | |
| ZM5510 | 0.331 ± 0.018 | 0.249 ± 0.024 |
| ZM6014 | 0.351 ± 0.007 | 0.312 ± 0.006 |
| ZMNTG5514 | 0.329 ± 0.010 | 0.298 ± 0.010 |
| ZMNTG5516 | 0.330 ± 0.007 | 0.322 ± 0.012 |
| ZMNTG6014 | 0.317 ± 0.017 | 0.298 ± 0.008 |
| ZMNTG6016 | 0.328 ± 0.006 | 0.301 ± 0.003 |

In summary, it is difficult to compare the acetic acid tolerance between these mutants. Although at some experimental conditions, some ZMNTG mutants showed better performance than ZM5510 or ZM6014 based on one of the three parameters studied, these mutants could also show worse performances under other experimental conditions. No ZMNTG mutant showed a better performance than ZM6014 at all experimental conditions.

Example 6

Ethanol Production Characteristics of Mutants

In this experiment, the ethanol production characteristics of the mutants were studied.

Based on the stoichiometry, the theoretical ethanol yield should be about 0.51 g ethanol/g glucose or, about 51%. That means the ethanol concentration should be around 2.55% if the initial glucose concentration is 5% (w/v).

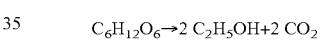
$C_6H_{12}O_6 \rightarrow 2\ C_2H_5OH + 2\ CO_2$

FIG. 29 shows an example of the ethanol production, glucose consumption and the acetate concentration, as well as the growth curve as a function of time for ZM5510 at pH 6.0 in the presence of 1.6% acetic acid. The "Δ" curve represents the glucose concentration. The initial glucose concentration was about 5%. The strain did not start to ferment the glucose immediately, which is corresponding to the lag phase in the growth curve ("x" curve). The final glucose concentration was zero, indicating a complete consumption of glucose.

The ethanol concentration curve ("□") shows that the strain started to produce ethanol as soon as it started to consume glucose. The final ethanol concentration was around 2.5%, which is a theoretical yield. This proves that the mutant could retain the ability for efficient ethanol fermentation.

Figure 30:
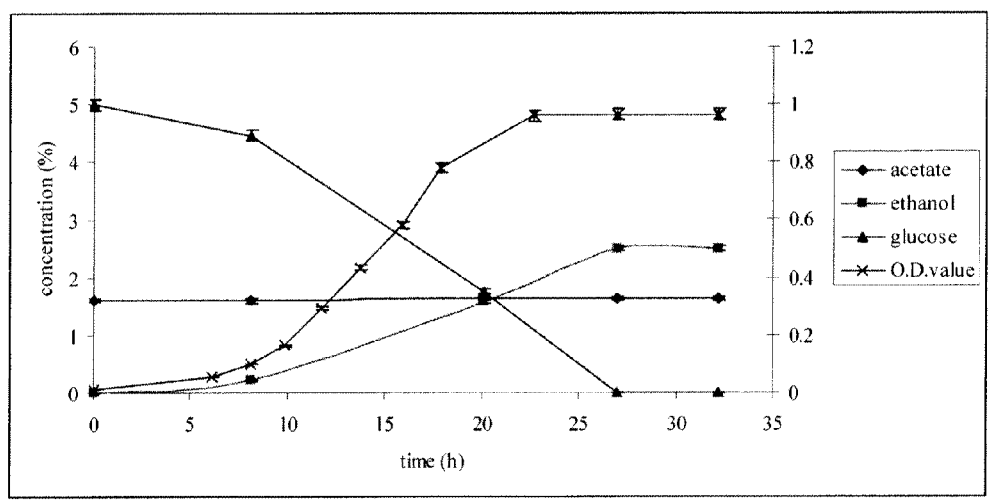
FIG. 30 provides plot of ethanol, glucose, acetic acid concentration, and O.D. as a function of time for ZM6014 at pH 6.0 in the presence of 1.6% acetic acid.

FIG. 30 shows another example of the ethanol production, glucose consumption and the acetate concentration, as well as the growth curve as a function of time. The strain used is ZMNTG6014 and the experiment was carried out at pH 6.0 in the presence of 1.6% acetic acid. The ethanol production characteristics of ZM6014 are similar to that of ZM5510. The glucose consumption had a lag phase. The glucose was completely consumed. The final ethanol concentration was 2.5% the ethanol yield was about 50%.

The ethanol production characteristics of these two mutants were also evaluated under other conditions. Results are summarized in Table 6.1. These two mutants were chosen because they had the highest acetic acid tolerance among all the mutants obtained by adaptive mutation. The experimental results showed that once the fermentation was completed, the ethanol yield was always around the theoretical value, which was 50%. Ethanol yield of fermentation obtained at pH 5.0 in the presence of 1.6% acetic acid was only about 66% of the theoretical value. This is due to the incomplete fermentation within two days. However the experiments carried out under other conditions were all completed in two days, the final yields were all about 100% of the theoretical value. This means mutant ZM5510 and ZM6014, retain the advantage of high ethanol yield.

TABLE 6.1

Ethanol production characteristics of two mutants in different fermentation conditions (% of theoretical number)

| | ZM5510 | ZM6014 |
|---|---|---|
| 5014 | 102.0 ± 1.99 | 100.1 ± 0.73 |
| 5514 | 99.6 ± 1.37 | 99.5 ± 1.04 |

TABLE 6.1-continued

Ethanol production characteristics of two mutants in different fermentation conditions (% of theoretical number)

| | ZM5510 | ZM6014 |
|---|---|---|
| 6014 | 97.9 ± 1.48 | 100.7 ± 0.72 |
| 5016 | 65.8 ± 1.74 | 67.2 ± 0.97 |
| 5516 | 99.3 ± 0.84 | 98.6 ± 1.29 |
| 6016 | 99.6 ± 1.16 | 100.1 ± 0.60 |

The acetic acid concentrations were also measured throughout the fermentation. The acetic acid concentration curves (labeled "acetate") in FIGS. 29 and 30 show that it was constant with time. This shows that consumption of acetic acid is not the tolerant mechanism. The pH measured at the end of fermentation was the same as the initial value, indicating constant pH during the fermentation. The constant pH and acetic acid suggest that the tolerance is not due to the change of environmental conditions during fermentation.

Example 7

Resistance to Other Inhibitors

To test whether mutants developed for acetic acid tolerance could cross-protect the cells for other inhibitors, additional experiments were carried out with four common inhibitors (vanillin, formic acid, hydroxybenzoic acid, and furfuryl alcohol) derived from biomass. Each inhibitor was evaluation at two concentrations.

The mutant ZM6014 was chosen for the study. The O.D. values after two day fermentation and the specific growth rates are summarized in Table 7.1. The ethanol productions after two day fermentation are summarized in Table 7.2.

Mutant ZM6014 shows a higher tolerance to formic acid than original strain. In the presence of 2.68 g/l formic acid, ZM6014 grew to a much higher O.D. and specific growth rate than original strain.

Without being bound to any specific theory, it is believed that the mechanism of tolerance of formic acid, which is a weak acid, is similar to acetic acid, which is also a weak acid.

The mutant ZM6014 also shows the higher tolerance to vanillin based on specific growth rate, especially in the presence of high concentration of vanillin (1 g/L).

Furfuryl alcohol is a furan derivative formed by dehydration of hexoses. There was no inhibition observed in concentration range in the experiments conducted.

TABLE 7.1

O.D. value and specific growth rate of fermentation in the presence of different inhibitors

| | Final O.D. | | Specific growth rate ($h^{-1}$) | |
|---|---|---|---|---|
| | | | Original | |
| Inhibitors | Original ZM4 | ZM6014 | ZM4 | ZM6014 |
| Vanillin (0.5 g/L) | 1.310 ± 0.064 | 1.364 ± 0.071 | 0.231 ± 0.001 | 0.290 ± 0.002 |
| Vanillin (1 g/L) | 1.013 ± 0.037 | 1.111 ± 0.082 | 0.168 ± 0.027 | 0.242 ± 0.001 |
| Formic acid (2.68 g/L) | 0.546 ± 0.036 | 0.927 ± 0.024 | 0.208 ± 0.003 | 0.2973 ± 0.04 |
| Formic acid (5.37 g/L) | 0.021 ± 0.000 | 0.027 ± 0.000 | N/A | N/A |
| Hydroxybenzoic acid (3.4 g/L) | 1.467 ± 0.045 | 1.421 ± 0.014 | 0.405 ± 0.019 | 0.428 ± 0.030 |
| Hydroxybenzoic acid (6.8 g/L) | 1.446 ± 0.028 | 1.476 ± 0.029 | 0.368 ± 0.010 | 0.388 ± 0.008 |
| Furfuryl alcohol (3.89 g/L) | 1.469 ± 0.027 | 1.444 ± 0.027 | 0.507 ± 0.019 | 0.510 ± 0.004 |
| Furfuryl alcohol (7.79 g/L) | 1.468 ± 0.005 | 1.454 ± 0.024 | 0.510 ± 0.008 | 0.536 ± 0.015 |

The ethanol yields were not affected by the inhibitors. Once the fermentation finished, and the strain reached the maximum O.D., the ethanol yield was always similar to the theoretical number. The ethanol production was only 5% of theoretical value in the presence of 5.37 g/L formic acid. This is because the strain only grew a little during experimental time.

TABLE 7.2

Ethanol production of two strains in the presence of different inhibitions (% of theoretical yield)

| Inhibitors | ZM4 | Original ZM6014 |
|---|---|---|
| Vanillin (0.5 g/L) | 101.0 ± 1.20 | 99.2 ± 1.65 |
| Vanillin (1 g/L) | 99.5 ± 2.25 | 102 ± 1.44 |
| Formic acid (2.68 g/L) | 98.9 ± 2.30 | 97.0 ± 1.79 |
| Formic acid (5.37 g/L) | 5.1 ± 0.000 | 5.2 ± 0.000 |
| Hydroxybenzoic acid (3.4 g/L) | 97.7 ± 1.03 | 98.5 ± 1.65 |
| Hydroxybenzoic acid (6.8 g/L) | 98.0 ± 2.34 | 99.4 ± 1.89 |
| Furfuryl alcohol (3.89 g/L) | 98.7 ± 2.46 | 99.6 ± 2.63 |
| Furfuryl alcohol (7.79 g/L) | 98.3 ± 1.70 | 99.9 ± 2.39 |

As seen from the data, regardless pH, higher acetic acid concentration resulted in lower specific growth rate and lower produced biomass and longer lag phase. The effect of acetic acid became much more severe at low pH.

Through adaptive mutation, several useful acetic acid tolerant strains were developed. Compared to the original strain, these mutants exhibited higher specific growth rate, higher final O.D. and had significantly shorter lag phase in the presence of acetic acid, indicating superior tolerance for the mutants. For example, the most adapted mutant could grow at the most inhibitive condition tested (pH 5.0 and 1.4% acetic acid concentration) with specific growth rate 0.16 $h^{-1}$, whereas the original strain could not grow at all under the same condition.

The mutants retained high ethanol fermentation capability, with ethanol yield approaching the theoretical yield. Ethanol fermentation time profile and the lag phase correspond to the cell growth, which indicates tight coupling of the ethanol production with cell growth.

The examples also reveal that enhanced acetic acid tolerance may lead to enhanced tolerance to other inhibitors including formic acid, hydroxybenzoic acid, and vanillin. This cross-protection makes acetic acid tolerant strains more attractive for use in bioethanol production from renewable sources.

In summary, by adaptive mutation, the acetic acid tolerant *Z. mobilis* strains were successfully developed. These strains have been proved to have higher acetic acid tolerance than original strain and still have the high ethanol yield. These mutants have also been proved to have higher tolerance to other inhibitors, such as formic acid and vanillin while maintaining tolerance to such inhibitors as hydroxybenzoic acid.

Example 8

Adaptive Mutation for Utilization of Xylose

The strains used were *Zymomonas mobilis* ZM4 and *Escherichia coli* JM109, JM110 and SZ63 as described in, for example, Shengde Zhou, T. B. C., A. Hasona, K. T. Shanmugam, and L. O. Ingram, *Production of Optically Pure D-Lactic Acid in Mineral Salts Medium by Metabolically Engineered Escherichia coli W*3110. Applied and Environmental Microbiology, 2003. 69(1): p. 399-407. ZM4 was grown in rich media (RM) which contains (in g/l) yeast extract 10, glucose 20 and $KH_2PO_4$ 2. When growing solely on xylose, glucose in RM is replaced by xylose. *E coli* cells were routinely grown in LB media. Whenever necessary, media was supplemented with antibiotic at a final concentration (in μg/ml) of chloramphenicol 100 and ampicillin 100. The fermenter used was from Infors HT Multifors, Bottmingen, Switzerland.

Plasmid pZMETX as shown in FIG. 32 was constructed by subcloning elements (1), (2), and (3) from *E coli* SZ63 and *Z mobilis* into commercially available vector pSTV28 as described in, for example, Inc, T.B. pSTV28/29 DNA. 2008; available from: http://catalog.takara-bio.co.jp/en/product/basic_info.asp?unitid=U100005674.

Element (1) Ppdc-xy1A-xy1B—Ppdc is the native pyruvate decarboxylase promoter of *Z mobilis* ZM4 (described in, for example, Seo, J. S., et al., *The genome sequence of the ethanologenic bacterium Zymomonas mobilis ZM*4. Nature Biotechnology, 2005. 23(1): p. 63-68.). xy1A-xy1B is present as an operon in *E coli* SZ63 (described in, for example, cited 2009 Mar. 13, 2009; available from: http://ecocyc.org/) encoding for the genes xylose isomerase and xylulokinase respectively.

Element (2) Peno-ta1B-tktA—Peno is the native enolase promoter of *Z mobilis* ZM4. (described in, for example, Seo, J. S., et al., *The genome sequence of the ethanologenic bacterium Zymomonas mobilis ZM*4. Nature Biotechnology, 2005. 23(1): p. 63-68.) ta1B and tktA have been cloned from *E coli* SZ63 (described in, for example, cited 2009 Mar. 13, 2009; available from: http://ecocyc.org/) which encode for the genes transaldolase and transketolase respectively.

Element (3) ZM27—It is the region containing the origin of replication and necessary genetic information for the maintenance of plasmid pZMETX inside a *Z mobilis* cell. ZM27 has been cloned from the 2.7 kb native plasmid pZMO3 of *Z mobilis* ATCC 10988 (described in, for example, Afendra, A. S., et al., *Characterization of the mobilization region of the Zymomonas mobilis ATCC*10988 *plasmid pZMO*3. Plasmid, 1999. 41(1): p. 73-77. incorporated herein by reference).

The transformation of plasmid pZMETX into *Z mobilis* ZM4 occurred as follows: JM 109 or JM 110 was used as an intermediate host for harboring the plasmid pZMETX. Plasmid extraction was done from JM109/pZMETX or JM110/pZMETX using the protocols of plasmid miniprep kit manufacturers (Fermentas GeneJet and Zymoresearch incorporated herein by reference). The extracted plasmid was electroporated into competent cells of *Z mobilis* ZM4.

Confirmation for the presence of plasmid pZMETX in ZM4/pZMETX was done using colony PCR and enzymatic assays for the four cloned gene products namely xylose isomerase, xylulokinase, transaldolase and transketolase. Enzymatic assays are described at, for example, Callens, M., et al., CATALYTIC PROPERTIES OF D-XYLOSE ISOMERASE FROM *STREPTOMYCES-VIOLACEORUBER*. Enzyme and Microbial Technology, 1986.8(11): p. 696-700 and Feldmann, S. D., H. Sahm, and G. A. Sprenger, *Pentose metabolism in Zymomonas mobilis wild-type and recombinant strains*. Applied Microbiology and Biotechnology, 1992. 38(3): p. 354-361.

Adaptive mutation for utilization of xylose—ZM4/pZMETX was unable to grow on xylose initially. Hence, it was first grown on a mixture of glucose and xylose. Thus, according to FIG. 31, a selective pressure of xylose was applied on the strains while culturing them in RM. The sum of glucose and xylose in RM was set at a concentration 5%. To begin with, the amount of xylose was 0.25% while the amount of glucose was 4.75%. During the adaptive mutation process, the xylose amount was gradually stepped up from 0.25% to 5% and glucose concentration was decreased from 4.75% to 0 simultaneously. The adaptive mutations resulted in an adapted mutant strain ZM4/pZMETX A1 that could grow on 5% xylose.

Adaptive mutation for increasing specific growth rate and volumetric ethanol productivity from xylose—Subsequent rounds of adaptive mutation were carried in RM supplemented with 5% xylose to obtain strains with a higher specific growth rate and volumetric ethanol productivity. Two improved strains were obtained, namely ZM4/pZMETX A2 and ZM4/pZMETX A3. Suffices 1, 2 and 3 indicate the strains obtained after $1^{st}$, $2^{nd}$ and $3^{rd}$ sets of adaptive mutations respectively. ZM4/pZMETX A3 is the most adapted xylose utilizing strain obtained so far and ZM4/pZMETX A1 is the first generation of the adaptive mutation.

Screw-cap bottle fermentation for ZM4/pZMETX A2—This experiment was carried out in static screw-cap bottles filled to 60% of the total volume with RM supplemented with 5% xylose. No pH control was done. Samples were withdrawn at regular intervals to determine the concentration of cell mass, xylose and ethanol in the culture broth. Results for this experiment have been summarized in FIG. 33 and Table 8.1. The ethanol yield and volumetric ethanol productivity obtained for the batch fermentation in screw-cap bottle is higher than that reported in the literature.

Fermentation by ZM4/pZMETX A2 and ZM4/pZMETX A3 in a fermenter at pH of 6—ZM4/pZMETX A2 and ZM4/pZMETX A3 were evaluated in a fermenter at an rpm of 150 with 5% xylose. The pH of the fermenter was controlled at 6 by the addition of 2N NaOH base and 1N $H_3PO_4$ acid. Anaerobic conditions were maintained by sparging nitrogen gas through the culture at the rate of 0.21 pm at 1 bar pressure. The results of the fermentation have been summarized in FIGS. 34, 35 and tables 8.1 and 8.3 while reported literature results are shown in table 8.2. Specific growth rate, volumetric and specific ethanol productivity and specific xylose consumption rate for ZM4/pZMETX A3 was higher than that of ZM4/pZMETX A2 and the strains reported in literature. Thus, the adaptive mutants exhibit surprising and unexpected results such as ethanol production.

Fermentation by ZM4/pZMETX A2 and ZM4/pZMETX A3 in a fermenter without pH control—All the conditions in the fermenter were kept similar to aforementioned fermentation except that no pH control was employed. For fermentation by both ZM4/pZMETX A2 and ZM4/pZMETX A3, the pH dropped from an initial value of 5.9 to a final value of 4.7. Compared to the previous fermentation where the pH was held constant at 6, no significant difference was noted in the various fermentation rates and yield as can be seen from Table 8.1. This demonstrates the ability of strain ZM4/pZMETX A3 to carry out fermentation without employing pH control at surprising and unexpected rates relative to those described in the literature.

TABLE 8.1

Adapted strain experimental data

| | Experimental Data | | | | |
|---|---|---|---|---|---|
| | ZM4/pZMETX A3 | ZM4/pZMETX A2 | ZM4/pZMETX A3 | ZM4/pZMETX A2 | ZM4/pZMETX A2 |
| Fermentation mode | Batch, pH stat (6) Fermenter | | Batch, no pH control, Fermenter | | Batch (bottle) |
| Amount of xylose fermented | 46.6 g/l | 45.5 g/l | 48.1 g/l | 47.8 g/l | 50 g/l |
| Ethanol yield (% of theoretical) | *88% | *74% | *89% | *78.70% | 97% |
| Final DCM (dry cell mass) | 1.64 g/l | 1.67 g/l | 1.96 g/l | 1.92 g/l | 0.49 g/l |
| Avg sp. Growth rate | 0.141 $h^{-1}$ | 0.088 $h^{-1}$ | 0.134 $h^{-1}$ | 0.093 $h^{-1}$ | 0.042 $h^{-1}$ |
| Volumetric ethanol productivity (avg) | 0.83 g/l/h | 0.393 g/l/h | 0.83 g/l/h | 0.5 g/l/h | 0.4 g/l/h |
| Sp. Ethanol productivity (avg) | 0.979 g/g/h | 0.457 g/g/h | 0.881 g/g/h | 0.624 g/g/h | 1.59 g/g/h |
| Sp. Xylose consumption rate (avg) | 2.19 g/g/h | 1.213 g/g/h | 2.151 g/g/h | 1.072 g/g/h | 3.138 g/g/h |
| Time taken to completely consume xylose (hours) | ~25 h (by extrapolation, Starting cell mass = 61.2 mg DCW/l | ~45 h (Starting cell mass = 51.5 mg DCW/l) | 25-30 (by extrapolation, Starting cell mass = 65.1 mg DCW/l | ~45 h (by extrapolation, Starting cell mass = 70.6 mg DCW/l) | 61.25 (starting OD = 0.1 = 35.1 mg DCW/l) |

*Significant amount of ethanol was present in the exit stream of gas when fermentation was carried out in a bioreactor with nitrogen bubbling through the medium. The yield calculation did not take into account the loss of ethanol in the exit gas stream. Hence, the yields shown represent a low estimate. When the same strains were used in fermentation with capped flasks, the yields were in high 90%.
DCW—Dry cell weight;
MR—Maximum reported value. Average value was not reported by the authors;
ND—Not Determined;
NR—Not reported

TABLE 8.2

Literature Data

| | Literature data | | | | |
|---|---|---|---|---|---|
| | CP4 (pZB5)[1] | ZM4 (pZB5)[2] | | | Integrated AX101[3] |
| Fermentation mode | Batch (Flask) | Batch, pH stat (5) | | | Batch, pH stat (5.5) |
| Amount of xylose fermented | 25 g/l | 60.5 g/l | 40.3 g/l | 27.8 g/l | 20.17 g/l |
| Ethanol yield (% of theoretical) | 86% | 81% | 82% | 88% | 98% |
| Final DCM (dry cell mass) | NR | 1.5 g/l | NR | 1.5 g/l | 0.68 g/l |
| Avg sp. Growth rate | 0.057 $h^{-1}$ | 0.11 $h^{-1}$ (MR) | 0.12 $h^{-1}$ (MR) | 0.13 $h^{-1}$ (MR) | 0.06 $h^{-1}$ |
| Volumetric ethanol productivity (avg) | 0.256 g/l/h | 0.314 g/l/h | NR | 0.252 g/l/h | 0.31 g/l/h |
| Sp. Ethanol productivity (avg) | NR | 0.414 g/g/h | NR | 0.333 g/g/h | 0.795 g/g/h |
| Sp. Xylose consumption rate (avg) | NR | 0.940 g/g/h | NR | 0.734 g/g/h | 1.616 g/g/h |
| Time taken to completely consume xylose (hours) | 45 (starting OD = 0.1) | 85 (starting cell mass = 15 mg DCW/l) | NR | 50 (starting cell mass = 15 mg DCW/l) | 32 (Starting cell mass = 100 mg DCW/l) |

[1]Zhang et al, Science, 1995, 267, (5195), 240-243
[2]Kim et al, App Env Microbio, 2000, 66 (1), 186-93
[3]Lawford et al, App Biochem Biotech, 2002, 98-100, 429-448
DCW—Dry cell weight;
MR—Maximum reported value. Average value was not reported by the authors;
ND—Not Determined;
NR—Not reported

TABLE 8.3

Fermentation of xylose by ZM4/pZMETX A3 and A2 in a fermenter at pH 6 under anaerobic conditions. Fermentation data presented as a function of time.

|  | Duration (h) | Cellmass (g/l) | Xylose (% w/v) | Ethanol (% w/v) | Lactic Acid (% w/v) | Volumetric ethanol productivity | Yield (% theoretical yield) |
|---|---|---|---|---|---|---|---|
| ZM4/pZMETX A3 | 0 | 0.061 | 4.599 | 0.415 | 0.069 | — | — |
|  | 5.75 | 0.156 | 4.451 | 0.479 | 0.061 | 0.111 | 84.87% |
|  | 15.25 | 1.053 | 2.971 | 1.198 | 0.086 | 0.514 | 94.46% |
|  | 23.25 | 1.634 | 0.283 | 2.344 | 0.177 | 0.830 | 87.69% |
| ZM4/ZMETX A2 | 0 | 0.051 | 4.549 | 0.450 | 0.079 | — | — |
|  | 5.75 | 0.108 | 4.560 | 0.454 | 0.087 | 0.007 | — |
|  | 15.25 | 0.589 | 3.714 | 0.813 | 0.117 | 0.238 | 85.22% |
|  | 23.25 | 1.471 | 1.354 | 1.851 | 0.176 | 0.602 | 85.98% |
|  | 39.75 | 1.666 | 0.408 | 2.012 | 0.224 | 0.393 | 73.93% |

The aforementioned ZM4/pZMETX A3is to be deposited with the American Type Culture Collection and has an accession number and date of deposit of ATCC ®Patent Deposit Designation PTA-9991 received by ATCC on May 1, 2009.

The aforementioned ZM6014 is to be deposited with the American Type Culture Collection and has an accession number and date of deposit of ATCC ®Patent Deposit Designation PTA-9992 received by ATCC on May 1, 2009.

The claimed subject matter is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety to the extent that they are not inconsistent and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A process for making a *Zymomonas mobilis* strain more tolerant to an inhibitor comprising: a) growing a *Zymomonas mobilis* strain in a medium substantially free of an inhibitor; b) sequentially culturing the *Zymomonas mobilis* strain in the presence of consecutively higher concentrations of the inhibitor; and c) isolating a mutant strain having an adaptive mutation to a higher inhibitor concentration without NTG mutagenesis;
  wherein the inhibitor comprises acetic acid and wherein the isolated *Zymomonas mobilis* mutant strain is characterized by substantially exhibiting one or more of the following characteristics:
  (1) a lag phase of less than about one day; or
  (2) a specific growth rate of at least about 0.15 h$^{-1}$; or
  (3) an ethanol yield of at least about 95% of the theoretical yield;
  wherein the one or more characteristics are exhibited while fermenting at a pH of about 6 in an RM medium with 50 g/L glucose and 1.6% acetic acid concentration.

2. The process of claim 1, which further comprises screening the isolated mutant strain based upon growth rate, cell mass concentration, ethanol production or a combination thereof.

3. The process of claim 1, wherein the isolated strain is further optimized for inhibitor tolerance by chemical mutagenesis, recombinant DNA technology or any combination thereof.

4. The process of claim 1, wherein the sequential culturing is continued until the isolated mutant is stabilized for growth rate, cell mass concentration, ethanol production, or a combination thereof.

5. The process of claim 1, which further comprises: a) growing a *Zymomonas mobilis* strain in a suitable medium; b) sequentially culturing the *Zymomonas mobilis* strain in a medium characterized by a consecutively lower pH; and c) isolating a mutant strain adapted to a lower pH.

6. The process of claim 1 which further comprises fermenting a carbohydrate in the presence of the adapted mutant strain.

7. The process of claim 6, wherein the carbohydrate is derived from or is a portion of a biomass.

8. The process of claim 4, wherein the sequential culturing is continued until the isolated mutant is stabilized for growth rate.

9. The process of claim 4, wherein the sequential culturing is continued until the isolated mutant is stabilized for cell mass concentration.

10. The process of claim 4, wherein the sequential culturing is continued until the isolated mutant is stabilized for ethanol production.

11. The process of claim 4, wherein the sequential culturing is continued until the isolated mutant is stabilized for a combination of growth rate, cell mass concentration, and ethanol production.

12. The process of claim 1 wherein the isolated *Zymomonas mobilis* mutant strain is characterized by substantially exhibiting two or more of the following characteristics:
  (1) a lag phase of less than about one day; or
  (2) a specific growth rate of at least about 0.15 h$^{-1}$; or
  (3) an ethanol yield of at least about 95% of the theoretical yield;
  wherein the two or more characteristics are exhibited while fermenting at a pH of about 6 in an RM medium with 50 g/L glucose and 1.6% acetic acid concentration.

13. The process of claim 1 wherein the isolated *Zymomonas mobilis* mutant strain is characterized by substantially exhibiting the following characteristics:
  (1) a lag phase of less than about one day; and
  (2) a specific growth rate of at least about 0.15 h$^{-1}$; and
  (3) an ethanol yield of at least about 95% of the theoretical yield;
  wherein the characteristics are exhibited while fermenting at a pH of about 6 in an RM medium with 50 g/L glucose and 1.6% acetic acid concentration.

14. The process of claim 1 wherein the isolated *Zymomonas mobilis* mutant strain is characterized by substantially exhibiting a lag phase of less than about one day while fermenting at a pH of about 6 in an RM medium with 50 g/L glucose and 1.6% acetic acid concentration.

15. The process of claim 1 wherein the isolated *Zymomonas mobilis* mutant strain is characterized by substantially exhibiting a specific growth rate of at least about 0.15 h$^{-1}$ and while fermenting at a pH of about 6 in an RM medium with 50 g/L glucose and 1.6% acetic acid concentration.

16. The process of claim 1 wherein the isolated *Zymomonas mobilis* mutant strain is characterized by substantially exhibiting an ethanol yield of at least about 95% of the theoretical yield while fermenting at a pH of about 6 in an RM medium with 50 g/L glucose and 1.6% acetic acid concentration.

17. The process of claim 1 wherein the isolated *Zymomonas mobilis* mutant strain is characterized by substantially exhibiting one or more of the following characteristics:
   (1) a lag phase of less than nine hours; or
   (2) a specific growth rate of at least about 0.3 h$^{-1}$;
   wherein the one or more characteristics are exhibited while fermenting at a pH of about 6 in an RM medium with 50 g/L glucose and 1.6% acetic acid concentration.

* * * * *